(12) United States Patent
Ikemoto et al.

(10) Patent No.: US 11,173,472 B2
(45) Date of Patent: Nov. 16, 2021

(54) N-VINYL LACTAM-BASED CROSSLINKED POLYMER, COSMETIC, ABSORBENT AGENT FOR INK, AND ABSORBENT COMPOSITE

(71) Applicant: NIPPON SHOKUBAI CO., LTD., Osaka (JP)

(72) Inventors: Yui Ikemoto, Osaka (JP); Kazuhiro Okamura, Osaka (JP)

(73) Assignee: Nippon Shokubai Co., Ltd., Osaka (JP)

( * ) Notice: Subject to any disclaimer, the term of this patent is extended or adjusted under 35 U.S.C. 154(b) by 289 days.

(21) Appl. No.: 16/315,976

(22) PCT Filed: Jul. 7, 2017

(86) PCT No.: PCT/JP2017/025038
§ 371 (c)(1),
(2) Date: Jan. 7, 2019

(87) PCT Pub. No.: WO2018/008759
PCT Pub. Date: Jan. 11, 2018

(65) Prior Publication Data
US 2019/0300629 A1    Oct. 3, 2019

(30) Foreign Application Priority Data

Jul. 8, 2016 (JP) .............................. JP2016-136038
Jul. 26, 2016 (JP) .............................. JP2016-146535
Sep. 9, 2016 (JP) .............................. JP2016-176596
Nov. 25, 2016 (JP) .............................. JP2016-229398
Dec. 28, 2016 (JP) .............................. JP2016-255516
Feb. 27, 2017 (JP) .............................. JP2017-035357
Feb. 27, 2017 (JP) .............................. JP2017-035358

(51) Int. Cl.
| | |
|---|---|
| *B01J 20/26* | (2006.01) |
| *A61Q 19/00* | (2006.01) |
| *A61K 8/81* | (2006.01) |
| *A61L 9/01* | (2006.01) |
| *A61Q 5/00* | (2006.01) |
| *C08F 26/06* | (2006.01) |

(Continued)

(52) U.S. Cl.
CPC ............ *B01J 20/267* (2013.01); *A61K 8/0204* (2013.01); *A61K 8/027* (2013.01); *A61K 8/81* (2013.01); *A61K 8/817* (2013.01); *A61K 8/8182* (2013.01); *A61L 9/01* (2013.01); *A61L 9/014* (2013.01); *A61Q 1/00* (2013.01); *A61Q 5/00* (2013.01); *A61Q 15/00* (2013.01); *A61Q 19/00* (2013.01); *B01J 20/28023* (2013.01); *B01J 20/28033* (2013.01); *B01J 20/3014* (2013.01); *B01J 20/3021* (2013.01); *B01J 20/3078* (2013.01); *B01J 20/3085* (2013.01); *B41J 2/16517* (2013.01); *C08F 26/06* (2013.01); *C08F 26/10* (2013.01); *C08J 5/24* (2013.01); *C08L 39/04* (2013.01); *C09D 11/03* (2013.01); *C09D 11/106* (2013.01); *A61K 2800/546* (2013.01); *A61K 2800/5422* (2013.01); *A61L 2209/14* (2013.01); *A61L 2209/22* (2013.01); *C08J 2323/12* (2013.01); *C08J 2339/06* (2013.01); *C08J 2423/12* (2013.01); *C08J 2439/06* (2013.01); *C08L 2203/02* (2013.01)

(58) Field of Classification Search
USPC ..................... 526/264; 525/326.9; 502/402
See application file for complete search history.

(56) References Cited

U.S. PATENT DOCUMENTS

| | | |
|---|---|---|
| 4,201,846 A | 5/1980 | Kehr et al. |
| 4,443,366 A | 4/1984 | Sakagami et al. |

(Continued)

FOREIGN PATENT DOCUMENTS

| | | |
|---|---|---|
| CN | 1448415 | 10/2003 |
| CN | 1561234 | 1/2005 |

(Continued)

OTHER PUBLICATIONS

U.S. Appl. No. 16/315,506, filed Jan. 4, 2019, Aug. 26, 2021.
U.S. Appl. No. 16/315,970, filed Jan. 7, 2019, Aug. 26, 2021.

*Primary Examiner* — Fred M Teskin
(74) *Attorney, Agent, or Firm* — Hamre, Schumann, Mueller & Larson, P.C.

(57) ABSTRACT

The invention aims to provide a crosslinked polymer having excellent moisture retention properties, an excellent ethanol absorption capacity, excellent adhesiveness to the skin when applied to the skin as a cosmetic, and a high concentration of an effective component. The invention relates to a N-vinyl lactam-based crosslinked polymer including: a structural unit derived from a N-vinyl lactam; and a structural unit derived from a crosslinking agent, the N-vinyl lactam-based crosslinked polymer having an ethanol absorption capacity of 3 to 40 g per 1 g of the N-vinyl lactam-based crosslinked polymer, the N-vinyl lactam-based crosslinked polymer containing a particle having an aspect ratio determined by the following method of 1.15 to 10 in a proportion of 10% to 100% (by number) of the total number of the N-vinyl lactam-based crosslinked polymer and having a proportion of an extractable of 35 mass % or less in 100 mass % of the entire polymer, the method being "method of measuring aspect ratio" in which the aspect ratio is determined as a value obtained by measuring the major and minor axes of a primary particle of the N-vinyl lactam-based cross-linked polymer with an optical or electron microscope and dividing the major axis by the minor axis.

22 Claims, No Drawings

(51) Int. Cl.
  *A61Q 1/00*     (2006.01)
  *B01J 20/30*    (2006.01)
  *C08L 39/04*    (2006.01)
  *C09D 11/03*    (2014.01)
  *C09D 11/106*   (2014.01)
  *A61K 8/02*     (2006.01)
  *A61L 9/014*    (2006.01)
  *A61Q 15/00*    (2006.01)
  *B01J 20/28*    (2006.01)
  *B41J 2/165*    (2006.01)
  *C08F 26/10*    (2006.01)
  *C08J 5/24*     (2006.01)

(56) References Cited

U.S. PATENT DOCUMENTS

| | | | |
|---|---|---|---|
| 4,718,899 | A  | 1/1988  | Itoh et al. |
| 5,139,770 | A  | 8/1992  | Shih et al. |
| 5,162,417 | A  | 11/1992 | Chuang et al. |
| 5,830,964 | A  | 11/1998 | Liu et al. |
| 6,103,425 | A  | 8/2000  | Harada et al. |
| 6,234,618 | B1 | 5/2001  | Yamamoto et al. |
| 7,422,735 | B1 | 9/2008  | Hossel et al. |
| 2001/0020078 | A1 | 9/2001  | Tomihisa et al. |
| 2003/0191260 | A1 | 10/2003 | Nakata |
| 2004/0249079 | A1 | 12/2004 | Funk et al. |
| 2006/0238564 | A1 | 10/2006 | Ishihara |
| 2010/0137825 | A1 | 6/2010  | Een et al. |
| 2012/0093748 | A1 | 4/2012  | Fares et al. |
| 2012/0294818 | A1 | 11/2012 | Fares et al. |
| 2013/0017160 | A1 | 1/2013  | Fares et al. |
| 2014/0341957 | A1 | 11/2014 | Yang et al. |
| 2015/0035205 | A1 | 2/2015  | Kuramoto |

FOREIGN PATENT DOCUMENTS

| | | |
|---|---|---|
| CN | 101506253    | 8/2009  |
| CN | 102093809    | 6/2011  |
| CN | 102304200    | 1/2012  |
| CN | 103917624    | 7/2014  |
| DE | 1953121      | 4/1971  |
| DE | 698 15 614   | 5/2004  |
| EP | 0 023 322    | 2/1981  |
| EP | 0 904 771    | 3/1999  |
| JP | 56-015839    | 2/1981  |
| JP | 3-104683     | 5/1991  |
| JP | 7-090722     | 4/1995  |
| JP | 7-229125     | 8/1995  |
| JP | 9-031983     | 2/1997  |
| JP | 9-183231     | 7/1997  |
| JP | 9-183854     | 7/1997  |
| JP | 10-005582    | 1/1998  |
| JP | 10-101745    | 4/1998  |
| JP | 2000-135797  | 5/2000  |
| JP | 2000-239342  | 9/2000  |
| JP | 2001-055321  | 2/2001  |
| JP | 2001-226431  | 8/2001  |
| JP | 2001-301379  | 10/2001 |
| JP | 2004-161829  | 6/2004  |
| JP | 2004-315811  | 11/2004 |
| JP | 2005131904   | 5/2005  |
| JP | 2005-219482  | 8/2005  |
| JP | 2005-281665  | 10/2005 |
| JP | 2006-272734  | 10/2006 |
| JP | 2007-045776  | 2/2007  |
| JP | 2008-086590  | 4/2008  |
| JP | 2009-274302  | 11/2009 |
| JP | 2010-248310  | 11/2010 |
| JP | 2012-072277  | 4/2012  |
| JP | 2012-520317  | 9/2012  |
| JP | 2014-097105  | 5/2014  |
| JP | 2015-030121  | 2/2015  |
| JP | 2015-047570  | 3/2015  |
| JP | 2015-123083  | 7/2015  |
| JP | 2015-205791  | 11/2015 |
| JP | 2013-255556  | 3/2016  |
| JP | 2017-043778  | 3/2017  |
| JP | 2017-052911  | 3/2017  |
| JP | 2017-113709  | 6/2017  |
| JP | 2015-142909  | 7/2019  |
| WO | 2007/149804  | 12/2007 |

N-VINYL LACTAM-BASED CROSSLINKED POLYMER, COSMETIC, ABSORBENT AGENT FOR INK, AND ABSORBENT COMPOSITE

TECHNICAL FIELD

The invention relates to a N-vinyl lactam-based crosslinked polymer, a cosmetic, an absorbent composite, and an ink absorbing agent. The invention specifically relates to a N-vinyl lactam-based crosslinked polymer, a cosmetic, an absorbent composite, and an ink absorbing agent useful for skin cosmetics, skin preparations for external use, hair cosmetics, ink absorbing agents for use in writing instruments and ink jet recording apparatuses, deodorants, and fragrance agents, for example.

BACKGROUND ART

Polymers having a lactam structure, which have hydrophilicity and are highly safe to the human body and the environment, are used in various applications.

In particular, crosslinked polymers having a lactam structure are useful in applications for absorption and retention of liquid such as water, and are therefore widely used as water-absorbent (liquid-absorbent) resins for disposable diapers, for example. With regard to such liquid-absorbent resins, Patent Literature Documents 1 to 4 disclose liquid-absorbent resins prepared by copolymerizing a monomer component containing a cyclic vinyl lactam with a crosslinking agent or production methods thereof.

Further, crosslinked polymers having a lactam structure are blended into various cosmetic products as a carrier for a surfactant, a fragrance component, a deodorant component, or a cosmetic component; a humectant; a thickening agent; or a dispersant (see Patent Literature Documents 5 to 7).

Water-absorbent materials primarily containing a polyacrylic acid (salt) have been conventionally developed and have been used in various fields such as the hygiene field including the field of hygiene articles (e.g., diapers, sanitary products), the medical field, the civil engineering and construction field, the food field, the industrial field, the field of soil modifiers, and the agriculture/horticulture field.

For example, Patent Literature Documents 8 to 10 disclose an absorbent composite or ink absorber which includes a base material and a crosslinked body primarily containing a polyacrylic acid (salt).

Further, writing utensils such as ball-point pens and coating utensils are equipped with an ink absorber that absorbs an excess ink or keeps the density of a reserved ink uniform (see Patent Literature Documents 11 to 17).

CITATION LIST

Patent Literature

Patent Literature 1: JP H10-5582 A
Patent Literature 2: JP H10-101745 A
Patent Literature 3: JP 2001-226431 A
Patent Literature 4: JP 2012-072277 A
Patent Literature 5: JP 2007-45776 A
Patent Literature 6: JP 2012-520317 T
Patent Literature 7: U.S. Pat. No. 5,139,770
Patent Literature 8: JP 2008-86590 A
Patent Literature 9: JP 2009-274302 A
Patent Literature 10: JP 2000-135797 A
Patent Literature 11: JP 2005-219482 A
Patent Literature 12: JP 2001-301379 A
Patent Literature 13: JP H09-183231 A
Patent Literature 14: JP 2000-135797 A
Patent Literature 15: JP 2000-239342 A
Patent Literature 16: JP 2009-274302 A
Patent Literature 17: JP 2006-272734 A

SUMMARY OF INVENTION

Technical Problem

In order to use such N-vinyl lactam-based crosslinked polymers as disclosed above in various applications, they need to have, in addition to an excellent liquid absorption capacity, sufficient gel-pulverizability. However, conventional N-vinyl lactam-based crosslinked polymers are not enough to satisfy a liquid absorption capacity and sufficient gel-pulverizability at the same time. For cosmetic applications, crosslinked polymers need to have not only excellent moisture retention properties, but also excellent absorption capacity for ethanol usually contained in cosmetics, excellent adhesiveness to the skin when applied to the skin as a cosmetic, and a high concentration of an effective component.

Although various cosmetics such as cosmetics containing a moisturizer as an additive are disclosed, recent consumer demand for safety has led to a need for development of cosmetics containing an additive that is safer and contains particles having better adhesiveness and better applicability to the skin.

The above-described various absorbent composites (ink absorbers) have problems as follows. Conventional absorbent composites primarily containing a polyacrylic acid (salt) are capable of absorbing only water and a water-rich solution. For example, conventional absorbent composites are capable of absorbing an organic solvent as a water-rich aqueous solution. However, when the water evaporates and the organic solvent component is concentrated, the absorbent composite cannot hold the liquid any longer, causing liquid leakage (discharge). In order to solve such a problem, an absorbent composite having an excellent absorption capacity for various liquids is required to be developed.

Further, although various ink absorbers and ink absorbing agents have been developed as described above, the ink absorbers and the ink absorbing agents disclosed in Patent Literature Documents 11 to 16 are not satisfactory in terms of liquid absorption capacity because they cannot absorb a sufficient amount of ink or sufficient types of ink. In addition, the invention disclosed in Patent Literature 17 only relates to easy absorption (without foaming) of ink with an absorber by impregnating the absorber with an emulsion or applying an emulsion to the surface of the absorber, for example. An emulsion is not used for holding ink, and the absorber itself has a low absorption capacity.

The invention has been made in view of the above-mentioned state of the art and aims to provide a crosslinked polymer having an excellent liquid absorption capacity and sufficient gel-pulverizability.

The invention also aims to provide a crosslinked polymer having excellent moisture retention properties, an excellent ethanol absorption capacity, excellent adhesiveness to the skin when applied to the skin as a cosmetic, and a high concentration of an effective component.

The invention also aims to provide a cosmetic better than conventional cosmetics, that is, a cosmetic containing an additive that is safer for the human body and has better adhesiveness to the skin, and a cosmetic containing an additive that is safer for the human body and has better applicability to the skin.

The invention also aims to provide an absorbent composite having an excellent absorption capacity for various liquids.

The invention also aims to provide an ink absorbing agent having a better ink absorption capacity than conventional ink absorbing agents.

Solution to Problem

The inventors variously studied a crosslinked polymer having an excellent liquid absorption capacity and gel-pulverizability and found that a N-vinyl lactam-based crosslinked polymer containing a structural unit derived from a cyanuric acid structure-containing crosslinkable monomer in a ratio within a specific range has an excellent liquid absorption capacity and sufficient gel-pulverizability. As a result, they arrived at an admirable solution to the above-mentioned problems, completing a first aspect of the invention.

The inventors also variously studied a crosslinked polymer and found that a N-vinyl lactam-based crosslinked polymer having an aspect ratio within a specific range and a specific water absorption capacity has excellent moisture retention properties, an excellent ethanol absorption capacity, excellent adhesiveness to the skin when applied to the skin as a cosmetic, and a high concentration of an effective component. As a result, they arrived at an admirable solution to the above-mentioned problems, completing a second aspect of the invention.

The inventors also variously studied a cosmetic and found that a cyclic N-vinyl lactam-based crosslinked body having a particle aspect ratio of 1.15 to 10 and including a structural unit derived from a cyclic N-vinyl lactam is highly safe, and exerts moisturizing, oil-absorbing, and thickening effects, and has excellent adhesiveness to the skin. They also found that a cyclic N-vinyl lactam-based crosslinked polymer including a structural unit derived from a cyclic N-vinyl lactam is highly safe, exerts moisturizing and oil-absorbing effects, and has good applicability to the skin when it is used in the form of a 5 mass % aqueous dispersion having a viscosity of 100 mPa·s or higher and lower than 10000 mPa·s. They found that such a crosslinked body and a crosslinked polymer are suitable for cosmetic applications. As a result, they arrived at an admirable solution to the above-mentioned problems, completing a third aspect of the invention.

The inventors also variously studied an absorbent composite and found that an absorbent composite containing a nonionic crosslinked polymer and an absorbent base material has excellent absorption performance to various types of liquids when the absorbent composite has a mass ratio between the nonionic crosslinked polymer and the absorbent base material within a specific range or a thickness within a specific range. As a result, they arrived at an admirable solution to the above-mentioned problems, completing a fourth aspect of the invention.

The inventors also variously studied an ink absorbing agent and found that a N-vinyl lactam-based crosslinked polymer has an excellent liquid absorption capacity in terms of both the amount and types of ink and is suitable as an ink absorbing agent. As a result, they arrived at an admirable solution to the above-mentioned problems, completing a fifth aspect of the invention.

That is, the first aspect of the invention relates to a N-vinyl lactam-based crosslinked polymer including:
a structural unit derived from a N-vinyl lactam-based monomer; and
a structural unit derived from a cyanuric acid structure-containing crosslinkable monomer,
the N-vinyl lactam-based crosslinked polymer containing the structural unit derived from a cyanuric acid structure-containing crosslinkable monomer in a ratio of 0.12 to 0.48 mol % to 100 mol % of all structural units.

The second aspect of the invention relates to a N-vinyl lactam-based crosslinked polymer including a structural unit derived from a N-vinyl lactam and a structural unit derived from a crosslinking agent. The N-vinyl lactam-based crosslinked polymer has an ethanol absorption capacity of 3 to 40 g per 1 g of the N-vinyl lactam-based crosslinked polymer, contains particles having an aspect ratio determined by the method described below of 1.15 to 10 in a proportion of 10% to 100% (by number) of the total number of the N-vinyl lactam-based crosslinked polymer, and has a proportion of an extractable of 35 mass % or less in 100 mass % of the entire polymer.

<Method of Measuring Aspect Ratio>

The aspect ratio is determined as a value obtained by measuring the major and minor axes of a primary particle of the N-vinyl lactam-based cross-linked polymer with an optical or electron microscope and dividing the major axis by the minor axis.

A first embodiment of the third aspect of the invention relates to a cosmetic that includes a cyclic N-vinyl lactam-based crosslinked body including a structural unit derived from a cyclic N-vinyl lactam. The cyclic N-vinyl lactam-based crosslinked body is a cosmetic having a viscosity measured under the following conditions of 100 mPa·s or higher and lower than 10000 mPa·s.

<Viscosity Measurement Conditions>

Sample: A 5 mass % aqueous dispersion of the cyclic N-vinyl lactam-based crosslinked body after 16-hour stirring Measuring equipment: The sample is measured using a B-type viscometer at 25° C.

Measurement conditions: Rotor No. 4, rotation speed: 30 rpm

A second embodiment of the third aspect of the invention relates to a cosmetic that includes a cyclic N-vinyl lactam-based crosslinked polymer including a structural unit derived from a cyclic N-vinyl lactam. The cyclic N-vinyl lactam-based crosslinked polymer in particulate form contains particles having an aspect ratio determined by the method described below of 1.1 to 10 in a proportion of 10% to 100% (by number) of the total number of the cyclic N-vinyl lactam-based crosslinked polymer particles.

<Method of Measuring Aspect Ratio>

The aspect ratio is determined as a value obtained by measuring the major and minor axes of a primary particle of the cyclic N-vinyl lactam-based cross-linked polymer with an optical or electron microscope and dividing the major axis by the minor axis.

A first embodiment of the fourth aspect of the invention relates to an absorbent composite including a nonionic crosslinked polymer and an absorbent base material, the absorbent composite having a mass ratio of the nonionic crosslinked polymer to the absorbent base material (nonionic crosslinked polymer/absorbent base material) of 0.1 or more and less than 2.

A second embodiment of the fourth aspect of the invention relates to an absorbent composite including a nonionic crosslinked polymer and an absorbent base material, the absorbent composite having a mass ratio of the nonionic crosslinked polymer to the absorbent base material (nonionic crosslinked polymer/absorbent base material) of 2.5 or more and not more than 15.

The fifth aspect of the invention relates to an ink absorbing agent containing a N-vinyl lactam-based crosslinked polymer.

Advantageous Effects of Invention

The N-vinyl lactam-based crosslinked polymer of the first aspect of the invention having the above-described features has an excellent liquid absorption capacity and sufficient gel-pulverizability and is suitable for ink absorbing agents for use in writing instruments and ink jet recording apparatuses, deodorants, fragrance agents, and cosmetics, for example.

The N-vinyl lactam-based crosslinked polymer of the second aspect of the invention having the above-described features has excellent moisture retention properties, an excellent ethanol absorption capacity, excellent adhesiveness to the skin when applied to the skin as a cosmetic, and a high concentration of an effective component. Such a N-vinyl lactam-based crosslinked polymer is suitable for cosmetics, for example.

The cosmetic of the third aspect of the invention having the above-described features contains an additive safer for the human body than additives contained in conventional cosmetics. Such a cosmetic is suitable for skin cosmetics, skin preparations for external use, and hair cosmetics, for example.

The absorbent composite of the fourth aspect of the invention having the above-described features has an excellent absorption capacity for various liquids and is suitable for absorbent materials for inks, for example.

The ink absorbing agent of the fifth aspect of the invention having the above-described features has an excellent ink absorption capacity and is suitable for ink jet recording apparatuses and writing instruments, for example.

The following specifically describes the invention. The matters referring to "the invention" herein are common to the first to fifth aspects of the invention.

A combination of two or more of the preferred embodiments of the invention described below is also a preferred embodiment of the invention.

<First Aspect of the Invention: N-Vinyl Lactam-Based Crosslinked Polymer>

The N-vinyl lactam-based crosslinked polymer of the first aspect of the invention (hereinafter, also referred to as crosslinked polymer of the first aspect of the invention) includes a structural unit derived from a N-vinyl lactam (N-vinyl lactam-based monomer).

The "structural unit derived from a N-vinyl lactam" indicates a structural unit having the same structure as the structural unit formed by polymerizing a N-vinyl lactam (N-vinyl lactam-based monomer). That is, the structural unit derived from a N-vinyl lactam encompasses a structural unit formed by a method other than polymerization of a N-vinyl lactam as long as it has the same structure as the structural unit formed by polymerizing a N-vinyl lactam. The crosslinked polymer of the first aspect of the invention including a structural unit derived from a N-vinyl lactam is capable of absorbing or retaining water or other solvents, and thus can be used in various applications as described below.

The crosslinked polymer of the first aspect of the invention is capable of absorbing solvents such as an oil, and is thus suitable for applications of an ink absorbing agent for use in writing instruments and ink jet recording apparatuses.

The crosslinked polymer of the first aspect of the invention is also capable of absorbing odor components, and is thus suitable for deodorant applications. The crosslinked polymer is also capable of exerting fragrance effects by absorbing a fragrance component, and is thus suitable for fragrance applications.

The crosslinked polymer of the first aspect of the invention is capable of exerting a moisturizing effect by absorbing and retaining liquids such as water. Further, the nonionic properties of the N-vinyl lactam make the crosslinked polymer highly safe, and such a crosslinked polymer is suitable for cosmetic applications. The crosslinked polymer having a crosslinked structure swells into a gel when the polymer absorbs water or other solvents. Therefore, the polymer exerts a thickening effect and further enhances the adhesiveness to the skin of a cosmetic containing the polymer.

The N-vinyl lactam-based crosslinked polymer of the first aspect of the invention includes a structural unit derived from a cyanuric acid structure-containing crosslinkable monomer.

Herein, the cyanuric acid structure-containing crosslinkable monomer means a crosslinkable monomer having a structure obtained by removing at least two hydrogen atoms from a cyanuric acid (hereinafter, also referred to as cyanuric acid-derived structure) and at least two carbon-carbon double bonds. The at least two carbon-carbon double bonds of the cyanuric acid structure-containing crosslinkable monomer each react with a carbon-carbon double bond of another molecule, so that a crosslinked structure is formed.

Since the cyanuric acid structure-containing crosslinkable monomer is highly reactive with a N-vinyl lactam, the presence of the cyanuric acid structure-containing crosslinkable monomer can reduce an extractable (uncrosslinked polymer soluble in water) in the crosslinked polymer. As a result, the concentration of an effective component in the crosslinked polymer increases, and a better liquid absorption capacity is obtained.

The crosslinked polymer contains the structural unit derived from a cyanuric acid structure-containing crosslinkable monomer in a ratio of 0.12 to 0.48 mol % to 100 mol % of all structural units. The crosslinked polymer having such a ratio of the structural unit retains a high liquid absorption capacity and has suitable gel strength and thus has more sufficient gel-pulverizability. Also, the cyanuric acid structure-containing crosslinkable monomer has less skin irritation and is highly safe. Thus, the N-vinyl lactam-based crosslinked polymer of the first aspect of the invention is suitable for cosmetic applications. The ratio of the structural unit is preferably 0.12 to 0.47 mol %, more preferably 0.13 to 0.47 mol %, still more preferably 0.15 to 0.47 mol %, particularly preferably 0.15 to 0.45 mol %, most preferably 0.16 to 0.45 mol %.

Here, the ratio of the structural unit derived from a cyanuric acid structure-containing crosslinkable monomer may be determined by the expression: [Structural unit derived from cyanuric acid structure-containing crosslinkable monomer (number of moles)]÷[all structural units (sum of structural unit derived from N-vinyl lactam and structural unit derived from monomer (E)) (number of moles)]×100 (mol %).

The cyanuric acid structure-containing crosslinkable monomer may be any monomer having a cyanuric acid-derived structure and at least two carbon-carbon double bonds and is preferably a monomer represented by the following formula (1):

[Chem. 1]

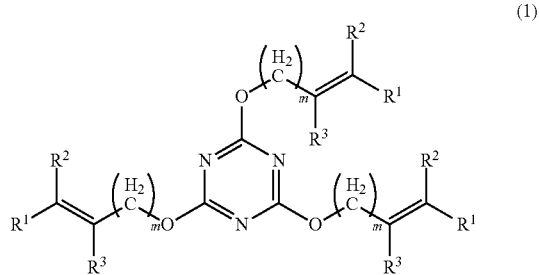

(1)

wherein $R^2$, $R^2$, and $R^3$ are the same as or different from each other and each represent a hydrogen atom or an optionally substituted C1-C10 alkyl group; m's are the same as or different from each other and each represent an integer of 0 to 4.

The number of carbon atoms of the alkyl group for $R^2$ to $R^3$ is preferably 1 to 6, more preferably 1 to 4. The alkyl group is still more preferably a methyl group or an ethyl group, particularly preferably a methyl group.

Examples of the substituent in $R^2$ to $R^3$ include, but are not limited to, an ethylenically unsaturated hydrocarbon group; a carboxyl group and a sulfonic acid group and esters and salts thereof; and a reactive functional group condensable with a crosslinking agent, such as an amino group or a hydroxy group.

$R^2$ to $R^3$ each preferably represent a hydrogen atom.

Further, m is preferably 0, 1, or 2, more preferably 1.

The compound represented by the formula (1) is preferably triallyl cyanurate.

The "N-vinyl lactam" may be any monomer having a N-vinyl lactam structure, preferably a structure represented by the following formula (2):

[Chem. 2]

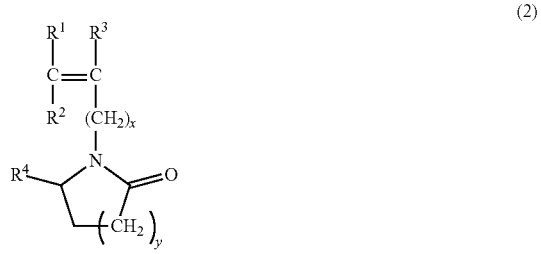

(2)

wherein $R^2$, $R^2$, $R^3$ and $R^4$ are the same as or different from each other and each represent a hydrogen atom or an optionally substituted C1-C10 alkyl group; x represents an integer of 0 to 4; and y represents an integer of 1 to 3.

The number of carbon atoms of the alkyl group for $R^2$ to $R^4$ is preferably 1 to 6, more preferably 1 to 4. The alkyl group is still more preferably a methyl group or an ethyl group, particularly preferably a methyl group.

Examples of the substituent in $R^2$ to $R^4$ include, but are not limited to, an ethylenically unsaturated hydrocarbon group; a carboxyl group, a sulfonic acid group, and esters and salts thereof; and a reactive functional group condensable with a crosslinking agent, such as an amino group or a hydroxy group.

In cases where at least one of $R^2$ to $R^4$ in the formula (2) is a C1-C10 alkyl group containing as a substituent a reactive functional group condensable with a crosslinking agent, a crosslinked structure can be formed by the following process (2) or (3).

$R^2$ to $R^3$ each preferably represent a hydrogen atom. $R^4$ preferably represents a hydrogen atom or a methyl group, more preferably a hydrogen atom.

Further, x is preferably an integer of 0 to 2, more preferably an integer of 0 or 1, most preferably 0.

Further, y is preferably 1 or 2, more preferably 1.

Examples of the compound represented by the formula (2) include N-vinylpyrrolidone, N-vinyl-5-methylpyrrolidone, N-vinylpiperidone, N-vinylcaprolactam, and 1-(2-propenyl)-2-pyrrolidone. One or two or more of these may be used. The N-vinyl lactam is preferably an unsaturated monomer having a pyrrolidone ring, more preferably N-vinylpyrrolidone.

The crosslinked polymer of the first aspect of the invention may have a crosslinked structure other than, and in addition to, the structural unit derived from a cyanuric acid structure-containing crosslinkable monomer. The crosslinked structure can be formed by any of the following processes (1) to (5), for example.

(1) A monomer component containing a crosslinkable monomer other than, and in addition to, the cyanuric acid structure-containing crosslinkable monomer is polymerized to produce a polymer having a crosslinked structure.

(2) A monomer component containing a reactive functional group-containing monomer is polymerized to obtain a polymer, and the polymer is reacted with a crosslinking agent having multiple functional groups capable of reacting with the reactive functional group to form a crosslinked structure.

(3) A monomer component containing a monomer 1 having a reactive functional group and a monomer 2 having a reactive functional group capable of reacting with the reactive functional group of the monomer 1 is polymerized, and then the reactive functional group of the monomer 1 is reacted with the reactive functional group of the monomer 2 to form a crosslinked structure (self-crosslinking).

(4) Radicals are produced in polymers, and a crosslinked structure is formed between the polymers containing radicals (self-crosslinking).

(5) Radicals are produced in a polymer, and the polymer containing radicals is reacted with a crosslinkable monomer to form a crosslinked structure.

The crosslinkable monomers in the processes (1) and (5) are described below.

In the case of the crosslinked polymer of the first aspect of the invention having a crosslinked structure formed by the process (2) or (3), the crosslinked polymer of the first aspect of the invention includes a structural unit derived from a reactive functional group-containing monomer as the structural unit derived from a N-vinyl lactam-based monomer or the structural unit derived from a monomer (E) described below.

Examples the reactive functional groups in the processes (2) and (3) include, but are not limited to, a carboxyl group, a sulfonic acid group, and esters and salts thereof; an amino group; and a hydroxy group.

In cases where the crosslinked structure is formed by the process (3), examples of a combination of the reactive functional groups reactive with each other include a combination of a carboxyl group (or an ester or salt thereof) and a hydroxy group, a combination of a sulfonic acid group (or an ester or salt thereof) and a hydroxy group, a combination of a carboxyl group (or an ester or salt thereof) and an amino group, a combination of a carboxyl group (or an ester or salt thereof) and an oxazoline group, a combination of a sulfonic acid group (or an ester or salt thereof) and an amino group, a combination of an isocyanate group and a hydroxy group, a combination of an isocyanate group and an amino group, a combination of an oxazoline group and a hydroxy group, and a combination of an oxazoline group and a mercapto group. In cases where the crosslinked structure in the crosslinked polymer of the first aspect of the invention is formed by the process (2), examples of a combination of the reactive functional group of the monomer and the functional groups of a crosslinking agent capable of reacting with the reactive functional group are the same as the aforementioned examples of the combination.

The crosslinking agent in the process (2) may be any one that has multiple functional groups capable of reacting with the reactive functional group. Examples thereof include ethylenediamine, hexamethylenediamine, phenylenediamine, an oxazoline group-containing polymer (EPOCROS, Nippon Shokubai Co., Ltd.), butanediol, tolylene diisocyanate, and hexamethylene diisocyanate.

In cases where the crosslinked structure in the crosslinked polymer of the invention is formed by the process (1) or (5), the crosslinkable monomer is a compound having at least two polymerizable ethylenically unsaturated hydrocarbon groups in one molecule, preferably a compound having at least two radical polymerizable ethylenically unsaturated hydrocarbon groups in one molecule.

The N-vinyl lactam-based monomer and the crosslinkable monomer both encompass a compound having a lactam structure and at least two ethylenically unsaturated hydrocarbon groups.

Specific examples of the crosslinkable monomer other than the cyanuric acid structure-containing crosslinkable monomer include C1-C4 alkylene group-containing N,N'-alkylene bis(meth)acrylamides such as N,N'-methylene bis(meth)acrylamide; C1-C6 alkylene group-containing alkylene bis(N-vinylamides) such as 1,4-butylene bis(N-vinylamide); C1-C4 alkylene group-containing (poly)alkylene glycol di(meth)acrylates such as (poly)ethylene glycol di(meth)acrylate and (poly)propylene glycol di(meth)acrylate; trimethylolpropane (di or tri) (meth)acrylates optionally modified with a C1-C4 alkylene group-containing alkylene oxide, such as trimethyrolpropane tri(meth)acrylate, trimethylolpropane di(meth)acrylate, and ethylene oxide-modified trimethyrolpropane tri(meth)acrylate; glycerol (di or tri) (meth)acrylates such as glycerol tri(meth)acrylate and glycerol acrylate methacrylate; pentaerythritol (di, tri, or tetra) (meth)acrylates such as pentaerythritol tetra(meth)acrylate; dipentaerythritol (di, tri, tetra, penta, or hexa) (meth)acrylates such as dipentaerythritol hexa(meth)acrylate; pentaerythritol (di, tri, or tetra) (meth)allyl ethers such as pentaerythritol tri(meth)allyl ether; C9-C20 triallyl compounds such as triallyl isocyanurate, triallyl phosphate, and triallylamine; C6-C20 diallyl compounds such as diallyl carbonate and 1,3-bis(allyloxy)-2-propanol; C4-C20 (di or tri)vinyl compounds such as divinyl ether, divinyl ketone, trivinylbenzene, divinylethylene urea, divinyltoluene, and divinylxylene; C2-C20 diisocyanates such as tolylene diisocyanate and hexamethylene diisocyanate; poly(meth)allyloxy alkanes, N,N'-divinyl-2-imidazolidinone, N,N'-1,4-butylene bis(N-divinylacetamide), and (di, tri, tetra, penta, hexa, hepta, or octa)allyl sucrose. Each of these may be used alone, or two or more of these may be used in combination.

Preferred among the crosslinkable monomers are the compounds having at least two allyl groups because the use of such compounds tends to reduce a residual N-vinyl lactam and an extractable (uncrosslinked polymer fraction soluble in water). Specifically, preferred are pentaerythritol (di, tri, or tetra) (meth)allyl ethers, triallyl isocyanurate, triallyl phosphate, triallylamine, diallyl carbonate, 1,3-bis(allyloxy)-2-propanol, divinylethylene urea, 1,4-butylene bis(N-vinylamide), and (di, tri, tetra, penta, hexa, hepta, or octa)allyl sucrose, for example.

More preferred are pentaerythritol (di, tri, or tetra)allyl ethers and (di, tri, tetra, penta, hexa, hepta, or octa)allyl sucrose. A N-vinyl lactam-based crosslinked polymer including a structural unit derived from a pentaerythritol (di, tri, or tetra)allyl ether or (di, tri, tetra, penta, hexa, hepta, or octa)allyl sucrose is one preferred embodiment of the invention. Such a crosslinked polymer is more suitable for cosmetic applications because pentaerythritol (di, tri, or tetra) allyl ethers and (di, tri, tetra, penta, hexa, hepta, or octa)allyl sucrose are highly safe.

The polyalkylene glycol di(meth)acrylate preferably has 2 or more and 50 or less, more preferably 2 or more and 20 or less, still more preferably 2 or more and 10 or less oxyalkylene groups in one molecule. In the polyalkylene glycol di(meth)acrylate, the proportion of an oxyethylene group is preferably 50 to 100 mol %, more preferably 80 to 100 mol % in 100 mol % of the oxyalkylene groups.

In the case of the trimethylolpropane (di or tri) (meth) acrylates modified with a C1-C4 alkylene group-containing alkylene oxide, the average number of alkylene oxides added in one molecule of each of the trimethylolpropane (di or tri) (meth)acrylates is preferably the same as described above.

The structural unit derived from a crosslinkable monomer is a structural unit having the same structure as the structural unit in which at least one of the polymerizable carbon-carbon double bond groups of the crosslinkable monomer is converted into a single bond. That is, the structural unit derived from a crosslinkable monomer encompasses a structural unit formed by polymerizing a monomer other than the crosslinkable monomer to form a polymer and post-crosslinking the polymer as long as the structural unit has the same structure as the structural unit in which at least one of the polymerizable carbon-carbon double bond groups of the crosslinkable monomer is converted into a single bond.

The crosslinked polymer of the first aspect of the invention may contain a structural unit (e) derived from a monomer (E) other than the N-vinyl lactam-based monomer, the cyanuric acid structure-containing crosslinkable monomer, the crosslinkable monomer other than the cyanuric acid structure-containing crosslinkable monomer, and the crosslinking agent. The monomer (E) may be any compound that is copolymerizable with a N-vinyl lactam-based monomer, is free from a lactam structure, and has one ethylenically unsaturated hydrocarbon group. Examples of the monomer (E) include (i) unsaturated monocarboxylic acids such as acrylic acid and methacrylic acid and salts thereof; (ii) unsaturated dicarboxylic acids such as fumaric acid, maleic acid, methylene glutaric acid, and itaconic acid and salts thereof (which may be either monovalent salts or divalent salts); (iii) unsaturated sulfonic acids such as 3-allyloxy-2-hydroxypropane sulfonic acid, (meth)allylsulfonic acid, and isoprene sulfonic acid and salts thereof; (iv) hydroxyethyl (meth)acrylate, hydroxypropyl (meth)acrylate, 3-(meth)allyloxy-1,2-dihydroxypropane; unsaturated alcohols such as (meth)allyl alcohol and isoprenol; and alkylene oxide adducts of these in which an alkylene oxide is added to a hydroxy group of these; (v) (meth)acrylates such as methyl (meth)acrylate, ethyl (meth)acrylate, butyl (meth)acrylate, and cyclohexyl (meth)acrylate; (vi) N-substituted or unsubstituted (meth)acrylamides such as (meth)acrylamide, N-monomethyl (meth)acrylamide, N-monoethyl (meth) acrylamide, and N,N-dimethyl (meth)acrylamide; (vii) vinyl aryl monomers such as styrene, indene, and vinylaniline; (viii) alkenes such as ethylene, propylene, butadiene, isobutylene, and octene; (ix) vinyl carboxylates such as vinyl acetate and vinyl propionate; (x) unsaturated amines such as N,N-dimethylaminoethyl (meth)acrylate, N,N-dimethylaminoethyl (meth)acrylamide, vinylpyridine, and vinylimidazole and salts and quaternized compounds thereof; (xi) vinylamides such as vinylformamide, vinylacetamide, and vinyloxazolidone; (xii) unsaturated anhydrides such as maleic anhydride and itaconic anhydride; (xiii) vinyl ethylene carbonates and derivatives thereof; (xiv) (meth) acrylic acid-2-sulfoethyl ester and derivatives thereof; and (xv) vinyl ethers such as methyl vinyl ether, ethyl vinyl ether, and butyl vinyl ether.

Preferred among these are the monomers listed as (i) to (x), more preferred are the monomers listed as (i), (v), (vi), (vii), (ix), and (x).

Each of these may be used alone, or two or more of these may be used in combination.

Examples of the salts in (i) to (iii) and (x) include metal salts, ammonium salts, and organic amine salts. Examples of the alkylene oxide in (iv) include ethylene oxide and propylene oxide. Preferred is a C1-C20 alkylene oxide, and more preferred is a C1-C4 alkylene oxide. The number of moles of alkylene oxide added in (iv) is preferably 0 to 50 mol, more preferably 0 to 20 mol per 1 mol of each compound in (iv).

The monomer (E) is preferably a C2-C20 monomer, more preferably a C2-C15 monomer, still more preferably a C2-C10 monomer. In cases where the monomer (E) is an alkylene oxide adduct, the number of carbon atoms of the structural site other than the alkylene oxide structural site preferably satisfies the number of carbon atoms within these ranges.

In the N-vinyl lactam-based crosslinked polymer, the proportion of the structural unit derived from a N-vinyl lactam is preferably 30 to 100 mol %, more preferably 50 to 100 mol %, still more preferably 70 to 100 mol %, further preferably 80 to 100 mol %, particularly preferably 90 to 100 mol %, most preferably 100 mol % in 100 mol % of all structural units (structural unit derived from N-vinyl lactam and structural unit derived from monomer (E)).

Here, all structural units do not include any structure derived from a crosslinkable monomer.

In the N-vinyl lactam-based crosslinked polymer, the proportion of the structural unit derived from a monomer (E) is preferably 0 to 70 mol %, more preferably 0 to 50 mol %, still more preferably 0 to 30 mol %, further preferably 0 to 20 mol %, particularly preferably 0 to 10 mol %, most preferably 0 mol % in 100 mol % of all structural units.

The N-vinyl lactam-based crosslinked polymer may optionally contain a structural unit derived from a crosslinkable monomer other than the cyanuric acid structure-containing crosslinkable monomer and/or a structural unit derived from a crosslinking agent. The ratio of the structural unit derived from a crosslinkable monomer and/or the structural unit derived from a crosslinking agent to 100 mol % of all structural units is preferably 0 to 2 mol %, more preferably 0 to 1 mol %, still more preferably 0 to 0.8 mol %.

The crosslinked polymer of the first aspect of the invention preferably has a water absorption capacity of 15 g or greater per 1 g of the N-vinyl lactam-based crosslinked polymer (15 times or more). The water absorption capacity is more preferably 18 g or greater, still more preferably 20 g or greater.

The crosslinked polymer of the first aspect of the invention preferably has an oil absorption capacity of 3 g or greater, more preferably 5 g or greater, still more preferably 10 g or greater, further more preferably 15 g or greater, most preferably 20 g or greater, per 1 g of the crosslinked polymer.

The water and oil absorption capacities are values calculated from "(weight of crosslinked polymer+amount of solution absorbed)/weight of crosslinked polymer". The liquid absorption capacity of the crosslinked polymer may be determined by the method described in the examples.

The crosslinked polymer of the first aspect of the invention preferably has a proportion of an extractable of 18 mass % or less in 100 mass % of the N-vinyl lactam-based crosslinked polymer.

The extractable means an uncrosslinked polymer fraction soluble in water. The amount of the extractable is determined as follows. The crosslinked polymer of the invention is stirred in deionized water (conductivity: 10 µS/cm or lower) in an amount about 100 times the amount of the crosslinked polymer for 16 hours at room temperature (temperature: 23±2° C.) and atmospheric pressure, the resulting mixture is filtered to obtain a liquid, and the amount of the extractable in the liquid was determined.

The N-vinyl lactam-based crosslinked polymer having a proportion of an extractable of 18 mass % or less in 100 mass % of the N-vinyl lactam-based crosslinked polymer has more sufficient gel-pulverizability. In this case, kneaders are particularly suitably used.

The N-vinyl lactam-based crosslinked polymer having a water absorption capacity of 15 times or more and having a proportion of an extractable of 18 mass % or less in 100 mass % of the N-vinyl lactam-based crosslinked polymer is another aspect of the invention. The proportion of an extractable is more preferably 17 mass % or less, still more preferably 16 mass % or less, further more preferably 15 mass % or less.

The N-vinyl lactam-based crosslinked polymer of the first aspect of the invention preferably has an average particle size of crosslinked polymer particles of 0.1 to 5000 µm. The crosslinked polymer particles having an average particle size of 0.1 to 5000 µm tend to have a higher absorption speed for water, for example. The crosslinked polymer particles having an average particle size of 0.1 µm or larger allow a more sufficient reduction of an extractable in the crosslinked polymer. The crosslinked polymer particles more preferably have an average particle size of 0.5 to 3000 µm, still more preferably 1 to 1000 µm.

The average particle size of the crosslinked polymer is a value measured using a dry particle size distribution analyzer (Model: Mastersizer 3000, dry type, product of Malvern in Spectris Co., Ltd.) or a particle size distribution analyzer using a laser diffraction-scattering method that has the same principle as this analyzer. In cases where the crosslinked polymer is in a rectangular compact form, the average particle size is a value measured with a ruler.

The N-vinyl lactam-based crosslinked polymer of the first aspect of the invention preferably contains particles having an aspect ratio of 1.15 to 10 in a proportion of 10% to 100% (by number) of the total number of the N-vinyl lactam-based crosslinked polymer particles. The proportion of the particles having an aspect ratio of 1.15 to 10 is preferably 30% to 100% (by number), still more preferably 50% to 100% (by number), further preferably 70% to 100% (by number), particularly preferably 90% to 100% (by number), most preferably 100% (by number).

The aspect ratio of the particles is preferably 1.15 to 7, more preferably 1.15 to 5, still more preferably 1.2 to 5, further preferably 1.2 to 3, further particularly preferably 1.25 to 3, most preferably 1.25 to 2.5.

The aspect ratio is determined by measuring the major and minor axes of primary particles of the cyclic N-vinyl lactam-based cross-linked polymer with a (optical or electron) microscope and dividing the major axis by the minor axis. In cases where the N-vinyl lactam-based crosslinked body particles form an aggregate, the aspect ratios of primary particles free from aggregation are measured. In cases where the primary particles overlap each other, the aspect ratios of particles free from overlapping are measured.

The aspect ratio is calculated by analyzing image data of a sample obtained from an optical or electron microscope using image analyzing particle size distribution measurement software. The aspect ratio may be measured with "image analyzing particle size distribution measurement software Mac-view ver. 4 (Mountech Co., Ltd.)", a "particle image analysis system Morphologi G3 (product of Malvern in Spectris Co., Ltd.)", or image analysis software or an image analysis system which has the same principle as these.

The proportion of the particles having an aspect ratio of 1.15 to 10 can be determined by measuring the aspect ratios of randomly selected 100 or more particles.

<Method of Producing N-Vinyl Lactam-Based Crosslinked Polymer of the First Aspect of the Invention>

The N-vinyl lactam-based crosslinked polymer of the first aspect of the invention may be produced by any method and is preferably produced by polymerizing a monomer component containing a N-vinyl lactam-based monomer and a cyanuric acid structure-containing crosslinkable monomer. That is, a method of producing a N-vinyl lactam-based crosslinked polymer including polymerizing a monomer component containing a N-vinyl lactam-based monomer and a cyanuric acid structure-containing crosslinkable monomer is also one aspect of the invention.

Specific examples and preferred examples of the monomer component are as described above.

The proportions of the N-vinyl lactam and the monomer (E) in 100 mol % of all monomer components (N-vinyl lactam and monomer (E)) are the same as those of the respective structural units in 100 mol % of all structural units.

The purity of the cyclic N-vinyl lactam monomer used in the polymerization is preferably 90% or higher, more preferably 95% or higher, further more preferably 98% or higher, most preferably 99% or higher.

The polymerization may be performed in the absence or presence of a solvent. Various conventionally known methods are available for the polymerization. Examples thereof include bulk polymerization, solution polymerization, suspension polymerization, inverse suspension polymerization, emulsion polymerization, inverse emulsion polymerization, precipitation polymerization, cast polymerization, thin-film polymerization, and spray polymerization.

A preferred polymerization method is solution polymerization. Solution polymerization allows prevention of uneven crosslinking in the crosslinked polymer.

Here, stirring in the polymerization reaction may be performed by any method. In cases where a gelled crosslinked polymer is formed, the crosslinked polymer is preferably stirred using a double-arm kneader as a stirring apparatus while it is fragmented by a shear force applied by the double-arm kneader. The polymerization may be performed in a batch wise or continuous manner.

The polymerization of the monomer component containing a N-vinyl lactam may be started by addition of a polymerization initiator, UV irradiation, application of heat, or light irradiation in the presence of a photo initiator.

In cases where the polymerization uses a solvent, examples of the solvent include water and alcohols such as methyl alcohol, ethyl alcohol, isopropyl alcohol, n-butyl alcohol, and diethylene glycol. One or two or more selected from these may be used. In terms of safety of the resulting composition, water is preferably used as a solvent. In this case, replacement of the solvent can be skipped, leading to an increase in productivity.

The polymerization preferably uses a polymerization initiator to perform polymerization. Suitable examples of the polymerization initiator include peroxides such as hydrogen peroxide and t-butyl hydroperoxide; persulfates such as sodium persulfate, potassium persulfate, and ammonium persulfate; azo compounds such as dimethyl 2,2'-azobis(2-methylpropionate), 2,2'-azobis(isobutyronitrile), 2,2'-azobis(2-methylbutyronitrile), 2,2'-azobis(2-methylpropionamidine) dihydrochloride, 2,2'-azobis[N-(2-carboxyethyl)-2-methylpropionamidine] hydrate, 2,2'-azobis[2-(2-imidazolin-2-yl)propane], 2,2'-azobis[2-(2-imidazolin-2-yl)propane] dihydrochloride, 2,2'-azobis[2-(2-imidazolin-2-yl)propane] disulfate hydrate, 2,2'-azobis(1-imino-1-pyrrolidino-2-methylpropane) dihydrochloride, 2,2'-azobis[N-(2-carboxyethyl)-2-methylpropionamidine] n-hydrate, and 2,2'-azobis[2-methyl-N-(2-hydroxyethyl)propionamide]; organic peroxides such as benzoyl peroxide, lauroyl peroxide, peracetic acid, di-t-butyl peroxide, and cumene hydroperoxide; and redox initiators that generate radicals by combining an oxidizing agent and a reducing agent, such as a combination of ascorbic acid and hydrogen peroxide, a combination of sodium sulfoxylate and t-butyl hydroperoxide, and a combination of a persulfate and a metal salt. Preferred among these polymerization initiators are hydrogen peroxide, persulfates, and azo compounds. The azo compounds are most preferred. More preferred among these are 2,2'-azobis[2-(2-imidazolin-2-yl)propane] dihydrochloride, 2,2'-azobis[2-(2-imidazolin-2-yl)propane], 2,2'-azobis[2-(2-imidazolin-2-yl)propane] disulfate hydrate, 2,2'-azobis(2-methylpropionamidine) dihydrochloride, and 2,2'-azobis(2-methylbutyronitrile). Each of these polymerization initiators may be used alone or two or more of these may be used as a mixture.

The polymerization initiator is preferably used in an amount of 0.1 g or more and 10 g or less per 1 mol of the monomers (the sum of the N-vinyl lactam, the cyanuric acid structure-containing crosslinkable monomer, the above-described monomer (E), and the crosslinkable monomer other than the cyanuric acid structure-containing crosslinkable monomer). The use of 0.1 g or more of the polymerization initiator allows a sufficient reduction of the proportion of an unreacted monomer contained in the resulting crosslinked polymer and allows a sufficient reduction of the amount of unreacted monomer-derived by-products such as a compound represented by the formula (3) below. The use of 10 g or less of the initiator allows a sufficient reduction of the proportion of impurities contained in the resulting crosslinked polymer. Also, the use of such an amount of the initiator allows prevention of discoloration of the resulting crosslinked polymer.

That is, a method of producing a N-vinyl lactam-based crosslinked polymer in which the polymerization uses a polymerization initiator in an amount of 0.1 to 10 g per 1 mol of the monomer component is also one aspect of the invention.

The amount of the polymerization initiator used is more preferably 0.1 g or more and 7 g or less, still more preferably 0.1 g or more and 5 g or less.

In cases where the polymerization uses inverse suspension polymerization, specific examples of a dispersant suitable for this case include sorbitan fatty acid esters, sucrose fatty acid esters, glycerol fatty acid esters, polyglycerol fatty acid esters, cellulose esters such as ethyl cellulose and cellulose acetate, cellulose ethers, and carboxyl group-containing polymers such as α-olefin-maleic anhydride copolymers. Each of these dispersants may be used alone, or two or more of these may be appropriately mixed and used. Here, any hydrophobic organic solvent may be used in inverse suspension polymerization.

The polymerization may be performed under any atmosphere and is preferably performed under inert gas (e.g., nitrogen, argon) atmosphere. The polymerization under inert gas atmosphere likely provides the following effects: the grinding efficiency of the resulting crosslinked polymer can be enhanced, the proportion of an unreacted monomer contained in the resulting crosslinked polymer can be reduced, and in the case of adding an organic acid to the crosslinked polymer, the reaction time of the organic acid with the crosslinked polymer can be shortened.

The polymerization may be performed at any temperature. The polymerization temperature is preferably relatively low because a crosslinked polymer with a great molecular weight can be obtained. The polymerization temperature is more preferably 20° C. to 100° C. because the polymerization rate is increased. Here, the reaction time to complete the polymerization reaction may appropriately be set depending on factors such as the reaction temperature, and the types (properties), combination, and amounts of a monomer component, a polymerization initiator, and a solvent.

A reaction vessel used for the polymerization may be made of any material usable for the polymerization. A reaction vessel made of stainless steel is preferred, for example. The use of such a reaction vessel made of a heat conductive material sufficiently proceeds the polymerization reaction, and can reduce the amount of an unreacted monomer (e.g., unsaturated monomer having a lactam structure) contained in the resulting crosslinked polymer.

Further, a reaction vessel made of a material that does not elute iron, such as polypropylene, is preferably used. The use of the reaction vessel made of such a material can reduce the iron content of the resulting crosslinked polymer.

The crosslinked polymer of the invention may be produced by a method including an optional step in addition to the polymerization. The production method may optionally include, for example, gel pulverization, drying, grinding, classification, granulation, and/or post-crosslinking.

In cases where the crosslinked polymer is a gelled polymer obtained by polymerization using a solvent, that is, a gelled crosslinked polymer containing a solvent, the production method preferably includes gel pulverization.

The gel pulverization may be performed by any method capable of converting the gelled crosslinked polymer containing a solvent into fine particles. For example, a pulverizing machine (e.g., kneader, meat chopper) may be used.

The crosslinked polymer is preferably produced by a method including drying.

In particular, in cases where the crosslinked polymer is a gelled polymer obtained by polymerization using a solvent, that is, a gelled crosslinked polymer containing a solvent, the production method preferably includes drying of the gelled crosslinked polymer or the particulate gelled crosslinked polymer obtained through the gel pulverization. In the first aspect of the invention, drying means an operation to increase the solid content and is usually performed to increase the solid content of the entire crosslinked polymer greater than that before drying. The solid content is preferably increased to 95 mass % or more, more preferably to 96 mass % or more in 100 mass % of the entire crosslinked polymer. The upper limit of the solid content is preferably about 99 mass %. The drying and polymerization may be carried out at the same time, and both drying during polymerization and drying after polymerization may be performed in combination. More preferably, drying is performed using a drying apparatus after polymerization. Here, the solid content of the crosslinked polymer is determined by the following method.

About 1 g of the crosslinked polymer is placed in a weighing bottle (mass: W1 (g)) having an about 5-cm diameter bottom face (mass: W2 (g)) and is dried by allowing it to stand in a constant temperature dryer at a temperature of 150° C. for one hour. The mass (W3 (g)) of the sum of the weighing bottle and the dried crosslinked polymer is measured, and the solid content is determined from the following equation:

$$\text{Solid content (mass \%)} = ((W3\ (g) - W1\ (g))/W2\ (g)) \times 100.$$

The drying is carried out at a temperature within the range of 80° C. to 250° C. preferably for 50% or more of the entire period of the drying, more preferably substantially throughout the drying. Within the above range, the physical properties of the crosslinked polymer tend to enhance.

The drying temperature is defined by the temperature of a heat medium. In the case of using, for example, microwave, that is, in cases where the drying temperature cannot be defined by the temperature of a heat medium, the drying temperature is defined by a material temperature. The drying may be performed by any method carried out at a temperature within the above range and may suitably be performed by hot air drying, no-wind drying, reduced-pressure drying, infrared drying, or microwave drying, for example. Preferred among these is hot air drying. In the hot air drying, the drying airflow is preferably within the range of 0.01 to 10 m/sec, more preferably within the range of 0.1 to 5 m/sec. The drying temperature is more preferably within the range of 110° C. to 220° C., still more preferably within the range of 120° C. to 200° C. The drying may be carried out at a fixed temperature or at varying temperatures. Substantially, the entire drying is preferably carried out within the above temperature ranges.

The production method preferably includes grinding. The grinding can provide a crosslinked polymer having a more suitable average particle size and a more suitable aspect ratio.

In the case of the production method of the invention including drying, the grinding may be performed before, during, or after the drying, preferably after the drying. More preferably, the grinding is performed after the gel pulverization and the drying.

The grinding preferably uses a grinder. Examples of the grinder to be used include, but are not limited to, a roll grinder such as a roll mill, a hammer grinder such as a hammer mill, an impact grinder, a cutter mill, a turbo grinder, a ball mill, a pin mill, a flash mill, and a jet mill such as a fluidized-bed jet mill or a target jet mill. A target jet mill is preferably used to grind the polymer into particles having a smaller average particle size. The particle size distribution is preferably controlled by using a roll mill, a hammer grinder, an impact grinder, a pin mill, or a jet mill. The particle size distribution is preferably controlled by performing grinding two times or more continuously, more preferably performing grinding three times or more continuously.

The two or more grinding operations may use the same grinder or different grinders. Different grinders may be used in combination.

The grinding may be performed by any grinding method and may be performed at room temperature or by freeze grinding. The N-vinyl lactam-based crosslinked polymer, which is soft, is preferably ground by freeze grinding. The use of a target jet mill is capable of more finely grinding the polymer even at room temperature. Thereby, the production cost can be more reduced than the production cost in the case of freeze grinding. In addition, classification described below can be omitted by using a target jet mill. Thereby, the productivity can be more increased.

In order to obtain the crosslinked polymer of the invention having an average particle size within a more suitable range and/or a specific particle size distribution, for example, the production method may include classification or granulation. The classification may use a sieve with a specific mesh size. Any classifier may be used for classification using a sieve. Examples of the classifier include, but are not limited to, a vibration sieve (e.g., unbalanced weight-driven type, resonant type, vibrating motor type, electromagnetic type, and circular vibration type), an in-plane motion sieve (e.g., horizontal motion type, horizontal circle-linear motion type, and three-dimensional circle motion type), a movable net sieve, a compulsory stirring sieve, a net plane vibration sieve, a wind force sieve, and a sonic sieve. Preferred are a vibration sieve and an in-plane motion sieve.

In cases where the crosslinked polymer has a crosslinked structure formed by any of the processes (2) to (5), the method of producing the crosslinked polymer includes post-crosslinking of forming the crosslinked structure after the polymerization of a monomer component.

Examples of the method of post-crosslinking (crosslinking after polymerization) include (i) a method of applying UV, γ rays, or an electron beam to the polymer obtained in the polymerization, (ii) a method of self-crosslinking the polymer obtained in the polymerization in the presence of a reaction accelerator such as a condensing agent, (iii) a method of self-crosslinking the polymer obtained in the polymerization by application of heat, (iv) a method of introducing a radical generating agent into the polymer obtained in the polymerization and self-crosslinking the polymer by application of heat, and (v) a method of introducing a radical polymerizable crosslinking agent (crosslinkable monomer) and a radical polymerization initiator into the polymer obtained in the polymerization and applying heat and/or light to the polymer.

In cases where the crosslinked polymer of the invention has a crosslinked structure formed by the process (2), the crosslinking agent is preferably used in such an amount that the ratio of the functional group of the crosslinking agent to 100 mol % of the reactive functional group (reactive functional group reactive with the crosslinking agent) of the polymer is 30 to 100 mol %, more preferably 50 to 100 mol %. The use of the crosslinking agent in such a ratio allows sufficient formation of the crosslinked structure and can reduce the amount of an unreacted crosslinking agent remaining in the resulting crosslinked polymer.

Examples of the reaction accelerator used in the method (ii) include acids such as sulfuric acid and phosphoric acid; bases such as sodium hydroxide and potassium hydroxide; and condensing agents such as N,N'-dicyclohexyl carbodiimide. One or two or more of these may be used.

The radical generating agent used in the method (iv) may be the same as the polymerization initiator used in the above-described polymerization. Preferred among the polymerization initiators are peroxides such as hydrogen peroxide, t-butyl hydroperoxide, t-butyl peroxypivalate, octanoyl peroxide, succinic peroxide, t-hexyl peroxy-2-ethylhexanoate, t-butyl peroxy-2-ethylhexanoate, t-butyl peroxyisobutyrate, and t-butyl peroxy maleic acid.

In cases where the crosslinked polymer of the invention has a crosslinked structure formed by the process (5), the amount of the crosslinkable monomer used in the post-crosslinking is preferably 0.1 to 50 mass %, more preferably 1 to 30 mass % relative to 100 mass % of the polymer before the post-crosslinking. The use of the crosslinkable monomer in such a ratio allows sufficient formation of the crosslinked structure and can reduce the amount of an unreacted crosslinkable monomer remaining in the resulting crosslinked polymer.

The production of the crosslinked polymer preferably includes adding an organic acid to the resulting crosslinked polymer after the polymerization reaction. The addition of an organic acid to the resulting crosslinked polymer can reduce the amount of the N-vinyl lactam-based monomer remaining in the crosslinked polymer.

Examples of the organic acid include, but are not limited to, organic compounds having an acid group such as a carboxyl group, a sulfonic group, a phosphoric group, a sulfuric group, or a phosphoric group. Specific examples of such organic acids include malonic acid, oxalic acid, succinic acid, aspartic acid, citric acid, glutamic acid, fumaric acid, malic acid, maleic acid, phthalic acid, trimellitic acid, pyromellitic acid, propionic acid, heptanoic acid, octanoic acid, glycolic acid, salicylic acid, lactic acid, L-ascorbic acid, benzoic acid, methanesulfonic acid, benzenesulfonic acid, laurylbeneznesulfonic acid, p-toluenesulfonic acid, benzenephosphonic acid, and laurylsulfonic acid.

The organic acid may be used in any amount, and the amount thereof is preferably 0.01 to 5 mass % relative to 100 mass % of the N-vinyl lactam-based monomer added in the reaction step. The use of the organic acid in an amount within the above range can reduce the amount of the N-vinyl lactam-based monomer remaining in the resulting polymer and can reduce the amount of the organic acid (salt). The amount of the organic acid is more preferably 0.05 to 3 mass %, still more preferably 0.1 to 1 mass %.

The organic acid (salt) indicates the organic acid and a salt of the organic acid. The salt of the organic acid indicates a neutralized product of the organic acid and a base to be added in the neutralization described below.

In the case of adding the organic acid to the crosslinked polymer, the organic acid and the crosslinked polymer may be reacted with each other for any period of time. The reaction time is preferably 10 minutes to 3 hours, more preferably 30 minutes to 2 hours.

The method of producing the crosslinked polymer preferably includes aging of the crosslinked polymer after the polymerization reaction. The aging can reduce the amount of the residual N-vinyl lactam-based monomer and can reduce the amount of a by-product derived from the residual N-vinyl lactam-based monomer, such as a compound represented by the formula (3) described below. The temperature of the aging is preferably, but is not limited to, 70° C. to 150° C. At the aging temperature within the above range, the amount of the residual N-vinyl lactam-based monomer can be more sufficiently reduced. The aging temperature is more preferably 80° C. to 100° C.

The aging time in the aging is preferably, but is not limited to, 10 minutes to 5 hours, more preferably 30 minutes to 3 hours.

In the case of the method of producing the crosslinked polymer including adding an organic acid, the aging is preferably performed before adding an organic acid.

The aging is preferably performed while the crosslinked polymer is pulverized. In the case of the method including the adding an organic acid, the pulverization allows the organic acid to sufficiently permeate the pulverized crosslinked polymer. Thus, the amount of the N-vinyl lactam-based monomer remaining in the crosslinked polymer can be more sufficiently reduced. The crosslinked polymer may be pulverized by a common method and may be pulverized by a method using a screw extruder such as a kneader or a meat chopper, or a gel grinder such as a cutter mill, for example.

In the case of adding an organic acid, the method of producing the crosslinked polymer preferably includes neutralization after the adding an organic acid. The neutralization may be performed by any method and is preferably performed by adding a base after the reaction of the organic acid with the polymer. Examples of the base include, but are not limited to, ammonia; aliphatic amines such as monoethanolamine, diethanolamine, and triethanolamine; aromatic amines such as aniline; and alkali metal hydroxides such as sodium hydroxide and potassium hydroxide. Each of these may be used alone, or two or more of these may be used in combination. Preferred among these are ammonia, aliphatic amines, and alkali metal hydroxides, and more preferred are ammonia, monoethanolamine, diethanolamine, sodium hydroxide, and potassium hydroxide.

The N-vinyl lactam-based crosslinked polymer-containing composition of the invention contains the N-vinyl lactam-based crosslinked polymer, and the composition may contain any amount of the N-vinyl lactam-based crosslinked polymer. The amount of the N-vinyl lactam-based crosslinked polymer is preferably 50 to 100 mass %, more preferably 60 to 100 mass %, still more preferably 70 to 100 mass % relative to 100 mass % of the composition.

The N-vinyl lactam-based crosslinked polymer-containing composition may optionally contain a different component other than the crosslinked polymer. Examples of the different component include, but are not limited to, an extractable (uncrosslinked polymer fraction soluble in water), polymerization initiator residues, residual monomers, by-products in the polymerization, and water. The composition may contain one or two or more of these.

The N-vinyl lactam-based crosslinked polymer-containing composition may optionally contain as a by-product of the polymerization a compound represented by the following formula (3):

[Chem. 3]

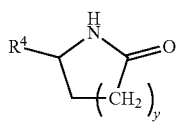

(3)

wherein $R^4$ represents a hydrogen atom or an optionally substituted C1-C10 alkyl group; and y represents an integer of 1 to 3. The composition preferably has a proportion of the compound of 2 mass % or less in 100 mass % of the N-vinyl lactam-based crosslinked polymer. At a proportion of the compound represented by the formula (3) of 2 mass % or less, odor and/or discoloration of the composition can be sufficiently prevented. Thus, the composition is suitable for cosmetic applications.

That is, the N-vinyl lactam-based crosslinked polymer-containing composition having a proportion of a compound represented by the formula (3) of 2 mass % or less in 100 mass % of the N-vinyl lactam-based crosslinked polymer is also one aspect of the invention. The proportion of the compound represented by the formula (3) is more preferably 1.5 mass % or less, still more preferably 1 mass % or less.

The proportion of the compound represented by the formula (3) in the composition is determined by the method described in the examples.

$R^4$ and y in the formula (3) are the same as $R^4$ and y in the formula (2).

The composition having a proportion of the residual monomer such as the N-vinyl lactam-based monomer of preferably 200 ppm or less in 100 mass % of the N-vinyl lactam-based crosslinked polymer. The composition having a proportion of the residual monomer within the above range is more highly safe as a cosmetic. The proportion of the residual monomer is more preferably 100 ppm or less, still more preferably 50 ppm or less.

The proportion of the residual monomer in the composition may be determined by the method described in the examples.

The N-vinyl lactam-based crosslinked polymer and/or the N-vinyl lactam-based crosslinked polymer-containing composition of the invention can be used in applications such as an ink absorbing agent for use in writing instruments and ink jet recording apparatuses, deodorants, fragrance agents, and cosmetics.

An ink absorbing agent including the N-vinyl lactam-based crosslinked polymer or the N-vinyl lactam-based crosslinked polymer-containing composition of the invention is also one aspect of the invention.

The invention also relates to an ink-containing composition including the N-vinyl lactam-based crosslinked polymer of the invention and ink absorbed by the polymer.

The invention also relates to an ink-containing composition including the ink absorbing agent and ink absorbed by the agent.

The invention also relates to an absorbent material including the ink absorbing agent.

The invention also relates to a printer including the ink absorbing agent.

The invention also relates to a method of using the ink absorbing agent, the ink absorbing agent being incorporated into a printer.

The printer may be any apparatus that prints using ink mounted in the printer. Examples of the printer include an ink-jet printer, an offset printer, and a gravure printer.

Examples of the components of the ink include, but are not limited to, water, water-soluble organic solvents, dyes, pigments, and other additives.

Examples of the water-soluble organic solvents include glycerol and glycols such as ethylene glycol and diethylene glycol.

Examples of the dyes include black azo compounds, copper phthalocyanine compounds, and magenta dyes.

Examples of the pigments include inorganic pigments such as carbon black and metal oxides and organic pigments such as azo pigments and phthalocyanine pigments. The pigments may have any particle size, and the particle size is preferably 0.01 to 0.50 μm, more preferably 0.02 to 0.20 μm.

The invention also relates to a deodorant containing the N-vinyl lactam-based crosslinked polymer or N-vinyl lactam-based crosslinked polymer-containing composition of the invention.

The deodorant may be effective against any odor component and is effective against, for example, thiols such as methyl mercaptan, amines such as ammonia, carboxylic acids such as acetic acid, aldehydes such as nonenal, and diketones such as diacetyl. That is, the N-vinyl lactam-based crosslinked polymer of the invention can exhibit a deodorizing effect against various odor components. The reason for this is considered as follows. The crosslinked polymer of the invention is capable of absorbing odor components at a N site or a carbonyl group of the N-vinyl lactam-derived lactam ring, and the crosslinked polymer of the invention has moisture absorbency and thus is capable of absorbing water-soluble odor components through moisture absorbed thereby. The crosslinked polymer of the invention exhibits a better deodorizing effect against carboxylic acids such as acetic acid among the above odor components.

The deodorant may be in any form, and may be in the form of liquid, gel, paste, powder, or solid.

The invention also relates to a deodorizer including the deodorant.

Examples of the deodorizer include, but are not limited to, a deodorizer including the deodorant of the invention and a vent and a deodorizer having a mechanism that draws the deodorant of the invention and the air.

The invention also relates to a method of using the deodorant, the deodorant being incorporated into a deodorizer.

For example, the deodorant is used in such a way that the air to be deodorized is brought into contact with the deodorant of the invention.

Examples of the method of bringing the deodorant into contact with the air include: a method in which the air is brought into contact with the deodorant of the invention by natural convection flow using a deodorizer including the deodorant of the invention and a vent; and a method in which the air is drawn and supplied to the deodorant of the invention to be brought into contact with the deodorant of the invention using a deodorizer or the like including the deodorant of the invention and an air suction system.

Examples of the air suction system of the deodorizer include, but are not limited to, a fan and an air pump.

Examples of the deodorizer including the deodorant of the invention and an air suction system include, but are not limited to, an air purifier and an air conditioner. In cases where the deodorant of the invention is used in an air purifier or an air conditioner, for example, the deodorant is preferably used in a filter or a rotating member such as a fan.

The invention also relates to a fragrance agent containing the N-vinyl lactam-based crosslinked polymer of the invention and a fragrance component. Preferred examples of the fragrance component include, but are not limited to, components with volatility, such as perfumes and essential oils.

A cosmetic containing the N-vinyl lactam-based crosslinked polymer of the invention and/or the N-vinyl lactam-based crosslinked polymer-containing composition of the invention is also one aspect of the invention.

A method of using the N-vinyl lactam-based crosslinked polymer of the invention and/or the N-vinyl lactam-based crosslinked polymer-containing composition of the invention as a cosmetic is also one aspect of the invention.

The cosmetic may optionally contain a different component other than the N-vinyl lactam-based crosslinked polymer and/or the N-vinyl lactam-based crosslinked polymer-containing composition. Examples of the different component include, but are not limited to, an oily base, a moisturizing agent, a touch improving agent, a surfactant, a polymer, a thickening agent, a gelling agent, a solvent, a propellant, an antioxidant, a reductant, an oxidant, a preservative, an antibacterial agent, a chelating agent, a pH adjusting agent, an acid, an alkali, a powder, an inorganic salt, an ultraviolet absorbent, a whitening agent, vitamins and derivatives thereof, an antiphlogistic agent, an antiinflammatory agent, a drug for hair growth, a blood circulation accelerator, a stimulant, hormone, an antiwrinkle agent, an antiaging agent, a tightening agent, a cold sense agent, a warm sense agent, a wound healing accelerator, an irritation alleviating agent, an analgesic, a cell activator, plant extract, animal extract, microbial extract, an antipruritic agent, a keratin releasing and dissolving agent, an antiperspirant, a cooling agent, an astringent, enzyme, nucleic acid, fragrances, a coloring matter, a colorant, a dye, a pigment, and water.

For other specific examples of the different monomer, the components disclosed in JP 2007-45776 A may also be used.

The cosmetic of the invention may be produced by any method. The method preferably includes, for example, mixing the crosslinked polymer with any of the above different components.

The mixing may be performed by any technique. For example, preferably, the crosslinked polymer in the form of a dispersion in a solvent such as water is mixed with the different component.

The dispersion of the crosslinked polymer is preferably treated with a wet type super atomizer ("NanoVater", Yoshida Kikai Co., Ltd.) or a stirring and mixing apparatus ("Damatori system", Yoshida Kikai Co., Ltd.), or a wet type super atomizer or a stirring and mixing apparatus having the same principles as those before mixing with the different component. Such treatment allows sufficient disintegration of gel aggregation in the cosmetic, leading to enhancement of the viscosity stability of the cosmetic.

Examples of the cosmetic of the invention include, but are not limited to, skin cosmetics, skin preparations for external use, and hair cosmetics. The crosslinked body in the cosmetic of the invention exerts the effects as a moisturizer, a thickening agent, an oil-absorbing agent, or other agents in such cosmetics. The invention also relates to a moisturizer, a thickening agent, or an oil-absorbing agent, each containing the cyclic N-vinyl lactam-based crosslinked body in the invention.

Examples of the skin cosmetics include, but are not limited to, basic cosmetics such as skin lotion, cream, milky lotion, and serum; makeup cosmetics such as liquid foundation, base milky lotion, cheek color, eye shadow, mascara, and lipstick; cleansing cosmetics such as cleansing cream, cleansing foam, and liquid cleansers; cosmetics (including quasi-drugs) such as sunscreen cosmetics; and bath cosmetics such as bath agents. Examples of skin preparations for external use include external preparations such as liniments, lotions, and ointments. Examples of hair cosmetics include, but are not limited to, shampoo, rinse, conditioner, wax, spray, gel, and mist.

The invention also relates to a skin cosmetic, a skin preparation for external use, or a hair cosmetic, each containing the crosslinked polymer of the invention.

<Second Aspect of the Invention: N-Vinyl Lactam-Based Crosslinked Polymer>

The following describes the technical features of the second aspect of the invention different from those of the first aspect of the invention.

The N-vinyl lactam-based crosslinked polymer of the second aspect of the invention (hereinafter, also referred to as crosslinked polymer of the second aspect of the invention) includes a structural unit derived from a N-vinyl lactam.

The crosslinked polymer of the second aspect of the invention including a structural unit derived from a N-vinyl lactam is capable of absorbing, retaining, or slowly releasing water and/or oil. Thus, the crosslinked polymer can exert a moisturizing effect. In addition, the crosslinked polymer capable of absorbing oil can also exert an effect as an oil-absorbing agent. Further, the crosslinked polymer of the invention having a crosslinked structure swells into a gel when the polymer absorbs water or other solvents. Therefore, the polymer exerts a thickening effect and further enhances the adhesiveness to the skin of a cosmetic containing the polymer.

Since the N-vinyl lactam has nonionic properties, the crosslinked polymer of the invention including a structural unit derived from a N-vinyl lactam is highly safe and suitable for cosmetic applications. Further, the crosslinked polymer of the invention including a structural unit derived from a N-vinyl lactam has an excellent deodorizing ability for odor components. The excellent deodorizing ability herein means a high effect of reducing at least one of the amount and the concentration of an odor component.

The crosslinked polymer of the second aspect of the invention has an ethanol absorption capacity of 3 to 40 g per 1 g of the N-vinyl lactam-based crosslinked polymer. Thus, the crosslinked polymer is suitable for cosmetic applications. The ethanol absorption capacity is preferably 5 g or greater, more preferably 8 g or greater, still more preferably 10 g or greater, still further more preferably 12 g or greater, particularly preferably 15 g or greater, most preferably 20 g or greater. Meanwhile, the upper limit of the ethanol absorption capacity is preferably high, but is more preferably 35 g or less, still more preferably 30 g or less.

The crosslinked polymer of the second aspect of the invention has a water absorption capacity of 3 to 40 g per 1 g of the N-vinyl lactam-based crosslinked polymer. The water absorption capacity is preferably 5 g or greater, more preferably 8 g or greater, still more preferably 10 g or greater, still further more preferably 12 g or greater, particularly preferably 15 g or greater, most preferably 20 g or greater. Meanwhile, the upper limit of the water absorption capacity is preferably high, but is more preferably 35 g or less, still more preferably 30 g or less.

The crosslinked polymer of the second aspect of the invention preferably has an oil absorption capacity of 3 g or greater, more preferably 5 g or greater, more preferably 8 g or greater, still more preferably 10 g or greater, still further more preferably 12 g or greater, particularly preferably 15 g or greater, most preferably 20 g or greater, per 1 g of the crosslinked polymer. Meanwhile, the upper limit of the oil absorption capacity is preferably high, but is more preferably 60 g or less, still more preferably 50 g or less, most preferably 40 g or less.

The ethanol, water, and oil absorption capacities are values calculated from "(weight of crosslinked polymer+ amount of solution absorbed)/weight of crosslinked polymer". The liquid absorption capacity of the crosslinked polymer may be determined by the method described in the examples.

For cosmetic product applications, the N-vinyl lactam-based crosslinked polymer of the second aspect of the invention preferably has an average particle size of crosslinked polymer particles of 0.1 to 100 μm, more preferably 0.1 to 80 μm, still more preferably 1 to 40 μm. The crosslinked polymer particles having an average particle size of 1 to 40 μm are preferred because such polymer particles are capable of sufficiently suppressing grainy texture on the skin to which they are applied as a cosmetic, leading to good touch. Further, the absorption speed for, for example, water tends to be enhanced. The crosslinked polymer particles more preferably have an average particle size of 1 to 30 μm, still further more preferably 1 to 20 μm, particularly preferably 1 to 10 μm.

The average particle size of the crosslinked polymer may be measured using a dry particle size distribution analyzer (Model: Mastersizer 3000, dry type, product of Malvern in Spectris Co., Ltd.) or a particle size distribution analyzer using a laser diffraction-scattering method that has the same principle as this.

The N-vinyl lactam-based crosslinked polymer of the invention contains particles having an aspect ratio determined by the method described above of 1.15 to 10 in a proportion of 10% to 100% (by number) of the total number of the N-vinyl lactam-based crosslinked polymer. Particles having such a shape have a larger contact area with the skin than spherical particles and are thus excellent in adhesiveness to the skin and easy to stay on the surface of the skin.

The measurement method and measurement apparatus for the aspect ratio are the same as those described for the first aspect of the invention.

The proportion of the particles having an aspect ratio of 1.15 to 10 is preferably 30% to 100% (by number), more preferably 50% to 100% (by number), further preferably 70% to 100% (by number), particularly preferably 90% to 100% (by number), most preferably 100% (by number).

The aspect ratio of the particles is preferably 1.15 to 7, more preferably 1.15 to 5, still more preferably 1.2 to 5, particularly preferably 1.2 to 3, further particularly preferably 1.25 to 3, most preferably 1.25 to 2.5.

The average aspect ratio of randomly selected 100 or more particles of the cyclic N-vinyl lactam-based crosslinked body is preferably 1.15 to 5, more preferably 1.15 to 3, still more preferably 1.2 to 3, particularly preferably 1.2 to 2.5, most preferably 1.2 to 2.

The crosslinked structure of the crosslinked polymer of the second aspect of the invention may include a crosslinked structure other than the structural unit derived from a crosslinkable monomer. The crosslinked structure can be formed by any of the following processes (6) to (10), for example.

(6) A monomer component containing a crosslinkable monomer is polymerized to produce a polymer having a crosslinked structure.

(7) A monomer component containing a reactive functional group-containing monomer is polymerized to obtain a polymer, and the polymer is reacted with a crosslinking agent having multiple functional groups capable of reacting with the reactive functional group to form a crosslinked structure.

(8) A monomer component containing a monomer 1 having a reactive functional group and a monomer 2 having a reactive functional group capable of reacting with the reactive functional group of the monomer 1 is polymerized, and then the reactive functional group of the monomer 1 is reacted with the reactive functional group of the monomer 2 to form a crosslinked structure (self-crosslinking).

(9) Radicals are produced in polymers, and a crosslinked structure is formed between the polymers containing radicals (self-crosslinking).

(10) Radicals are produced in a polymer, and the polymer containing radicals is reacted with a crosslinkable monomer to form a crosslinked structure.

Specific examples of the crosslinkable monomer are the same as those described for the first aspect of the invention.

The crosslinked structure of the crosslinked polymer of the second aspect of the invention may be formed by any of the processes (6) to (10). The crosslinked structure formed by the process (6) is preferred.

Preferred among the crosslinkable monomers in the processes (6) and (10) are compounds having at least two allyl groups because the use of such compounds tends to reduce a residual N-vinyl lactam and an extractable (uncrosslinked polymer fraction soluble in water). Specifically, preferred are cyanuric acid structure-containing crosslinkable monomers such as triallyl cyanurate; pentaerythritol (di, tri, or tetra) (meth)allyl ethers, triallyl isocyanurate, triallyl phosphate, triallylamine, diallyl carbonate, 1,3-bis(allyloxy)-2-propanol, divinylethylene urea, 1,4-butylene bis(N-vinylamide), and (di, tri, tetra, penta, hexa, hepta, or octa)allyl sucrose.

More preferred are triallyl cyanurate, pentaerythritol (di, tri, or tetra)allyl ethers and (di, tri, tetra, penta, hexa, hepta, or octa)allyl sucrose. A N-vinyl lactam-based crosslinked polymer including a structural unit derived from triallyl cyanurate, a pentaerythritol (di, tri, or tetra)allyl ether, or (di, tri, tetra, penta, hexa, hepta, or octa)allyl sucrose is one preferred embodiment of the invention. Such a crosslinked polymer is more suitable for cosmetic applications because pentaerythritol (di, tri, or tetra)allyl ethers and (di, tri, tetra, penta, hexa, hepta, or octa)allyl sucrose are highly safe.

The N-vinyl lactam-based crosslinked polymer includes: a structural unit derived from a N-vinyl lactam-based monomer; and a structural unit derived from a crosslinkable monomer and/or a structural unit derived from a crosslinking agent. The ratio of the structural unit derived from a crosslinkable monomer and/or the structural unit derived from a crosslinking agent is preferably 0.01 to 2 mol % to 100 mol % of all structural units. The crosslinked polymer containing the structural unit derived from a crosslinkable monomer and/or the structural unit derived from a crosslinking agent in a ratio of 0.01 to 2 mol % has a gel strength within a more suitable range. Thus, the crosslinked polymer has more sufficient gel-pulverizability into particles having a smaller average particle size. Further, the absorbent or retention capacity for solvents such as water of the crosslinked polymer of the invention can be controlled by controlling the ratio of the structural unit derived from a crosslinkable monomer and/or the structural unit derived from a crosslinking agent.

The ratio is more preferably 0.05 to 1.5 mol %, still more preferably 0.06 to 1.4 mol %, further preferably 0.08 to 1.2 mol %, further more preferably 0.1 to 1 mol %.

In the case of the crosslinked polymer including a structural unit derived from a cyanuric acid structure-containing crosslinkable monomer, the ratio of the structural unit is preferably 0.05 to 1.5 mol %, still more preferably 0.06 to 1.4 mol %, further preferably 0.08 to 1.2 mol %, further more preferably 0.1 to 1 mol %, still further more preferably 0.12 to 0.8 mol %, particularly preferably 0.12 to 0.6 mol %, most preferably 0.12 to 0.48 mol %.

In the case of the N-vinyl lactam-based crosslinked polymer including a structural unit derived from a crosslinkable monomer, the ratio of the structural unit is preferably 0.01 to 2 mol %, more preferably 0.1 to 1 mol % to 100 mol % of all structural units.

The N-vinyl lactam-based crosslinked polymer of the second aspect of the invention has a proportion of an extractable of 35 mass % or less in 100 mass % of the N-vinyl lactam-based crosslinked polymer. The use of such a polymer in intended applications increases the concentration of an effective component therein. Such a crosslinked polymer used as a cosmetic has excellent moisturizing and oil-absorbing effects, and sufficiently allows prevention of an increase in viscosity of the cosmetic.

The proportion of the extractable is more preferably 30 mass % or less, still more preferably 25 mass % or less.

The proportion of the extractable in the composition may be determined by the method described in the examples.

The N-vinyl lactam-based crosslinked polymer preferably has a viscosity of 100 mPa·s or higher and lower than 10000 mPa·s in the form of a 5 mass % aqueous dispersion of the crosslinked polymer. The crosslinked polymer with such a viscosity can have favorable applicability to the skin as a cosmetic.

That is, it is also a preferred embodiment of the invention that the N-vinyl lactam-based crosslinked polymer has a viscosity measured under the following conditions of 100 mPa·s or higher and lower than 10000 mPa·s.

<Viscosity Measurement Conditions>

Sample: A 5 mass % aqueous dispersion of the N-vinyl lactam-based crosslinked polymer after 16-hour stirring Measuring equipment: The sample is measured using a B-type viscometer at 25° C.

Measurement conditions: Rotor No. 4, rotation speed: 30 rpm

The viscosity is preferably 500 mPa·s or higher and lower than 10000 mPa·s, more preferably 1000 mPa·s or higher and lower than 10000 mPa·s, still more preferably 3000 mPa·s or higher and 9000 mPa·s or lower, particularly preferably 5000 mPa·s or higher and 9000 mPa·s or lower, particularly further preferably 7000 mPa·s or higher and 9000 mPa·s or lower.

The viscosity can be determined by the following method.

<Measurement of Viscosity>

A 50-mL glass screw tube is charged with 2.5 g of a particulate crosslinked polymer and 47.5 g of deionized water (conductivity: 10 μS/cm or lower), which are precisely weighed. A stirrer bar is placed in the tube, and the tube is sealed. These operations are performed in a room at a temperature of 23±2° C., a relative humidity of 50±5%, and atmospheric pressure. Thereafter, the contents are stirred using a magnetic stirrer for 16 hours at room temperature (temperature: 23±2° C.) and atmospheric pressure to prepare a 5 mass % aqueous dispersion of the cyclic N-vinyl lactam-based crosslinked body. Subsequently, the temperature of the aqueous solution is set at 25° C., and the viscosity is measured using a B-type viscometer (BM type, Toki Sangyo Co., Ltd.) (Rotor No. 4, rotation speed: 30 rpm).

<Method of Producing N-Vinyl Lactam-Based Crosslinked Polymer of the Second Aspect of the Invention>

The N-vinyl lactam-based crosslinked polymer of the second aspect of the invention may be produced by any method and is preferably produced by polymerizing a monomer component containing a N-vinyl lactam-based monomer and forming a crosslinked structure. That is, a method of producing a N-vinyl lactam-based crosslinked polymer including polymerizing a monomer component containing a N-vinyl lactam-based monomer and forming a crosslinked structure is also one aspect of the invention.

Specific examples and preferred examples of the monomer component are as described above. The proportion of the N-vinyl lactam, the proportion of the monomer (E), and the ratio of the crosslinkable monomer to 100 mol % of all monomer components (N-vinyl lactam and monomer (E)) are the same as the proportion of the structural unit derived from a N-vinyl lactam, the proportion of the structural unit derived from a monomer (E), and the ratio of the structural unit derived from a crosslinkable monomer to 100 mol % of all structural units.

When the crosslinked structure is formed using the crosslinkable monomer, the polymerization and the formation of the crosslinked structure are performed at the same time. Such an embodiment is also a preferred embodiment of the invention.

The polymerization reaction in the polymerization may be performed at any pH and is preferably performed at a pH of 5 to 10. The polymerization reaction at a pH within the range of 5 to 10 allows prevention of the hydrolysis of the N-vinyl lactam-based monomer and can reduce the amount of a by-product derived from a residual N-vinyl lactam-based monomer, such as a compound represented by the formula (3) described above. The pH during the polymerization reaction is more preferably 7 to 9. The pH may be controlled by any method. Preferably, the pH of the solution of the monomer component to be used is controlled using an acid or a base before addition to a reaction vessel.

In cases where the crosslinked polymer of the invention has a crosslinked structure formed by any of the processes (7) to (10), the method of producing the crosslinked polymer includes post-crosslinking of forming the crosslinked structure after the polymerizing a monomer component.

The post-crosslinking may use a polymer produced from a monomer component or a commercially available polymer.

The N-vinyl lactam-based crosslinked polymer-containing composition of the second aspect of the invention contains the N-vinyl lactam-based crosslinked polymer, and the amount of the N-vinyl lactam-based crosslinked polymer in the composition and a different component other than the crosslinked polymer are the same as those for the N-vinyl lactam-based crosslinked polymer-containing composition of the first aspect of the invention.

The N-vinyl lactam-based crosslinked polymer-containing composition preferably has a proportion of an extractable of 35 mass % or less in 100 mass % of the N-vinyl lactam-based crosslinked polymer. With a proportion of an extractable within the above preferred range, the concentration of an effective component in the composition can more increase, and the composition can have better moisturizing and oil-absorbing effects when it is used as a cosmetic and more sufficiently allows prevention of an increase in viscosity of a cosmetic.

That is, the N-vinyl lactam-based crosslinked polymer-containing composition having a proportion of an extractable of 35 mass % or less in 100 mass % of the N-vinyl lactam-based crosslinked polymer is also one aspect of the invention. The proportion of the extractable is more preferably 30% or less, still more preferably 25% or less.

The proportion of the extractable in the composition may be determined by the method described in the examples.

The N-vinyl lactam-based crosslinked polymer of the invention also has an excellent deodorizing ability for odor components, and thus is suitable for deodorant applications. That is, the N-vinyl lactam-based crosslinked polymer can be suitably used as a deodorant, and a deodorant containing the N-vinyl lactam-based crosslinked polymer of the invention is also one aspect of the invention.

<Third Aspect of the Invention: Cosmetic>

The following describes the technical features of the third aspect of the invention different from those of the first and second aspects of the invention.

The matters referring to "the third aspect of the invention" herein are common to the first and second embodiments of the third aspect of the invention.

The cosmetic of the third aspect of the invention contains a cyclic N-vinyl lactam-based crosslinked polymer (hereinafter, also referred to as crosslinked polymer in the third aspect of the invention) including a structural unit derived from a cyclic N-vinyl lactam.

Ionic polymers often have skin irritation and corrosiveness and are poor in safety. On the other hand, a cyclic N-vinyl lactam has nonionic properties and the crosslinked polymer in the third aspect of the invention including a structural unit derived from a cyclic N-vinyl lactam is safer than conventional additives and suitable for cosmetic applications.

Further, the crosslinked polymer in the third aspect of the invention including a structural unit derived from a cyclic N-vinyl lactam is capable of absorbing, retaining, or releasing water and/or oil. Thus, the crosslinked polymer can exert a moisturizing effect. In addition, the crosslinked polymer capable of absorbing oil can also exert an effect as an oil-absorbing agent. Further, the crosslinked polymer in the invention having a crosslinked structure swells into a gel when the polymer absorbs water or other solvents. Therefore, the polymer exerts a thickening effect and further enhances the adhesiveness to the skin of a cosmetic containing the polymer.

The cyclic N-vinyl lactam-based crosslinked body in the first embodiment of the third aspect of the invention, that is, the cyclic N-vinyl lactam-based crosslinked polymer preferably has a viscosity of 100 mPa·s or higher and lower than 10000 mPa·s determined under the above conditions. The crosslinked polymer with such a viscosity can have favorable applicability to the skin as a cosmetic.

The viscosity is preferably 500 mPa·s or higher and lower than 10000 mPa·s, more preferably 1000 mPa·s or higher and lower than 10000 mPa·s, still more preferably 3000 mPa·s or higher and 9000 mPa·s or lower, particularly preferably 5000 mPa·s or higher and 9000 mPa·s or lower, particularly further preferably 7000 mPa·s or higher and 9000 mPa·s or lower.

The cyclic N-vinyl lactam-based crosslinked polymer in the second embodiment of the third aspect of the invention in particulate form contains particles having an aspect ratio determined by the method described above of 1.15 to 10 in a proportion of 10% to 100% (by number) of the total number of the cyclic N-vinyl lactam-based crosslinked polymer particles. The particles having such a shape have a larger contact area with the skin than spherical particles. Such particles are easily caught on the surface of the skin and excellent in adhesiveness to the skin. In cases where the cyclic N-vinyl lactam-based crosslinked polymer particles form an aggregate, the aspect ratios of only primary particles free from aggregation are measured. In cases where the primary particles overlap each other, the aspect ratios of only particles free from overlapping are measured.

The aspect ratio is calculated by analyzing image data of a sample obtained from an optical or electron microscope using image analyzing particle size distribution measurement software. "Image analyzing particle size distribution measurement software Mac-view ver. 4 (Mountech Co., Ltd.)", a "particle image analysis system Morphologi G3 (product of Malvern in Spectris Co., Ltd.)", or image analysis software or an image analysis system which has the same principle as these may be available for the measurement.

The proportion of the particles having an aspect ratio of 1.15 to 10 may be determined by measuring the aspect ratios of randomly selected 100 or more particles.

The proportion of the particles having an aspect ratio of 1.15 to 10 is preferably 30% to 100% (by number), more preferably 50% to 100% (by number), still more preferably 70% to 100% (by number), particularly preferably 90% to 100% (by number), most preferably 100% (by number).

The aspect ratio of the particle is preferably 1.15 to 7, more preferably 1.15 to 5, still more preferably 1.2 to 5, particularly preferably 1.2 to 3, further particularly preferably 1.25 to 3, most preferably 1.25 to 2.5.

The average aspect ratio of randomly selected 100 or more particles of the cyclic N-vinyl lactam-based crosslinked polymer is preferably 1.15 to 5, more preferably 1.15 to 3, still more preferably 1.2 to 3, particularly preferably 1.2 to 2.5, most preferably 1.2 to 2.

It is also a preferred embodiment of the invention that the cyclic N-vinyl lactam-based crosslinked polymer in the first embodiment of the third aspect of the invention includes particles having an aspect ratio determined by the method described above of 1.15 to 10 in a proportion of 10% to 100% (by number) of the total number of the cyclic N-vinyl lactam-based crosslinked polymer particles.

It is also a preferred embodiment of the invention that the cyclic N-vinyl lactam-based crosslinked polymer of the second aspect of the invention has a viscosity determined under the above-described conditions of 100 mPa·s or higher and lower than 10000 mPa·s.

The crosslinked polymer in the third aspect of the invention may have any shape and is preferably in particulate form. That is, it is a preferred embodiment of the invention that the cosmetic of the invention contains a particulate cyclic N-vinyl lactam-based crosslinked polymer.

The crosslinked structure of the crosslinked polymer in the third aspect of the invention may be formed by the processes (1) to (5) and/or the processes (6) to (10) described for the first and second aspects of the invention, for example. The crosslinked structure may be formed by the processes (1) to (5) and/or the processes (6) to (10). The crosslinked structure formed by the process(es) (1) and/or (6) is preferred.

Preferred among the crosslinkable monomers in the processes (1), (5), (6), and (10) are compounds having at least two allyl groups because the use of such compounds tends to reduce a residual N-vinyl lactam and an extractable (uncrosslinked polymer fraction soluble in water). Specifically, preferred are cyanuric acid structure-containing crosslinkable monomers such as triallyl cyanurate, triallyl isocyanurate, triallyl phosphate, triallylamine, diallyl carbonate, 1,3-bis(allyloxy)-2-propanol, pentaerythritol (di, tri, or tetra) (meth)allyl ethers, and (di, tri, tetra, penta, hexa, hepta, or octa)allyl sucrose. More preferred are triallyl cyanurate, pentaerythritol (di, tri, or tetra) (meth)allyl ethers, and (di, tri, tetra, penta, hexa, hepta, or octa)allyl sucrose.

The cyclic N-vinyl lactam-based crosslinked polymer preferably contains a structural unit derived from a crosslinkable monomer in a ratio of preferably 0.0001 to 10 mol %, more preferably 0.01 to 1 mol % to 100 mol % of all structural units.

The absorbent or retention capacity for solvents such as water of the crosslinked body in the invention can be controlled by controlling the amount of the crosslinkable monomer to be used.

The cyclic N-vinyl lactam-based crosslinked polymer in the third aspect of the invention may have any average particle size. The average particle size is preferably 0.1 to 100 µm, more preferably 0.1 to 80 µm, still more preferably 0.1 to 50 µm, particularly preferably 1 to 40 µm. The polymer having an average particle size within the above ranges tends to have a higher absorption speed for, for example, water in the invention. Further, a cosmetic product containing such a polymer has favorable touch.

The average particle size of the crosslinked body is a value measured using a dry particle size distribution analyzer (Microtrac MT3000II series, MicrotracBEL Corp.) or a particle size distribution analyzer using a laser diffraction-scattering method that has the same principle as this.

The crosslinked polymer in the third aspect of the invention preferably has a water absorption capacity of 3 times or more, more preferably 5 times or more, still more preferably 10 times or more, particularly preferably 15 times, most preferably 20 times or more.

The crosslinked polymer in the third aspect of the invention preferably has an oil absorption capacity of 3 times or more, more preferably 5 times or more, still more preferably 10 times or more, particularly preferably 15 times or more, most preferably 20 times or more.

The water and oil absorption capacities are values calculated from "(weight of crosslinked polymer+amount of absorbed solution)/weight of crosslinked polymer". The liquid absorption capacity of the crosslinked polymer may be determined by the method described in the examples.

<Method of Producing Cyclic N-Vinyl Lactam-Based Crosslinked Polymer in the Third Aspect of the Invention>

The cyclic N-vinyl lactam-based crosslinked polymer contained in the cosmetic of the invention may be produced by any method and may be produced by polymerizing a monomer component. Specific examples and preferred examples of the monomer component, the crosslinking agent component, the proportion of the monomer component, and the ratio of the crosslinking agent component are the same as those described for the first and second aspects of the invention.

When the crosslinked structure is formed using the crosslinkable monomer, the polymerization and the formation of the crosslinked structure are performed at the same time. Such an embodiment is also a preferred embodiment of the invention.

In cases where the polymerization uses a polymerization initiator, the preferred range of the amount of the polymerization initiator to be used is the same as that in the second aspect of the invention.

In cases where the production method includes grinding, the grinding preferably uses a grinder.

Further, a jet mill is preferably used to grind the crosslinked body into particles having an average particle size of 100 µm or smaller.

The cosmetic of the invention may contain any amount of the cyclic N-vinyl lactam-based crosslinked polymer, and the proportion of the polymer in 100 mass % of the cosmetic is preferably 0.01 to 50 mass %, more preferably 0.05 to 30 mass %, still more preferably 0.1 to 20 mass %.

The cosmetic of the invention may contain a cyclic N-vinyl lactam-based polymer free from a crosslinked structure (an extractable). The proportion of the extractable in 100 mass % of the cyclic N-vinyl lactam-based crosslinked polymer is preferably 35 mass % or less. With a proportion of an extractable within the above preferred range, the concentration of an effective component in the cosmetic of the invention increases, the cosmetic has better moisturizing and oil-absorbing effects, and an increase in viscosity of the cosmetic is sufficiently prevented. The proportion of the extractable is more preferably 30 mass % or less, still more preferably 25 mass % or less, most preferably 20 mass % or less.

The proportion of the extractable in the cosmetic may be determined by the method described in the examples.

In the cosmetic of the invention, the proportion of the residual monomer such as the N-vinyl lactam-based monomer is preferably 200 ppm or less in 100 mass % of the cyclic N-vinyl lactam-based crosslinked polymer. The cosmetic of the invention having a proportion of the residual monomer within the above range is more highly safe. The proportion of the residual monomer is more preferably 100 ppm or less, still more preferably 50 ppm or less, most preferably 0 ppm.

The proportion of the residual monomer in the cosmetic may be determined by the method described in the examples.

The cosmetic of the invention may contain a different component other than the cyclic N-vinyl lactam-based crosslinked body. The different component is the same as described above.

<Fourth Aspect of the Invention: Absorbent Composite>

The following describes the technical features of the fourth aspect of the invention different from those of the first to third aspects of the invention.

The matters referring to "the fourth aspect of the invention" herein are common to the first and second embodiments of the fourth aspect of the invention.

The absorbent composite of the fourth aspect of the invention includes a nonionic crosslinked polymer and an absorbent base material. Such a composite is suitable for applications requiring a formed body, such as ink absorbent applications for printers, for example.

A nonionic crosslinked polymer has a lower liquid absorption speed than a conventional crosslinked body primarily containing a polyacrylic acid (salt). Such a disadvantage is reduced in a nonionic crosslinked polymer in the form of a composite with an absorbent base material. Specifically, when the absorbent composite absorbs liquid, the absorbent base material first absorbs liquid, and the nonionic crosslinked polymer then absorbs the diffused liquid. Such a composite, that is, the absorbent composite of the fourth aspect of the invention is capable of absorbing liquid faster than a nonionic crosslinked polymer alone.

Further, the absorbent composite of the fourth aspect of the invention has excellent liquid absorbency, and thus is suitable for cosmetic applications such as moisturizers.

The absorbent composite of the first embodiment of the fourth aspect of the invention has a mass ratio of the nonionic crosslinked polymer to the absorbent base material (nonionic crosslinked polymer/absorbent base material) of 0.1 or more and less than 2.

When the mass ratio of the nonionic crosslinked polymer to the absorbent base material is 0.1 or more, the nonionic crosslinked polymer is capable of further sufficiently receiving liquid absorbed by the absorbent base material, leading to sufficient prevention of leakage of liquid from the absorbent base material. This mass ratio is more preferably 0.2 or more, still more preferably 0.3 or more, still further more preferably 0.4 or more, particularly preferably 0.5 or more, most preferably 0.7 or more. The upper limit of the mass ratio is more preferably 1.9 or less, still more preferably 1.8 or less, still further more preferably 1.7 or less, particularly preferably 1.5 or less, most preferably 1.3 or less.

The absorbent composite of the second embodiment of the fourth aspect of the invention has a mass ratio of the nonionic crosslinked polymer to the absorbent base material (nonionic crosslinked polymer/absorbent base material) of 2.5 or more and 15 or less. When the mass ratio of the nonionic crosslinked polymer to the absorbent base material is 2.5 or more, the nonionic crosslinked polymer is capable of further sufficiently receiving liquid absorbed by the absorbent base material, leading to sufficient prevention of leakage of liquid from the absorbent base material.

I order to achive the above mass ratio of the nonionic crosslinked polymer to the absorbent base material, a space is preferably secured previously for the nonionic crosslinked polymer to swell by liquid absorption. In addition, the absorbent base material can be prevented from being broken by the internal pressure and the amount of liquid absorbed by the absorbent composite per volume thereof can be further increased by controlling the amount of the nonionic crosslinked polymer in consideration of swelling of the nonionic crosslinked polymer.

The mass ratio of the nonionic crosslinked polymer to the absorbent base material (nonionic crosslinked polymer/absorbent base material) in the second embodiment of the fourth aspect of the invention is 15 or less. When the mass ratio is 15 or less, the amount of the absorbent base material is further enough relative to the nonionic crosslinked polymer, and the absorption speed of the absorbent composite is further enhanced.

In the case of the absorbent composite having a planar shape such as a sheet shape, the absorbent composite preferably has a mass ratio of the nonionic crosslinked polymer to the absorbent base material of 2.5 to 5, more preferably 3 to 5.

In the case of the absorbent composite having a flat bag shape, the absorbent composite preferably has a mass ratio of the nonionic crosslinked polymer to the absorbent base material of 2.5 to 7, more preferably 3 to 5.

In the case of the absorbent composite having a three-dimensional bag shape such as a pyramid shape, the absorbent composite preferably has a mass ratio of the nonionic crosslinked polymer to the absorbent base material of 3 to 15, more preferably 4 or more, still more preferably 5 or more, particularly preferably 6 or more. The upper limit of the mass ratio is more preferably 13 or less, still more preferably 11 or less.

The absorbent composite preferably has a water absorption capacity of 3 to 30 g per 1 g of the absorbent composite. The water absorption capacity is preferably 5 g or greater, more preferably 10 g or greater, still more preferably 15 g or greater, particularly preferably 20 g or greater.

The absorbent composite preferably has an ethanol absorption capacity of 3 to 30 g per 1 g of the absorbent composite. Thus, the absorbent composite is suitable for cosmetic applications. The ethanol absorption capacity is preferably 5 g or greater, more preferably 10 g or greater, still more preferably 15 g or greater, particularly preferably 20 g or greater.

<Nonionic Crosslinked Polymer>

The absorbent composite of the fourth aspect of the invention contains a nonionic crosslinked polymer (hereinafter, also merely referred to as crosslinked polymer).

The absorbent composite of the fourth aspect of the invention containing a nonionic crosslinked polymer is capable of absorbing a highly concentrated organic solvent, for example. In addition, the nonionic properties of the crosslinked polymer make the composite highly safe.

The nonionic crosslinked polymer has a structural unit (a) derived from a nonionic monomer (A).

The nonionic monomer (A) may be any nonionic monomer. Examples thereof include amide monomers; unsaturated alcohols; (poly)alkylene glycol monomers; (meth)acrylates; aromatic vinyl monomers; alkenes; vinyl ethers; vinyl carboxylates; and vinyl ethylene carbonates and derivatives thereof.

The nonionic crosslinked polymer preferably includes a structural unit derived from an amide monomer and/or a structural unit derived from a (poly)alkylene glycol monomer.

The amide monomers may be any of those having an amide structure and an ethylenically unsaturated hydrocarbon group. Examples thereof include monomers having a lactam structure (hereinafter, also referred to as lactam-based monomers (N-vinyl lactam-based monomers)); N-substituted or unsubstituted (meth)acrylamides such as (meth)acrylamide, N-monomethyl (meth)acrylamide, N-monoethyl (meth)acrylamide, N,N-dimethyl (meth)acrylamide, and N-isopropylacrylamide; vinylacetamides such as N-vinylacetamide and N-vinyl-N-methylacetamide; N-substituted or unsubstituted vinylformamides such as N-vinylformamide and N-vinyl-N-methylformamide; and vinyloxazolidones.

Example of the unsaturated alcohols include hydroxyethyl (meth)acrylate, hydroxypropyl (meth)acrylate, 3-(meth)allyloxy-1,2-dihydroxypropane, (meth)allyl alcohol, and isoprenol.

The (poly)alkylene glycol monomers may be any of those having a (poly)alkylene glycol chain and an ethylenically unsaturated hydrocarbon group. Examples thereof include: alkylene oxide adducts in which an alkylene oxide is added to a hydroxy group of the above-described unsaturated alcohols; and esters of a (poly)alkylene glycol and an unsaturated carboxylic acid such as (meth)acrylic acid.

The (poly)alkylene glycol monomers preferably have a structure represented by the following formula (4):

[Chem. 4]

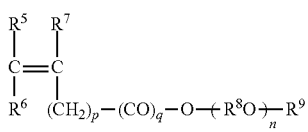

(4)

wherein $R^5$ to $R^7$ are the same as or different from each other and each represent a hydrogen atom or a methyl group; $R^8$Os are the same as or different from each other and each represent a C2-C18 oxyalkylene group; $R^9$ represents a hydrogen atom or a C1-C30 hydrocarbon group; p represents 0 to 5, q represents 0 or 1; n represents the average number of moles of oxyalkylene group added and represents 1 to 300.

$R^5$ to $R^7$ in the formula (4) are the same as or different from each other and each represent a hydrogen atom or a methyl group. Preferably, at least one of $R^5$ and $R^6$ is a hydrogen atom.

The oxyalkylene group represented by —($R^8$O)— in the formula (4) is a C2-C18 oxyalkylene group. In cases where two or more types of oxyalkylene groups are present, they may be added in any form such as random addition, block addition, or alternating addition.

The oxyalkylene group represented by —($R^8$O)— is preferably a C2-C8 oxyalkylene group, more preferably a C2-C4 oxyalkylene group.

Such an oxyalkylene group is an alkylene oxide adduct. Examples of the alkylene oxide include ethylene oxide, propylene oxide, butylene oxide, isobutylene oxide, 1-butene oxide, 2-butene oxide, and styrene oxide. Preferred are ethylene oxide, propylene oxide, and butylene oxide, and more preferred are ethylene oxide and propylene oxide.

In cases where the oxyalkylene group represented by —($R^8$O)— in the formula (4) includes an oxyethylene group to which an ethylene oxide is added, the oxyethylene group is preferably present in a proportion of 50 to 100 mol % in 100 mol % of all oxyalkylene groups. At such a proportion of the oxyethylene group, an increase in air entrainment is prevented, the air content can be easily controlled, and a reduction of strength or a reduction of freeze-thaw resistance can be prevented. The proportion of the oxyethylene group is more preferably 60 to 100 mol %, still more preferably 70 to 100 mol %, particularly preferably 80 to 100 mol %, most preferably 90 to 100 mol %.

$R^9$ in the formula (4) represents a hydrogen atom or a C1-C30 hydrocarbon group. $R^9$ is preferably a C1-C20 hydrocarbon group or a hydrogen atom, more preferably a hydrogen atom or a C1-C18 hydrocarbon group, still more preferably a hydrogen atom or a C1-C12 hydrocarbon group, particularly preferably a hydrogen atom or a C1-C8 hydrocarbon group, most preferably a hydrogen atom or a C1-C3 hydrocarbon group.

Examples of the hydrocarbon group include linear or branched alkyl groups such as methyl, ethyl, propyl, isopropyl, n-butyl, isobutyl, sec-butyl, tert-butyl, pentyl, isopentyl, neopentyl, hexyl, heptyl, octyl, nonyl, decyl, undecyl, dodecyl, isooctyl, 2,3,5-trimethylhexyl, 4-ethyl-5-methyloctyl, 2-ethylhexyl, tetradecyl, octadecyl, and icosyl groups; cyclic alkyl groups such as cyclopropyl, cyclobutyl, cyclopentyl, cyclohexyl, cycloheptyl, and cyclooctyl; aryl groups such as phenyl, benzyl, phenethyl, o-, m- or p-tolyl, 2,3- or 2,4-xylyl, mesityl, naphthyl, anthryl, phenanthryl, biphenylyl, benzhydryl, trityl, and pyrenyl groups. Preferred among these are linear, branched, and cyclic alkyl groups.

In the formula (4), p represents 0 to 5 and q represents 0 or 1. A preferred combination of p and q is a combination in which p is 1 or 2 and q is 0 or a combination in which p is 0 and q is 1.

In the formula (4), n represents the average number of moles of oxyalkylene group added and represents 1 to 300. The average number of moles of oxyalkylene group added is preferably 1 to 150, more preferably 1 to 100, still more preferably 1 to 80, particularly preferably 1 to 50, most preferably 1 to 30.

The (meth)acrylates may be any ester of (meth)acrylic acid and a C1-C20 alcohol. Examples thereof include methyl (meth)acrylate, ethyl (meth)acrylate, butyl (meth)acrylate, and cyclohexyl (meth)acrylate.

Examples of the aromatic vinyl monomers include styrene, α-methylstyrene, vinyl toluene, indene, vinyl naphthalene, and phenyl maleimide.

Examples of the alkenes include ethylene, propylene, butadiene, isobutylene, and octene.

Examples of the vinyl ethers include methyl vinyl ether, ethyl vinyl ether, and butyl vinyl ether.

Examples of the vinyl carboxylates include vinyl acetate and vinyl propionate.

Preferred among the above-described nonionic monomers (A) are amide monomers and (poly)alkylene glycol monomers.

That is, the nonionic crosslinked polymer in the fourth aspect of the invention preferably includes a structural unit derived from an amide monomer and/or a structural unit derived from a (poly)alkylene glycol monomer, more preferably includes a structural unit derived from an amide monomer.

The crosslinked structure of the nonionic crosslinked polymer in the fourth aspect of the invention can be formed by the processes (1) to (5) and/or the processes (6) to (10) described for the first and second aspects of the invention, for example. The crosslinked structure may be formed by any of the processes (1) to (5) and/or the processes (6) to (10) and is preferably formed by the process(es) (1) and/or (6).

The crosslinkable monomers in the processes (1), (5), (6), and (10) are preferably the crosslinkable monomers described for the third aspect of the invention.

The nonionic crosslinked polymer may include a structural unit (e) derived from a monomer (E) other than, and in addition to, the nonionic monomer (A) and the crosslinkable monomer. The nonionic crosslinked polymer may contain a structural unit derived from an ionic monomer as the monomer (E) as long as the nonionic crosslinked polymer has nonionic properties.

Examples of the monomer (E) include (i) unsaturated monocarboxylic acids such as acrylic acid and methacrylic acid and salts thereof; (ii) unsaturated dicarboxylic acids such as fumaric acid, maleic acid, methylene glutaric acid, and itaconic acid and salts thereof (which may be either monovalent salts or divalent salts); (iii) unsaturated sulfonic acids such as 3-allyloxy-2-hydroxypropane sulfonic acid, (meth)allylsulfonic acid, isoprenesulfonic acid, (meth) acrylic acid-2-sulfoethyl ester, and derivatives thereof and salts of the unsaturated sulfonic acids; (iv) unsaturated amines such as N,N-dimethylaminoethyl (meth)acrylate, N,N-dimethylaminoethyl (meth)acrylamide, vinylpyridine, and vinylimidazole and salts and quaternary compounds thereof; and (v) unsaturated anhydrides such as maleic anhydride and itaconic anhydride.

Each of these may be used alone, or two or more of these may be used in combination.

Examples of the salts in (i) to (iii) include metal salts, ammonium salts, and organic amine salts. Examples of the salts in (iv) include hydrochlorides and sulfates.

In the nonionic crosslinked polymer, the proportion of the structural unit (a) derived from a nonionic monomer (A) is preferably 30 to 100 mol % in 100 mol % of all structural units (structural unit (a) derived from a nonionic monomer (A) and structural unit derived from a monomer (E)). The proportion is more preferably 50 to 100 mol %, still more preferably 70 to 100 mol %, further preferably 80 to 100 mol %, particularly preferably 90 to 100 mol %, most preferably 100 mol %. Here, all structural units do not include the structure derived from the crosslinkable monomer.

In the nonionic crosslinked polymer having a unit derived from an amide monomer and/or a unit derived from a (poly)alkylene glycol monomer, the proportion of the structural unit derived from an amide monomer and/or the structural unit derived from a (poly)alkylene glycol monomer is preferably 30 to 100 mol %, more preferably 50 to 100 mol %, still more preferably 70 to 100 mol %, further preferably 80 to 100 mol %, particularly preferably 90 to 100 mol %, most preferably 100 mol % in 100 mol % of all structural units.

In the nonionic crosslinked polymer, the proportion of the structural unit (e) derived from a monomer (E) is preferably 0 to 70 mol %, more preferably 0 to 50 mol %, still more preferably 0 to 30 mol %, further preferably 0 to 20 mol %, particularly preferably 0 to 10 mol %, most preferably 0 mol % to 100 mol % of all structural units.

In the nonionic crosslinked polymer, the ratio of the structural unit derived from a crosslinkable monomer and/or the structural unit derived from a crosslinking agent is preferably 0.01 to 2 mol %, more preferably 0.01 to 1 mol %, still more preferably 0.05 to 1 mol %, most preferably 0.1 to 1 mol % to 100 mol % of all structural units.

The absorbent or retention capacity for solutions such as ink of the nonionic crosslinked polymer in the fourth aspect of the invention can be controlled by controlling the amount(s) of the crosslinkable monomer and/or the crosslinking agent to be used. Further, the nonionic crosslinked polymer containing the structural unit derived from a crosslinkable monomer and/or the structural unit derived from a crosslinking agent in a ratio of 0.01 mol % or more is easily pulverized during its production.

The nonionic crosslinked polymer in the fourth aspect of the invention may have any average particle size. The average particle size is preferably 0.1 μm or larger and 2000 μm or smaller, more preferably 0.1 μm or larger and 1000 μm or smaller, still more preferably 1 μm or larger and 1000 μm or smaller, further preferably 3 μm or larger and 1000 μm or smaller, further more preferably 5 μm or larger and 1000 μm or smaller, particularly preferably 10 μm or larger and 1000 μm or smaller, most preferably 50 μm or larger and 850 μm or smaller. The nonionic crosslinked polymer in the fourth aspect of the invention having an average particle size within the above preferred ranges tends to have an enhanced absorption capacity for liquid such as water and an absorption speed within a suitable range. The nonionic crosslinked polymer having an average particle size of 0.1 μm or larger can be sufficiently prevented from being a clump when the nonionic crosslinked polymer absorbs liquid such as water. In addition, when the polymer is formed on a sheet-like absorbent base material to prepare a sheet-like absorbent base material, falling of powder from the sheet-like absorbent base material can be sufficiently prevented. The nonionic crosslinked polymer having an average particle size of 2000 μm or smaller is capable of sufficiently preventing formation of a gap between particles and a gap between particles and the absorbent base material when the polymer is formed on a sheet-like absorbent base material. Preferably, the nonionic crosslinked polymer has an average particle size of 300 μm or smaller and contains fine powder with a size smaller than 100 μm. In this case, the crosslinked polymer is more likely to stick to the sheet.

In order to produce a bag-like absorbent composite, the crosslinked polymer preferably has an average particle size of 100 to 500 μm. The crosslinked polymer having an average particle size of 100 μm or larger can be sufficiently prevented from leaking from a mesh of the bag-like absorbent base material. The crosslinked polymer having an average particle size of 500 μm or smaller tends to have a higher absorption speed.

The average particle size of the nonionic crosslinked polymer may be determined by the method described in the examples.

<Method of Producing Nonionic Crosslinked Polymer>

The nonionic crosslinked polymer may be produced by any method and may be produced by polymerizing a monomer component. Specific examples and preferred examples of the monomer component, the monomer component, the crosslinking agent component, and the proportion of the monomer component, and the ratio of the crosslinking agent are the same as those described for the first and second aspects of the invention. Here, the term "all monomers" in the preferred proportion or ratio to 100 mol % of all monomer components described for the first and second aspects of the invention is replaced with "all monomers (nonionic monomer and monomer (E))".

In cases where the polymerization uses a polymerization initiator, the amount of the polymerization initiator is preferably 0.1 g or greater and 10 g or less, more preferably 0.1 g or greater and 7 g or less, still more preferably 0.1 g or greater and 5 g or less per 1 mol of the monomers used (the total amount of the nonionic monomer (A), the above-described monomer (E), and the crosslinkable monomer used).

The use of 0.1 g or greater of the initiator allows a sufficient reduction of the proportion of an unreacted monomer contained in the resulting crosslinked polymer. The use of 10 g or less of the initiator allows a sufficient reduction of the proportion of impurities contained in the resulting crosslinked polymer. Also, the use of such a proportion of the initiator allows prevention of discoloration of the resulting crosslinked polymer.

In cases where the production method includes grinding, the particle size distribution is more preferably controlled using a roll mill, a hammer grinder, an impact grinder, a pin mill, or a jet mill.

A jet mill is preferably used to grind the nonionic crosslinked polymer into particles having an average particle size of 100 μm or smaller.

In the case of the nonionic crosslinked polymer in the invention having a crosslinked structure formed by the process(es) (5) and/or (10), the amount of the crosslinkable monomer used in the post-crosslinking is preferably 0.1 to 50 mass %, more preferably 1 to 30 mass % relative to 100 mass % of the polymer before the post-crosslinking. The use of the crosslinkable monomer in such a ratio allows sufficient formation of the crosslinked structure. Thus, the crosslinked polymer is capable of more sufficiently absorbing a pigment contained in ink, and the amount of an unreacted crosslinkable monomer remaining in the resulting crosslinked polymer can be reduced.

In cases where the production method includes aging, the aging is preferably performed while the nonionic crosslinked polymer is pulverized. In the production method including adding an organic acid, the pulverization allows the organic acid to sufficiently permeate the pulverized crosslinked polymer. Thus, the amount of the N-vinyl lactam-based monomer remaining in the resulting polymer can be more sufficiently reduced. The polymer may be pulverized by a common method. For example, the pulverization is performed by a method using a screw extruder such as a kneader or a meat chopper, or a gel grinder such as a cutter mill.

When the method of producing the nonionic crosslinked polymer includes addition of an organic acid and the below-described bag-like absorbent composite is produced as the absorbent composite of the invention, the method preferably includes neutralization after the addition of an organic acid.

When the nonionic crosslinked polymer is swollen by water and bonded to a base material to produce the sheet-like absorbent composite described below, the method preferably includes no neutralization because the crosslinked polymer is less likely to stick to the sheet in the presence of an organic acid salt. Further, the production of such a sheet-like absorbent composite needs neither the addition nor the neutralization of the organic acid.

<Absorbent Composite>

The absorbent composite of the invention may have any shape. Examples of the shape include a planar shape such as a sheet shape or a flake shape, and a three-dimensional shape such as a rod shape (cylindrical or quadrangular prism), a spherical shape, a pyramidal shape (a triangular pyramid or a quadrangular pyramid), a conical shape, or a massive shape.

The term "sheet" herein means a shape having a planar spread generally recognized as a sheet. The shape preferably satisfies that $[a^{(1/2)}]/b$ is 5 or more, where "a" represents the area of the surface having the largest area in the shape and "b" represents the length in the direction perpendicular to the surface (the thickness of the shape). When the thickness of the shape is not uniform, the maximum value of the thickness is defined as "b".

The absorbent composite of the invention preferably has a sheet shape or a pyramidal shape.

In the case of the absorbent composite having a planar shape such as a sheet shape, the absorbent base material and the nonionic crosslinked polymer have a large area to be in contact with liquid to be absorbed. Thus, the absorbent base material instantaneously absorbs the liquid, and the nonionic crosslinked polymer strongly receives the liquid from the absorbent base material and holds it. Thus, the liquid absorption speed of the entire sheet is further enhanced, and the liquid is sufficiently diffused throughout the sheet.

In addition, in the case of the absorbent composite having a sheet shape, the thickness of the absorbent composite containing liquid absorbed is less changed. Thus, such an absorbent composite is suitable for applications in which the thickness is specified.

In the case of the absorbent composite having a three-dimensional shape such as a conical shape or a pyramidal shape, the composite is preferably a packaged body in which the nonionic crosslinked polymer is packaged with a sheet-like absorbent base material or packed and sealed in a bag-like absorbent base material. The absorbent composite having such a shape easily secures a space for the nonionic crosslinked polymer to swell by liquid absorption. Thus, the absorbent base material can be prevented from being broken by the internal pressure and the liquid absorption amount per volume of the absorbent composite can be increased by controlling the amount of the nonionic crosslinked polymer in consideration of the swelling of the nonionic crosslinked polymer.

The volume of the nonionic crosslinked polymer after swelling depends on its swelling ratio. Thus, the amount of the nonionic crosslinked polymer in the packaged body depends on the types of the crosslinked polymer and the liquid to be absorbed. The volume of the nonionic crosslinked polymer before liquid absorption is preferably 2% to 35%, more preferably 3% to 20% of the volume of the nonionic crosslinked polymer after swelling in the packaged body taken as 100%.

In the absorbent composite of the invention, the nonionic crosslinked polymer is preferably supported on an absorbent base material.

The nonionic crosslinked polymer may be supported on an absorbent base material by any method. Examples thereof include a method of immersing an absorbent base material in a solution containing the nonionic crosslinked polymer, a method of supporting the nonionic crosslinked polymer on an absorbent base material using a bonding agent, a method of mixing an absorbent base material with the nonionic crosslinked polymer, a method of bringing the nonionic crosslinked polymer into close contact with a base material, and a method of packaging the nonionic crosslinked polymer with a sheet-like absorbent base material or packed and sealed in a bag-like absorbent base material (e.g., a method of forming a packaged body). Here, the packaged body means a form in which powder (nonionic crosslinked polymer) is packaged with an absorbent base material so as not to leak therefrom.

In the method of immersing the absorbent base material in a solution containing the nonionic crosslinked polymer, the solution may contain a different component other than the nonionic crosslinked polymer. Examples of the different component include a polymer prepared by polymerizing a monomer such as (meth)acrylic acid or (meth)acrylate and a solvent such as water or methanol.

In the method of supporting the nonionic crosslinked polymer on an absorbent base material using a bonding agent, the bonding agent may contain any component. Examples of the bonding agent component include synthetic rubber such as styrene-butadiene rubber or chloroprene rubber; an organic solvent such as n-pentane, acetone, or toluene; gas such as LPG or dimethyl ether; and adhesive resin (binder) such as polyvinylpyrrolidone.

Specific examples of the method of supporting the nonionic crosslinked polymer on an absorbent base material using a bonding agent include, but are not limited to, spraying on the surface of a base material surface a dispersion in which the bonding agent and the nonionic crosslinked polymer are dispersed in a dispersion medium such as an organic solvent or water; applying the dispersion with a brush or a roller; and impregnating an absorbent base material with the dispersion. Alternatively, a method may be used in which a solution or dispersion containing a bonding agent is sprayed on or applied to an absorbent base material surface, the nonionic crosslinked polymer is then uniformly sprinkled on the surface, and the solution or dispersion is again sprayed thereon or applied thereto. The dispersion or the like applied to the base material may be dried as needed. Thus, the nonionic crosslinked polymer is bonded to the absorbent base material surface (outer surface and/or inner surface) via the bonding agent. That is, a layer of the nonionic crosslinked polymer is formed. In the case of forming a resin layer containing the nonionic crosslinked polymer on an absorbent base material surface, the above method does not need dispersing the nonionic crosslinked polymer and/or sprinkling the nonionic crosslinked polymer.

The absorbent base material may be mixed with the nonionic crosslinked polymer by any method. Examples of the method include mixing ground wood pulp with the nonionic crosslinked polymer, kneading a mixture containing the nonionic crosslinked polymer and elastomer such as chloroprene rubber and rolling the kneaded mixture, binding the nonionic crosslinked polymer with, for example, an adhesive resin, and dispersing the nonionic crosslinked polymer during the formation of a nonwoven fabric.

The nonionic crosslinked polymer may be bonded to the absorbent base material by any method. Examples of the method include a method including allowing the nonionic crosslinked polymer and/or the absorbent base material absorb water, bringing the crosslinked polymer into contact with the absorbent base material, and dehydrating and drying them; and a method of thermal fusion bonding or pressure bonding absorbent base materials with a thermoplastic resin or adhesive such as polypropylene or polyethylene and the nonionic crosslinked polymer held therebetween using a thermal roll.

In the case of the absorbent composite having a planar shape such as a sheet shape, it may be formed of one absorbent layer including an absorbent base material and the nonionic crosslinked polymer or may be formed of two or more layers stacked to each other.

For example, the absorbent composite may have a structure in which a nonionic crosslinked polymer-supported sheet and a sheet not supporting the polymer are alternately stacked or a structure in which multiple sheets supporting the nonionic crosslinked polymer are arranged in amounts in ascending order, sheets supporting a smaller amount of the nonionic crosslinked polymer are arranged in the upper portion.

Alternatively, the absorbent composite may have a multilayer structure in which two or more nonwoven fabrics different in material (e.g., PP (polypropylene), PE (polyethylene), cellulose, polyamide, nylon, and polyester) each having the nonionic crosslinked polymer fixed thereon are stacked.

In the case of the absorbent composite having a planar shape such as a sheet shape, the absorbent composite preferably has a thickness of 0.01 to 50 mm, more preferably 0.01 to 30 mm, still more preferably 0.01 to 20 mm, particularly preferably 0.05 to 10 mm, most preferably 0.1 to 5 mm.

The absorbent composite preferably has a weight per unit area of 0.1 to 3000 $g/m^2$, more preferably 0.5 to 2500 $g/m^2$, still more preferably 1 to 1500 $g/m^2$.

<Absorbent Base Material>

The absorbent base material may be any material that supports the nonionic crosslinked polymer. Examples thereof include paper, fabric, wood, elastomer, resin foam, and porous base materials.

The paper is one defined in JIS P 0001, and the fabric is a collective term of sheet-like fiber products defined in JIS L 0206.

The paper is preferably an adhesive paper such as a heat sealable paper.

The basis weight of the paper is preferably, but not limited to, 15 to 100 $g/m^2$.

Examples of the fabric include woven fabric, knitted fabric, braided fabric, lace, mesh, and nonwoven fabric. Preferred are woven fabric, knitted fabric, and nonwoven fabric, and more preferred is nonwoven fabric.

Examples of the resin foam and porous base materials include, but are not limited to, polyurethane foam, polystyrene foam, and inorganic porous bodies.

Examples of a fiber material forming the absorbent base material include, but are not limited to, hydrophobic fibers such as polyester and polypropylene; cellulosic fibers; polyamide fibers; hydrophilic fibers such as animal fibers (e.g., silk and wool); and hydrophobic fibers having a hydrophilic surface layer.

The hydrophilic fiber indicates a fiber having an official moisture regain of 3% or higher.

The official moisture regain of the fiber may be measured according to the method described in JIS L 0105.

The absorbent base material preferably contains a hydrophilic fiber. The hydrophilic fiber is preferably at least one selected from the group consisting of cellulose fibers, polyamide fibers, animal fibers, and hydrophobic fibers having a hydrophilic surface layer.

In cases where hydrophilic fiber, which has high diffusivity of liquid, is contained as the absorbent base material, the nonionic crosslinked polymer further rapidly receives liquid absorbed by the absorbent base material. Thus, the absorption speed of the entire absorbent composite is enhanced.

The absorbent base material more preferably contains a cellulose fiber.

Examples of the cellulose fiber include natural fibers such as cotton and hemp; recycled fibers such as rayon, cupra, lyocell, and polynosic fibers; semisynthetic fibers such as acetate and triacetate; and pulp.

The absorbent base material may have any shape capable of forming a composite with the nonionic crosslinked polymer.

The absorbent base material preferably has a sheet shape or a bag shape.

The absorbent composite of the invention is capable of absorbing water, a water-soluble organic solvent, or ink, for example.

Examples of the water-soluble organic solvent include alcohols and glycols such as glycerol, ethylene glycol, diethylene glycol, triethylene glycol, propylene glycol, and dipropylene glycol; amide solvents such as N,N-dimethylformamide and N,N-dimethylacetamide; pyrrolidones such as 2-pyrrolidone and N-methyl-2-pyrrolidone; 2-oxazolidone; 1,3-dimethyl-2-imidazolidinone; 1,1,3,3-tetramethyl urea; dimethyl sulfoxide; and sulfolanes.

The water-soluble organic solvent is preferably glycerol, a glycol, an alcohol, or a pyrrolidone.

The ink may contain the same component as the ink component for the first aspect of the invention.

The invention also relates to an ink absorber including the absorbent composite of the invention.

The invention also relates to an absorbent material including the ink absorber.

The invention also relates to an ink-absorbed body including the ink absorber and ink absorbed by the ink absorber.

The invention also relates to a printer including the ink absorber.

The invention also relates to a method of using the ink absorber, the ink absorber being incorporated into a printer.

Here, the ink absorber means one before absorbing ink, and the ink-absorbed body means one containing ink absorbed.

The invention also relates to a cosmetic containing the absorbent composite of the invention.

The invention also relates to a method of using the absorbent composite of the invention as a cosmetic.

The invention also relates to a deodorant containing the absorbent composite of the invention.

The invention also relates to a deodorizer including the deodorant.

The invention also relates to a method of using the deodorant, the deodorant being incorporated into a deodorizer.

<Fifth Aspect of the Invention: Ink Absorbing Agent>

The following describes the technical features of the fifth aspect of the invention different from those of the first to fourth aspects of the invention.

The ink absorbing agent of the fifth aspect of the invention contains a N-vinyl lactam-based crosslinked polymer (cyclic N-vinyl lactam-based crosslinked polymer) (hereinafter, also referred to as crosslinked polymer of the invention) including a structural unit derived from a N-vinyl lactam.

The ink absorbing agent of the fifth aspect of the invention that contains the crosslinked polymer of the invention including a structural unit derived from a cyclic N-vinyl lactam is capable of sufficiently absorbing ink, leading to a sufficient reduction of residual ink liquid.

Conventional ink absorbing agents such as polyacrylic acid-based liquid absorbent resins and polyethylene oxide crosslinked polymers are capable of absorbing an organic solvent as a water-rich aqueous solution. However, when the water evaporates and the organic solvent component in the solution absorbed by the ink absorbing agents is concentrated, the polymer cannot hold the liquid any longer, causing liquid leakage (discharge).

On the other hand, the ink absorbing agent of the invention is capable of absorbing a highly concentrated organic solvent and is also capable of retaining the organic solvent absorbed, leading to sufficient prevention of leakage of liquid.

The crosslinked structure of the crosslinked polymer in the invention may be formed by the processes (1) to (5) and/or the processes (6) to (10) described for the first and second aspects of the invention. The preferred embodiments of the crosslinked structure formed by the processes (1) to (5) and/or the processes (6) to (10) are the same as those for the first and second aspects of the invention, for example. Specific examples of the crosslinkable monomer are the same as those described for the first and second aspects of the invention. The crosslinked structure may be formed by the processes (1) to (5) and/or the processes (6) to (10) and is preferably formed by the process(es) (1) and/or (6).

The crosslinkable monomers in the processes (1), (5), (6), and (10) are preferably the crosslinkable monomers described for the first and second aspects of the invention.

In the N-vinyl lactam-based crosslinked polymer, the ratio of the structural unit derived from a crosslinkable monomer and/or the structural unit derived from a crosslinking agent is preferably 0.01 to 2 mol %, more preferably 0.01 to 1 mol %, still more preferably 0.05 to 1 mol %, most preferably 0.1 to 1 mol % relative to 100 mol % of all the structural units.

The absorbent or retention capacity for ink of the crosslinked polymer in the invention can be controlled by controlling the amount(s) of the crosslinkable monomer and/or crosslinking agent to be used. Further, the crosslinked polymer containing the structural unit derived from a crosslinkable monomer and/or the structural unit derived from a crosslinking agent in a ratio of 0.01 mol % or more is easily pulverized during its production.

The crosslinked polymer of the invention may have any average particle size. The average particle size is preferably 0.1 µm or larger and 2000 µm or smaller, more preferably 0.1 µm or larger and 1000 µm or smaller, further preferably 1 µm or larger and 1000 µm or smaller, further more preferably 3 µm or larger and 1000 µm or smaller, still more preferably 5 µm or larger and 1000 µm or smaller, particularly preferably 10 µm or larger and 1000 µm or smaller, most preferably 50 µm or larger and 850 µm or smaller. The crosslinked polymer having an average particle size within the above preferred ranges tends to have an enhanced absorption capacity for liquid such as water and an absorption speed within a suitable range. The crosslinked polymer having an average particle size of 0.1 µm or larger can be sufficiently prevented from being a clump when the crosslinked polymer absorbs liquid such as water. In addition, when the polymer is formed into an ink absorbent sheet, falling of powder from the sheet base material can be sufficiently prevented.

The average particle size of the crosslinked polymer may be determined by the method described in the examples.

The crosslinked polymer in the invention has an excellent ink absorption capacity. For example, the crosslinked polymer preferably has an ink absorption capacity of 5 times or more, more preferably 10 times or more, still more preferably 15 times or more, further more preferably 20 times or more, measured using a pigment ink BK (BCI-350 (PGBK), Canon Inc.).

The crosslinked polymer in the invention also has an excellent organic solvent absorption capacity. For example, the crosslinked polymer preferably has an ethylene glycol absorption capacity of 5 times or more, more preferably 10 times or more, still more preferably 15 times or more.

The ink and organic solvent absorption capacities of the crosslinked polymer may be determined by the method described in the examples.

The crosslinked polymer in the invention may take any period of time to absorb deionized water (conductivity: 10 μS/cm or lower) in an amount of 15 times the weight of the polymer itself (liquid absorption capacity: 15 times), and preferably takes 0.1 to 1500 minutes, more preferably 0.3 to 600 minutes, further more preferably 0.5 to 300 minutes, most preferably 1 to 60 minutes.

Further, the crosslinked polymer in the invention may take any period of time to absorb propylene glycol in an amount of 4 times the weight of the polymer itself (liquid absorption capacity: 4 times), and preferably takes 0.1 to 1500 minutes, more preferably 0.3 to 600 minutes, further more preferably 0.5 to 300 minutes, most preferably 1 to 60 minutes.

<Method of Producing Cyclic N-Vinyl Lactam-Based Crosslinked Polymer in the Fifth Aspect of the Invention>

The cyclic N-vinyl lactam-based crosslinked polymer contained in the ink absorbing agent of the invention may be produced by any method, and may be produced by polymerizing a monomer component. Specific examples and preferred examples of the monomer component are the same as those described above. The proportion of the cyclic N-vinyl lactam, the proportion of the monomer (E), and the ratio of the crosslinkable monomer to 100 mol % of all monomer components (cyclic N-vinyl lactam and monomer (E)) are the same as the proportion of the structural unit derived from a cyclic N-vinyl lactam, the proportion of the structural unit derived from a monomer (E), and the ratio of the structural unit derived from a crosslinkable monomer to 100 mol % of all structural units, respectively, as described above.

In cases where the polymerization uses a polymerization initiator, the preferred range of the amount of the polymerization initiator to be used is the same as that in the first aspect of the invention.

In cases where the production method includes grinding, a hammer grinder, an impact grinder, a pin mill, or a jet mill is preferably used to control the particle size distribution.

Further, a jet mill is preferably used to grind the crosslinked polymer into particles having an average particle size of 100 μm or smaller.

The invention also relates to an absorbent material including the ink absorbing agent of the invention.

The absorbent material may have any shape suitable for use. Examples thereof include a sheet shape, a rod shape (cylindrical or quadrangular prism), a spherical shape, a pyramidal shape, a conical shape, a flake shape, and a massive shape. Preferred are a sheet shape and a rod shape.

When the ink absorbing agent of the invention is used in an ink jet recording apparatus, for example, the absorbent material including the ink absorbing agent is capable of sufficiently preventing leakage of powder of the ink absorbing agent in the recording apparatus. This allows sufficient prevention of failure such as clogging of an ink jet nozzle, for example.

The absorbent material preferably includes a base material and an ink absorbing agent. More preferably, the ink absorbing agent is supported on the base material.

The base material of the absorbent material may be any material commonly used. Since the ink absorbing agent of the invention has an excellent ink retention capacity, the absorbent material has an excellent ink retention capacity regardless of the ink retention capacity of the base material itself. Thus, leakage of liquid can be sufficiently prevented even when the absorbent material is inclined.

Examples of the base material include those described for the fourth aspect of the invention.

The absorbent agent may include a different ink absorbing agent other than the ink absorbing agent of the invention. The different ink absorbing agent may be any agent capable of absorbing ink. Examples thereof include acid group-containing superabsorbent resins, inorganic absorbent powders (e.g., powdered zeolite, powdered clays), and powders having a structure similar to an organic dye or an organic pigment (e.g., phthalocyanine structure, porphyrin structure). A mixture of at least one of these ink absorbing agents and the ink absorbing agent of the invention may be supported on a base material.

The ink absorbing agent of the invention may be supported on a base material by any method. Examples of the method include a method of immersing a base material in a resin solution containing the ink absorbing agent, a method of supporting the ink absorbing agent on a base material using a bonding agent, a method of mixing a base material with the ink absorbing agent, a method of thermal fusion bonding or pressure bonding the ink absorbing agent to a base material, a method of packaging the ink absorbing agent with a base material and sealing it (e.g., a method of forming a packaged body). Here, the packaged body means a form in which powder (ink absorbing agent) is packaged with a base material so as not to leak therefrom.

In the method of immersing the base material in a resin solution containing the ink absorbing agent, the resin solution may contain a different component other than the ink absorbing agent. Examples of the different component include polymers prepared by polymerizing a monomer such as (meth)acrylic acid or (meth)acrylate; and solvents such as methanol.

The bonding agent component in the method of supporting the ink absorbing agent on a base material using a bonding agent, the method of supporting the ink absorbing agent on a base material using a bonding agent, and the method of mixing a base material with the ink absorbing agent are the same as those described for the fourth aspect of the invention.

The ink absorbing agent may be thermally fusion bonded to a base material by any method. An example of the method is one in which a thermoplastic resin or adhesive such as polypropylene or polyethylene and the ink absorbing agent are held between base materials, and they are thermally fusion bonded or pressure bonded using a thermal roll.

The ink absorbing agent may be packaged with and sealed in a base material by any method. The ink absorbing agent is preferably distributed in partitioned small sections in order to prevent uneven distribution of the ink absorbing agent when the absorbent material is inclined.

In the absorbent material, the ratio of the ink absorbing agent of the invention to 100 mass % of the base material is preferably 10 to 20000 mass %, more preferably 20 to 10000 mass %, still more preferably 30 to 500 mass %, further more preferably 30 to 200 mass %, particularly preferably 30 to 180 mass %.

The absorbent material is preferably in the form of a sheet or a packaged body.

The term "sheet" herein means a shape having a planar spread generally recognized as a sheet. The shape preferably satisfies that $[a^{(1/2)}]/b$ is 5 or more, where "a" represents the area of the surface having the largest area in the shape and "b" represents the length in the direction perpendicular to the surface (the thickness of the shape). When the thickness of the shape is not uniform, the maximum value of the thickness is defined as "b".

In cases where the ink absorbing agent is supported on a sheet-like base material, the base material and the ink absorbing agent have a large area to be in contact with ink. Thus, the base material instantaneously absorbs the ink, and the ink absorbing agent strongly receives the ink from the base material and holds it. Thus, the ink absorption speed of the entire sheet is further enhanced, and the ink is sufficiently diffused throughout the sheet.

The absorbent material in the form of a packaged body means a form in which powder (ink absorbing agent) is packaged with a planar or three-dimensional bag-like base material so as not to leak therefrom. The material of the base material and the embodiment of the packaging method are not limited as long as they hold 80% by weight or more of the ink absorbing agent without leakage. The amount of the ink absorbing agent to be packaged is preferably such that the volume of the ink absorbing agent containing ink absorbed is equal to or less than the volume of the packaged body.

Examples of the base material of the absorbent material in the form of a packaged body include those described above. Preferred among these is a fiber material. The size of mesh (mesh size) of the fiber material is preferably not greater than the particle size corresponding to R=80% in the average particle size measurement described in the examples of the ink absorbing agent of the invention. The fiber material having such a mesh size is capable of sufficiently preventing leakage of the ink absorbing agent.

The absorbent sheet may be formed of one absorbent layer including a base material and the ink absorbing agent or may be formed of two or more absorbent layers stacked to each other.

For example, the absorbent sheet may have a structure in which an ink absorbing agent-supported sheet and a sheet not supporting the ink absorbing agent are alternately stacked or a structure in which multiple sheets supporting the ink absorbing agent are arranged in amounts in ascending order, sheets supporting a smaller amount of the nonionic crosslinked polymer are arranged in the upper portion, for example.

Alternatively, the absorbent sheet may have a multilayer structure in which two or more nonwoven fabrics different in material (e.g., PP (polypropylene), PE (polyethylene), cellulose, polyamide, nylon, and polyester) each having the nonionic crosslinked polymer fixed thereon are stacked.

The absorbent sheet preferably has a thickness of 0.01 to 50 mm, more preferably 0.01 to 30 mm, still more preferably 0.01 to 20 mm, particularly preferably 0.05 to 10 mm, most preferably 0.1 to 5 mm.

The absorbent sheet preferably has a weight per unit area of 0.1 to 3000 g/m², more preferably 0.5 to 2500 g/m², still more preferably 1 to 1500 g/m².

The invention also relates to an ink-containing composition including the ink absorbing agent of the invention and ink absorbed by the agent.

Examples of the ink component include, but are not limited to, water, water-soluble organic solvents, dyes, pigments, and other additives.

EXAMPLE

The invention is described in more detail below with reference to, but not limited to, examples. Unless otherwise specified, "part(s)" means "part(s) by weight" and "%" means "% by mass".

<Evaluation of Liquid Absorption Capacities for Solvent (Including Deionized Water) and Solution>

About 0.1 g of a crosslinked polymer was precisely weighed (mass: W5 (g)) and put into a 4 cm×5 cm nonwoven fabric tea bag, and the tea bag was heat-sealed. These operations were performed in a room at a temperature of 23±2° C., a relative humidity of 50±5%, and atmospheric pressure. The tea bag was placed in a 50-mL (specified volume) glass screw tube and immersed in a solvent or a solution (in the case of deionized water, it has a conductivity of 10 μS/cm or lower) for 24 hours at room temperature (temperature: 23±2° C.) and atmospheric pressure. In the case of using liquid that is slowly absorbed, such as oil, the tea bag was immersed therein at 40° C. for 24 hours and then cooled for 10 minutes. Subsequently, the tea bag was taken out by pinching the end of the tea bag with tweezers, placed one face down on KIMTOWEL (Nippon Paper Crecia Co., Ltd.), and allowed to stand for five seconds. Then, the tea bag was placed the other face down on KIMTOWEL and allowed to stand for five seconds so that the liquid was removed. Then, the mass of the tea bag (W6 (g)) was weighed. Separately, the same operations were performed without a crosslinked polymer. Then, the mass of the tea bag (W4 (g)) was measured as a blank. The liquid absorption rate was determined according to the following equation as the liquid absorption capacity.

Liquid absorption rate (g/g)=(W6 (g)−W4 (g))/W5 (g)

<Measurement of Aspect Ratio>

The aspect ratio was determined by measuring the major and minor axes of cyclic N-vinyl lactam-based crosslinked polymer particles with an optical microscope and dividing the major axis by the minor axis. The aspect ratio was calculated by analyzing image data of a sample obtained from an optical microscope using a "particle image analysis system, Morphologi G3 (product of Malvern in Spectris Co., Ltd.)". The aspect ratios of any 100 or more particles were measured, and the average value of the aspect ratios was determined. Further, in the particles sorted in ascending order of the aspect ratio, the aspect ratio of the particle at 10% by number of all particles, the aspect ratio of the particle at 50% by number of all particles, and the aspect ratio of the particle at 90% by number of all particles were calculated.

In addition to the above described system, the aspect ratio may be measured by analyzing image data of a sample obtained from an optical or electron microscope using "image analyzing particle size distribution measurement software, Mac-view, ver. 4 (Mountech Co., Ltd.)".

<Quantification of Residual Monomer (N-Vinyl Lactam-Based Monomer) and by-Product (Compound Represented by the Formula (3))>

A 110-mL screw tube was charged with about 1 g of a particulate crosslinked polymer (mass: W7 (g)) and about 100 g of deionized water (mass: W8 (g)) (conductivity: 10 μS/cm or lower), which were precisely weighed. A stirrer bar was placed in the tube, and the tube was sealed. These operations were performed in a room at a temperature of 23±2° C., a relative humidity of 50±5%, and atmospheric pressure. Thereafter, the contents were stirred using a magnetic stirrer at room temperature (temperature: 23±2° C.) and atmospheric pressure for 16 hours or longer (rotation speed: 600 rpm). These operations extracted the residual monomer of the particulate crosslinked polymer (N-vinyl lactam-based monomer) and a by-product (compound represented by the formula (3)). The resulting extract solution was quantitatively analyzed by liquid chromatography under the following conditions.

Apparatus: "NANOSPACE SI-2", Shiseido Company, Limited
Column: "CAPCELLPAK C18 UG120" (20° C.), Shiseido Company, Limited
Eluent: Methanol for LC (Wako Pure Chemical Industries, Ltd.)/super pure water=1/24 (mass ratio) supplemented with 0.04 mass % of sodium 1-heptanesulfonate
Flow rate: 100 µL/min
Content (ppm)=measured value (ppm)×(W7 (g)+W8 (g))/W7 (g)

<Measurement of Extractable>

A 110-mL glass screw tube was charged with about 1 g of a particulate crosslinked polymer (mass: W9 (g)) and about 100 g of deionized water (mass: W10 (g)) (conductivity: 10 µS/cm or lower), which were precisely weighed. A stirrer bar was placed in the tube, and the tube was sealed. These operations were performed in a room at a temperature of 23±2° C., a relative humidity of 50±5%, and atmospheric pressure. Thereafter, the contents were stirred using a magnetic stirrer at room temperature (temperature: 23±2° C.) and atmospheric pressure for 16 hours or longer (rotation speed: 600 rpm). The resulting mixture was filtered through a qualitative filter paper (Model: No. 2, Advantec). Thus, an extract solution of an extractable was obtained.

Next, about 10 g of the extract solution (mass: W12 (g)) was put into an aluminum cup (mass: W11 (g)) having an about 5 cm diameter bottom face. The solution was allowed to stand in a dryer having a constant temperature of 120° C. for two hours, and thereby dried. After the drying, the sum of the mass (W13 (g)) of the aluminum cup and the mass of the extractable was measured, and the amount of extractable was determined using the following equation.

Amount of extractable (mass %)=((W13 (g)−W11 (g))/(W12 (g)×W9 (g)/W10 (g)))×100

<Measurement of Average Particle Size>

The 50% cumulative value was determined as an average particle size using a dry particle size distribution analyzer (Model: Mastersizer 3000, dry system, product of Malvern in Spectris Co., Ltd.). The measurement was performed under the following conditions.

<Measurement Conditions>
Dry-type laser diffraction scattering
Dispersion pressure: 1 bar
Particle refractive index: 1.52
Particle absorptivity: 0.01
Particle shape: Non-spherical
Medium name: Air
Measurement range: 0.1 to 3500 µm <Measurement of Viscosity>

A 50-mL glass screw tube was charged with 2.5 g of a particulate crosslinked polymer and 47.5 g of deionized water (conductivity: 10 µS/cm or lower), which were precisely weighed. A stirrer bar was placed in the tube, and the tube was sealed. These operations were performed in a room at a temperature of 23±2° C., a relative humidity of 50±5%, and atmospheric pressure. Thereafter, the contents were stirred using a magnetic stirrer at room temperature (temperature: 23±2° C.) and atmospheric pressure for 16 hours to prepare a 5 mass % aqueous dispersion of a cyclic N-vinyl lactam-based crosslinked polymer. Subsequently, the temperature of the aqueous solution was set at 25° C., and the viscosity was measured using a B-type viscometer (BM type, Toki Sangyo Co., Ltd.) (Rotor No. 4, rotation speed: 30 rpm).

Example 1-1

A desktop kneader (Model: PNV-1H, Chuorika Co., Ltd.) having a stainless-steel (SUS304) body vessel was charged with 130.0 parts of N-vinylpyrrolidone (hereinafter, also referred to as VP, Nippon Shokubai Co., Ltd.), 0.52 parts (0.18 mol % relative to VP) of triallyl cyanurate (hereinafter, also referred to as CTA) as a crosslinkable monomer, and 304.6 parts of deionized water. Subsequently, the vessel was purged with nitrogen at 100 mL/min for 30 minutes. Then, nitrogen was introduced at 30 mL/min, and the temperature was increased to 56° C. After the temperature of the liquid was stabilized at 56° C., 1.96 parts (0.25 g per 1 mol of the sum of VP and CTA used) of a 15 mass % aqueous solution of 2,2'-azobis[2-(2-imidazolin-2-yl)propane] dihydrochloride (hereinafter, also referred to as "VA-044") as an initiator was added to start polymerization. A gel formed by the polymerization reaction was aged at 90° C. for 60 minutes while it was pulverized with the rotating blade of the kneader to complete the polymerization. Subsequently, 65.0 parts of a 1 mass % aqueous solution of malonic acid was added over three minutes, followed by stirring at 90° C. for 60 minutes. In addition, 32.5 parts of a 2 mass % aqueous solution of diethanolamine was added over three minutes, followed by stirring for 30 minutes. The resulting gel was dried at 120° C. for two hours (precision constant temperature oven, Model: DF42, Yamato Scientific Co., Ltd., maximum opening degree, two stainless steel vats each having external dimensions of 232×297×50 H (mm) were used) to obtain a dried VP crosslinked polymer. The dried VP crosslinked polymer was ground using a grinder. Thus, a particulate VP crosslinked polymer (1-1) was obtained.

The physical properties of the VP crosslinked polymer (1-1) were evaluated by the above-described methods. In the evaluation, particles having a size of 250 to 500 µm of the VP crosslinked polymer (1-1) were used, which were obtained by classification of the VP crosslinked polymer (1) using JIS standard 250 µm-mesh and 500 µm-mesh sieves. The results are shown in Tables 1-1 and 1-2.

Example 1-2

A desktop kneader (Model: PNV-5H, Chuorika Co., Ltd.) was charged with 900.0 parts of VP, 4.05 parts (0.20 mol % relative to VP) of CTA as a crosslinkable monomer, and 2109.5 parts of deionized water. Subsequently, the kneader was purged with nitrogen at 400 mL/min for 40 minutes. Then, nitrogen was introduced at 100 mL/min, and the temperature was increased to 56° C. After the temperature of the liquid was stabilized at 56° C., 24.11 parts (0.45 g per 1 mol of the sum of VP and CTA used) of a 15 mass % aqueous solution of 2,2'-azobis(2-methylpropionamidine) dihydrochloride (hereinafter, also referred to as "V-50") as an initiator was added to start polymerization. A gel formed by the polymerization reaction was aged at 90° C. for 60 minutes while it was pulverized with the rotating blade of the kneader to complete the polymerization. Subsequently, 150.0 parts of a 3 mass % aqueous solution of malonic acid was added over five minutes, followed by stirring at 90° C. for 60 minutes. In addition, 30.0 parts of a 15 mass % aqueous solution of diethanolamine was added over three minutes, followed by stirring for 30 minutes. The resulting gel was dried at 120° C. for three hours (precision constant temperature oven, Model: DF42, Yamato Scientific Co., Ltd., maximum opening degree, two stainless steel vats each having external dimensions of 232×297×50 H (mm) were used, eight stainless steel vats each having external dimensions of 206×267×40 H (mm) were used) to obtain a dried VP crosslinked polymer. The dried VP crosslinked polymer was ground using a grinder. Thus, a particulate VP crosslinked polymer (1-2) was obtained.

The physical properties of the VP crosslinked polymer (1-2) were evaluated by the above-described methods. In the evaluation, particles having a size of 250 to 500 μm of the VP crosslinked polymer (1-2) were used, which were obtained by classification of the VP crosslinked polymer (1-2) using JIS standard 250 μm-mesh and 500 μm-mesh sieves. The results are shown in Table 1-1.

Example 1-3

A desktop kneader (Model: PNV-1H, Chuorika Co., Ltd.) having a stainless-steel (SUS304) body vessel was charged with 130.0 parts of VP, 1.30 parts (0.45 mol % relative to VP) of CTA as a crosslinkable monomer, and 306.4 parts of deionized water. Subsequently, the vessel was purged with nitrogen at 100 mL/min for 30 minutes. Then, nitrogen was introduced at 30 mL/min, and the temperature was increased to 56° C. After the temperature of the liquid was stabilized at 56° C., 1.97 parts (0.25 g per 1 mol of the sum of VP and CTA used) of a 15 mass % aqueous solution of VA-044 as an initiator was added to start polymerization. A gel formed by the polymerization reaction was aged at 90° C. for 60 minutes while it was pulverized with the rotating blade of the kneader to complete the polymerization. Subsequently, the resulting gel was dried at 120° C. for two hours (precision constant temperature oven, Model: DF42, Yamato Scientific Co., Ltd., maximum opening degree, two stainless steel vats each having external dimensions of 232×297×50 H (mm) were used) to obtain a dried VP crosslinked polymer. The dried VP crosslinked polymer was ground using a grinder. Thus, a particulate VP crosslinked polymer (1-3) was obtained.

The physical properties of the VP crosslinked polymer (1-3) were evaluated by the above-described methods. In the evaluation, particles having a size of 250 to 500 μm of the VP crosslinked polymer (1-3) were used, which were obtained by classification of the VP crosslinked polymer (1-3) using JIS standard 250 μm-mesh and 500 μm-mesh sieves. The results are shown in Table 1-1.

Comparative Example 1-1

A 1-L polypropylene (hereinafter, referred to as "PP") container was charged with 130.0 parts of VP, 0.13 parts (0.04 mol % relative to VP) of CTA as a crosslinkable monomer, and 303.6 parts of deionized water. Subsequently, stirring of the contents was started with a magnetic stirrer, and the container was purged with nitrogen at 100 mL/min for 30 minutes. Then, nitrogen was introduced at 30 mL/min, and the contents were heated to 56° C. under stirring. After the temperature of the liquid was stabilized at 56° C., 1.95 parts (0.25 g per 1 mol of the sum of VP and CTA used) of a 15 mass % aqueous solution of VA-044 as an initiator was added to start polymerization. A gel formed by the polymerization reaction was aged at 90° C. for 60 minutes to complete the polymerization. The resulting gel was pulverized using a desktop kneader (Model: PNV-1H, Chuorika Co., Ltd.), but it was only kneaded with the blade of the kneader but not pulverized. Subsequently, the gel was pulverized by hands and dried at 120° C. for two hours (precision constant temperature oven, Model: DF42, Yamato Scientific Co., Ltd., maximum opening degree, two stainless steel vats each having external dimensions of 232×297×50 H (mm) were used) to obtain a comparative dried VP crosslinked polymer. The comparative dried VP crosslinked polymer was ground using a grinder. Thus, a particulate comparative VP crosslinked polymer (1-1) was obtained.

The physical properties of the comparative VP crosslinked polymer (1-1) were evaluated by the above-described methods. In the evaluation, particles having a size of 250 to 500 μm of the comparative VP crosslinked polymer (1-1) were used, which were obtained by classification of the comparative VP crosslinked polymer (1-1) using JIS standard 250 μm-mesh and 500 μm-mesh sieves.

The results are shown in Table 1-1.

Comparative Example 1-2

A desktop kneader (Model: PNV-1H, Chuorika Co., Ltd.) having a stainless-steel (SUS304) body vessel was charged with 130.0 parts of VP, 0.26 parts (0.09 mol % relative to VP) of CTA as a crosslinkable monomer, and 303.9 parts of deionized water. Subsequently, the vessel was purged with nitrogen at 100 mL/min for 30 minutes. Then, nitrogen was introduced at 30 mL/min, and the temperature was increased to 56° C. After the temperature of the liquid was stabilized at 56° C., 1.95 parts (0.25 g per 1 mol of the sum of VP and CTA used) of a 15 mass % aqueous solution of VA-044 as an initiator was added to start polymerization. A gel formed by the polymerization reaction was aged at 90° C. for 60 minutes while rotating the blade of the kneader to complete the polymerization. The gel was kneaded with the blade of the kneader but not pulverized. Subsequently, the resulting gel was pulverized by hands and dried at 120° C. for two hours (precision constant temperature oven, Model: DF42, Yamato Scientific Co., Ltd., maximum opening degree, two stainless steel vats each having external dimensions of 232×297×50 H (mm) were used) to obtain a comparative dried VP crosslinked polymer. The comparative dried VP crosslinked polymer was ground using a grinder. Thus, a particulate comparative VP crosslinked polymer (1-2) was obtained.

The physical properties of the comparative VP crosslinked polymer (1-2) were evaluated by the above-described methods. In the evaluation, particles having a size of 250 to 500 μm of the comparative VP crosslinked polymer (1-2) were used, which were obtained by classification of the comparative VP crosslinked polymer (1-2) using JIS standard 250 μm-mesh and 500 μm-mesh sieves. The results are shown in Table 1-1.

Comparative Example 1-3

A desktop kneader (Model: PNV-1H, Chuorika Co., Ltd.) having a stainless-steel (SUS304) body vessel was charged with 130.0 parts of VP, 2.60 parts (0.89 mol % relative to VP) of CTA as a crosslinkable monomer, and 309.4 parts of deionized water. Subsequently, the vessel was purged with nitrogen at 100 mL/min for 30 minutes. Then, nitrogen was introduced at 30 mL/min, and the temperature was increased to 56° C. After the temperature of the liquid was stabilized at 56° C., 6.63 parts (1.12 g per 1 mol of the sum of VP and CTA used) of a 20 mass % aqueous solution of VA-044 as an initiator was added to start polymerization. A gel formed by the polymerization reaction was aged at 90° C. for 60 minutes while it was pulverized with the rotating blade of the kneader to complete the polymerization. Subsequently, the resulting gel was dried at 120° C. for two hours (precision constant temperature oven, Model: DF42, Yamato Scientific Co., Ltd., maximum opening degree, two stainless steel vats each having external dimensions of 232×297×50 H (mm) were used) to obtain a comparative dried VP crosslinked polymer. The comparative dried VP crosslinked polymer was ground using a grinder. Thus, a particulate comparative VP crosslinked polymer (1-3) was obtained.

The physical properties of the comparative VP crosslinked polymer (1-3) were evaluated by the above-described methods. In the evaluation, particles having a size of 250 to 500 μm of the comparative VP crosslinked polymer (1-3) were used, which were obtained by classification of the comparative VP crosslinked polymer (1-3) using JIS standard 250 μm-mesh and 500 μm-mesh sieves. The results are shown in Table 1-1.

400 mL/min for 40 minutes. Then, nitrogen was introduced at 100 mL/min, and the temperature was increased to 56° C. After the temperature of the liquid was stabilized at 56° C., 42.59 parts (0.78 g per 1 mol of the sum of VP and P-30M used) of a 15 mass % aqueous solution of 2,2'-azobis(2-methylpropionamidine) dihydrochloride (hereinafter, also referred to as "V-50") as an initiator was added to start polymerization. A gel formed by the polymerization reaction was aged at 90° C. for 60 minutes while it was pulverized with the rotating blade of the kneader to complete the polymerization. Subsequently, 225.0 parts of a 2 mass % aqueous solution of malonic acid was added over five minutes, followed by stirring at 90° C. for 60 minutes. In addition, 50.0 parts of a 9 mass % aqueous solution of diethanolamine was added over three minutes, followed by stirring for 30 minutes. The resulting gel was dried at 120° C. for three hours (precision constant temperature oven, Model: DF42, Yamato Scientific Co., Ltd., maximum opening degree, two stainless steel vats each having external dimensions of 232×297×50 H (mm) were used, eight stainless steel vats each having external dimensions of 206×267×40 H (mm) were used) to obtain a dried VP crosslinked polymer. The dried VP crosslinked polymer was preground

TABLE 1-1

|  | Example 1-1 | Example 1-2 | Example 1-3 | Comparative Example 1-1 | Comparative Example 1-2 | Comparative Example 1-3 |
|---|---|---|---|---|---|---|
|  | Crosslinked polymer | | | | | |
|  | VP crosslinked polymer (1-1) | VP crosslinked polymer (1-2) | VP crosslinked polymer (1-3) | Comparative VP crosslinked polymer (1-1) | Comparative VP crosslinked polymer (1-2) | Comparative VP crosslinked polymer (1-3) |
| Amount of crosslinkable monomer (mol %) *1 | 0.18 | 0.20 | 0.45 | 0.04 | 0.09 | 0.89 |
| Deionized water absorption capacity (g/g) | 22 | 24 | 16 | 40 | 32 | 12 |
| Ethanol absorption capacity (g/g) | 21 | 24 | 15 | 38 | 31 | 10 |
| Amount of by-product (Compound represented by formula (2)) (ppm) | 4015 | 2701 | 1734 | 4083 | 3389 | 1302 |
| Amount of extractable (wt %) | 10 | 12 | 3 | 52 | 20 | 3 |

*1 Amount relative to 100 mol % of N-vinyl lactam-based monomer

TABLE 1-2

|  | Number of particles measured | Aspect ratio | | | |
|---|---|---|---|---|---|
|  |  | Average | 10% | 50% | 90% |
| VP crosslinked polymer (1-1) | 8120 | 1.41 | 1.11 | 1.37 | 2.07 |

Example 2-1

A desktop kneader (Model: PNV-5H, Chuorika Co., Ltd.) was charged with 900.0 parts of N-vinylpyrrolidone (hereinafter, also referred to as VP, Nippon Shokubai Co., Ltd.), 12.6 parts (0.6 mol % relative to VP) of pentaerythritol triallyl ether (trade name: neoallyl P-30M, hereinafter, also referred to as P-30M, Osaka Soda Co., Ltd.) (81 mass % of pentaerythritol triallyl ether, 11 mass % of pentaerythritol diallyl ether, 7 mass % of pentaerythritol tetraallyl ether) as a crosslinkable monomer, 4.5 parts of a 1 mass % aqueous solution of diethanolamine, and 2124.9 parts of deionized water. Here, P-30M was premixed with the aqueous solution of diethanolamine so that the pH was adjusted to 6 or higher before addition. The kneader was purged with nitrogen at using a grinder, followed by gringing using a target-type jet mill to obtain a particulate VP crosslinked polymer (2-1).

The water absorption capacity, ethanol absorption capacity, average particle size, aspect ratio, amount of a residual monomer (N-vinyl lactam-based monomer content), amount of a by-product, and an extractable of the VP crosslinked polymer (2-1) were determined. The measurement was performed by the above-described method. The results are shown in Tables 2-1 and 2-2.

Example 2-2

A desktop kneader (Model: PNV-5H, Chuorika Co., Ltd.) was charged with 1000.0 parts of VP, 15.0 parts (0.65 mol % relative to VP) of P-30M (the pH was adjusted to 6 or higher using diethanolamine) as a crosslinkable monomer, and 2368.33 parts of deionized water. Subsequently, the kneader was purged with nitrogen at 400 mL/min for 40 minutes. Then, nitrogen was introduced at 30 mL/min, and the temperature was increased to 56° C. After the temperature of the liquid was stabilized at 56° C., 47.37 parts (0.78 g per 1 mol of the sum of VP and P-30M used) of a 15 mass % aqueous solution of V-50 as an initiator was added to start polymerization. A gel formed by the polymerization reaction was aged at 90° C. for 60 minutes while it was pulverized with the rotating blade of the kneader to complete the polymerization. Subsequently, 500.0 parts of a 1.4 mass % aqueous solution of malonic acid was added over three minutes, followed by stirring at 90° C. for 60 minutes. In addition, 250.0 parts of a 2.8 mass % aqueous solution of diethanolamine was added over three minutes, followed by stirring for 30 minutes. The resulting gel was dried at 120° C. for three hours (precision constant temperature oven, Model: DF42, Yamato Scientific Co., Ltd., maximum opening degree, two stainless steel vats each having external dimensions of 232×297×50 H (mm) were used, eight stainless steel vats each having external dimensions of 206×267×40 H (mm) were used) to obtain a dried VP crosslinked polymer. The dried VP crosslinked polymer was freeze ground in the presence of liquid nitrogen to obtain a particulate VP crosslinked polymer (2-2).

The physical properties of the VP crosslinked polymer (2-2) were evaluated by the above-described methods. The results are shown in Table 2-1.

Example 2-3

A desktop kneader (Model: PNV-1H, Chuorika Co., Ltd.) having a stainless-steel (SUS304) body vessel was charged with 130.0 parts of VP, 0.52 parts (0.18 mol % relative to VP) of triallyl cyanurate (hereinafter, also referred to as CTA) as a crosslinkable monomer, and 304.6 parts of deionized water. Subsequently, the vessel was purged with nitrogen at 100 mL/min for 30 minutes. Then, nitrogen was introduced at 30 mL/min, and the temperature was increased to 56° C. After the temperature of the liquid was stabilized at 56° C., 1.96 parts (0.25 g per 1 mol of the sum of VP and CTA used) of a 15 mass % aqueous solution of 2,2'-azobis [2-(2-imidazolin-2-yl)propane] dihydrochloride (hereinafter, also referred to as "VA-044") as an initiator was added to start polymerization. A gel formed by the polymerization reaction was aged at 90° C. for 60 minutes while it was pulverized with the rotating blade of the kneader to complete the polymerization. Subsequently, 65.0 parts of a 1 mass % aqueous solution of malonic acid was added over three minutes, followed by stirring at 90° C. for 60 minutes. In addition, 32.5 parts of a 2 mass % aqueous solution of diethanolamine was added over three minutes, followed by stirring for 30 minutes. The resulting gel was dried at 120° C. for two hours (precision constant temperature oven, Model: DF42, Yamato Scientific Co., Ltd., maximum opening degree, two stainless steel vats each having external dimensions of 232×297×50 H (mm) were used) to obtain a dried VP crosslinked polymer. The dried VP crosslinked polymer was ground using a grinder to a size that passed through a JIS standard 38 μm-mesh sieve. Thus, a particulate VP crosslinked polymer (2-3) was obtained.

The physical properties of the VP crosslinked polymer (2-3) were evaluated by the above-described methods. The results are shown in Table 2-1.

Comparative Example 2-1

A flask equipped with components such as a reflux condenser, a thermometer, a nitrogen gas inlet tube, and a T.K. homogenizer (stirrer, Tokushu Kika Kogyo Co., Ltd.), was charged with an aqueous solution prepared by dissolving 0.5 parts of polyoxyethylene alkyl sulfoammonium (trade name: HITENOL N-08, Dai-Ichi Kogyo Seiyaku Co., Ltd.) as a dispersion stabilizer to 400 parts of deionized water. Separately, a monomer composition containing 99.5 parts of stearyl acrylate and 0.5 parts of ethylene glycol dimethacrylate (hereinafter, also referred to as EGDMA) as a crosslinkable monomer was mixed with 1.0 part (3.24 g per 1 mol of the sum of stearyl acrylate and EGDMA used) of lauroyl peroxide as a polymerization initiator (organic peroxide) to prepare a mixture. The mixture was added to the flask containing the aqueous solution. Then, the contents were vigorously stirred at a rotational speed of 4000 rpm for five minutes to obtain a uniform suspension. The suspension was heated to 75° C. while nitrogen gas was blown into the flask. Then, a radical polymerization reaction was performed at this temperature for two hours under stirring to obtain a fine particle dispersion. The fine particle dispersion was separated into solid and liquid phases by natural precipitation. The resulting cake was dried by hot air at 50° C. for 10 hours. Thus, an oil-absorbing resin (comparative crosslinked polymer (2-1)) was obtained.

The physical properties of the comparative crosslinked polymer (2-1) were evaluated by the above-described methods. The results are shown in Table 2-1.

Comparative Example 2-2

A 250-mL polypropylene container was charged with 30.0 parts of acrylic acid (Nippon Shokubai Co., Ltd., 80 mass % aqueous solution) (hereinafter, also referred to as AA), 12.14 parts of sodium hydroxide (48 mass % aqueous solution), 0.021 parts (0.01 mol % relative to AA) of polyethylene glycol dimethacrylate (NK ester A-400, Shin-Nakamura Chemical Co., Ltd., number of moles of EO added: 9 mol) (hereinafter, also referred to as A-400) as a crosslinkable monomer, and 42.2 parts of deionized water (AA and sodium hydroxide were mixed before addition of A-400 and deionized water). Subsequently, stirring of the contents was started with a magnetic stirrer, and the container was purged with nitrogen at 100 mL/min for 30 minutes. Then, nitrogen was introduced at 30 mL/min, and 0.33 parts (0.12 g per 1 mol of the sum of AA and A-400 used) of a 15 mass % aqueous solution of sodium persulfate as an initiator and 0.04 parts of a 0.5 mass % aqueous solution of L-ascorbic acid was added to start polymerization under stirring. A gel formed by the polymerization reaction was aged at 90° C. for 30 minutes to complete the polymerization. The gel was pulverized using a desktop kneader (Model: PNV-1H, Chuorika Co., Ltd.) and then dried at 120° C. for two hours (precision constant temperature oven, Model: DF42, Yamato Scientific Co., Ltd., maximum opening degree, one stainless steel vat having external dimensions of 206×267×40 H (mm) was used) to obtain a dried AA-based crosslinked polymer (comparative crosslinked polymer (2-2)). The crosslinked polymer was ground using a grinder. Thus, a particulate comparative crosslinked polymer (2-2) was obtained.

The average particle size of the comparative crosslinked polymer (2-2) was 52.1 μm, determined by the above-described method.

Example 2-4

A dried VP crosslinked polymer was obtained in the same manner as in Example 2-3 except that the gel was dried at 120° C. for three hours. Subsequently, the dried VP crosslinked polymer was ground using a grinder and classified using JIS standard 250 μm-mesh and 500 μm-mesh sieves. The powder that passed through the 500 μm-mesh sieve and left on the 250 μm-mesh sieve was obtained as a particulate VP crosslinked polymer (VP crosslinked polymer (2-4)).

The physical properties of the VP crosslinked polymer (2-4) were evaluated by the above-described methods. The results are shown in Tables 2-1 and 2-2.

TABLE 2-1

| | Example 2-1 | Example 2-2 | Example 2-3 | Example 2-4 | Comparative Example 2-1 |
|---|---|---|---|---|---|
| | | | Crosslinked polymer | | |
| | VP crosslinked polymer (2-1) | VP crosslinked polymer (2-2) | VP crosslinked polymer (2-3) | VP crosslinked polymer (2-4) | Comparative crosslinked polymer (2-1) |
| Deionized water absorption capacity (g/g) | 25 | 25 | 21 | 22 | 1 |
| Ethanol absorption capacity (g/g) | 24 | 24 | 21 | 21 | 1 |
| (Average) Aspect ratio | 1.3 | 1.3 | 1.4 | 1.4 | 1.0 |
| Average particle size (μm) | 3 | 9 | 19 | 448 | 11 |
| Amount of N-vinyl lactam-based monomer (ppm) | 106 | 62 | 69 | 10 | 0 |
| Amount of by-product (Compound represented by formula (2)) (ppm) | 4899 | 4771 | 3269 | 4015 | 0 |
| Amount of extractable (%) | 19 | 17 | 16 | 10 | 1 |

TABLE 2-2

| | Number of particles measured | Aspect ratio | | | |
|---|---|---|---|---|---|
| | | Average | 10% | 50% | 90% |
| VP crosslinked polymer (2-1) | 14406 | 1.27 | 1.08 | 1.25 | 1.55 |
| VP crosslinked polymer (2-4) | 8120 | 1.41 | 1.11 | 1.37 | 2.07 | was placed the other face down on KIMTOWEL and allowed to stand for five seconds so that the liquid was removed. Then, the mass of the tea bag (W16 (g)) was measured. Separately, the same operations were performed without a crosslinked polymer. Then, the mass of the tea bag (W14 (g)) was measured as a blank. The liquid absorption rate was determined according to the following equation as oil absorption capacity.

$$\text{Liquid absorption rate (g/g)} = (W16\ (g) - W14\ (g))/W15\ (g)$$

The results are shown in Table 2-3.

TABLE 2-3

| | Crosslinked body | | | | | |
|---|---|---|---|---|---|---|
| | VP crosslinked polymer (2-1) | VP crosslinked polymer (2-2) | VP crosslinked polymer (2-3) | VP crosslinked polymer (2-4) | Comparative crosslinked polymer (2-1) | Comparative crosslinked polymer (2-2) |
| Oil absorption capacity (g/g) | 31 | 31 | 32 | 32 | 2 | 1 |

<Evaluation Example 2-1> Evaluation of Oil Absorption Capacity

The oil absorption capacities of the VP crosslinked polymers (2-1) to (2-4) obtained in Examples 2-1 to 2-4 and the comparative crosslinked polymers (2-1) and (2-2) obtained in Comparative Examples 2-1 and 2-2 were evaluated. The evaluation was performed in the following way.
(Evaluation Method)

About 0.1 g of a crosslinked body was precisely weighed (mass: W15 (g)) and put into a 4 cm×5 cm nonwoven fabric tea bag, and the tea bag was heat-sealed. These operations were performed in a room at a temperature of 23±2° C., a relative humidity of 50±5%, and atmospheric pressure. The tea bag was immersed in linoleic acid as an oil and placed in a dryer at a temperature of 40° C. After 24 hours, the test object was taken out from the dryer and cooled for 10 minutes. The tea bag was taken out from the oil by pinching the end of the tea bag with tweezers, placed one face down on KIMTOWEL (Nippon Paper Crecia Co., Ltd.), and allowed to stand for five seconds. Subsequently, the tea bag <Evaluation Example 2-2> Sensory Evaluation First, 3% aqueous solutions of the VP crosslinked polymers (2-1) to (2-3) obtained in Examples 2-1 to 2-3, the comparative crosslinked polymers (2-1) and (2-2) obtained in Comparative Examples 2-1 and 2-2, and polyvinylpyrrolidone (polyvinylpyrrolidone K-30, Nippon Shokubai Co., Ltd., K value (catalog value): 27.0 to 33.0, hereinafter, also referred to as PVP K-30) were prepared (97 g of ion exchange water was added to 3 g of each of the crosslinked polymers and PVP K-30 to prepare an aqueous solution or gelled substance). Each solution was applied to the inner side of a forearm of ten panel members and the coated part was washed with lukewarm water. The panel members evaluated the feeling of use of the aqueous solutions.

They evaluated the four items: moist feeling, no stickiness, applicability to the skin (application feeling), and adhesion feeling. The results are shown in Table 2-4.

In the table, the results are expressed as follows: Excellent: more than 8 out of 10 members evaluated good, Good: 6 or more out of 10 members evaluated good, Fair: 4 or more out of 10 members evaluated good, Bad: less than 4 out of 10 members evaluated good. The following results demonstrate that the products according to the invention provide less stickiness, excellent moist feeling, good applicability to the skin, and good adhesion feeling.

TABLE 2-4

| | Polymer | | | | | |
|---|---|---|---|---|---|---|
| | VP crosslinked polymer (2-1) | VP crosslinked polymer (2-2) | VP crosslinked polymer (2-3) | Comparative crosslinked polymer (2-1) | Comparative crosslinked polymer (2-2) | PVP K-30 |
| Moist feeling | Excellent | Excellent | Excellent | Poor | Good | Poor |
| No stickiness | Excellent | Excellent | Excellent | Excellent | Poor | Poor |
| Applicability to skin (application feeling) | Excellent | Excellent | Excellent | Fair | Poor | Good |
| Adhesion feeling | Excellent | Excellent | Excellent | Poor | Fair | Fair |

<Example 2-5> Preparation of Foundation

A foundation having the formulation shown in Table 2-5 was prepared using the VP crosslinked polymer (2-1) obtained in Example 2-1.

(Preparation Method)

The components were stirred at high speed and uniformly mixed. This foundation had excellent color developability and provided moist feeling.

TABLE 2-5

| Component No. | Example 2-5 | Amount (weight %) |
|---|---|---|
| 1 | VP crosslinked polymer (2-1) | 6.00 |
| 2 | Cyclomethicone | 3.50 |
| 3 | Dimethicone (5 cs) | 2.00 |
| 4 | Trimethylsiloxysilicate | 1.50 |
| 5 | Octyl methoxycinnamate | 1.00 |
| 6 | Phenoxyethanol | 0.40 |
| 7 | Tocophenol | 0.10 |
| 8 | Mica | 39.60 |
| 9 | Talc | 24.00 |
| 10 | Titanium oxide | 20.00 |
| 11 | Iron oxide | 1.90 |

The foundation was applied to ten panel members, and they evaluated the feeling thereof. They evaluated the two items: adhesiveness to the skin and sustainability. The results are shown in Table 2-6. In the table, the results are expressed as follows:

Good: 5 or more out of 10 members evaluated the foundation as being better than the blank (unblended product); and Bad: less than 5 out of 10 members evaluated the foundation as being better than the blank (unblended product).

As shown in Table 2-6, the foundation (Example 2-5) containing the product according to the invention had better adhesiveness to the skin and better sustainability than the blank (unblended product). On the other hand, the blank (unblended product) had poor adhesiveness to the skin and poor sustainability.

TABLE 2-6

| Example | Compound | Adhesiveness to skin | Sustainability |
|---|---|---|---|
| Example 2-5 | VP crosslinked polymer (2-1) | Good | Good |
| Blank | Free from VP crosslinked polymer (2-1) | Bad | Bad |

<Example 2-6 and Comparative Examples 2-3 and 2-4> Testing for Deodorizing Properties for Diacetyl Two glass lidded Petri dishes (inner diameter: 27 mm) were prepared. Then, 0.50 g of the VP crosslinked polymer (2-4) obtained in Example 2-4 was weighed into one Petri dish. In addition, 0.50 g of polyethylene glycol 20000 (hereinafter, also referred to as PEG, Wako Pure Chemical Industries, Ltd.) was placed on the other Petri dish and an empty Petri dish as a blank was prepared as Comparative Examples 2-3 and 2-4, respectively.

The three Petri dishes were covered and completely enclosed in sampling bags with a stopcock (Tedlar bag, GL Sciences Inc., volume: 3 L, shape: AAK) by heat-sealing. The sampling bags were evacuated, and 2 L of nitrogen gas was introduced into each bag, followed by introduction of 5 mL of diacetyl-containing nitrogen gas thereinto using a gas-tight syringe. The Petri dishes with a lid removed were allowed to stand for two hours in the respective bags. Then, a 100-mL portion of the gas was drawn three times from each bag with a gas sampler (Model: GV-100S, Gastec Corporation), and the reduction rates of diacetyl concentrations were compared using a gas detector tube (No. 92 for acetaldehyde, Gastec Corporation). The measured values were converted to diacetyl concentrations using a calibrated scale described in the manual of the detector tube.

The reduction rates of diacetyl were calculated using the following equation.

Reduction rate (%)=(gas concentration of blank−gas concentration of sample) (gas concentration of blank)×100

The results are shown in Table 2-7.

TABLE 2-7

| | Sample | Measured value (ppm) | Reduction rate (%) |
|---|---|---|---|
| Example 2-6 | VP crosslinked polymer (2-4) | 80 | 56 |
| Comparative Example 2-3 | PEG | 110 | 39 |

TABLE 2-7-continued

| | Sample | Measured value (ppm) | Reduction rate (%) |
|---|---|---|---|
| Comparative Example 2-4 | Blank | 180 | 0 |

<Example 2-7 and Comparative Examples 2-5 and 2-6> Testing for Deodorizing Properties for Nonenal Two glass lidded Petri dishes (inner diameter: 27 mm) were prepared. Then, 0.50 g of the VP crosslinked polymer (2-4) obtained in Example 2-4 was weighed into one Petri dish. In addition, 0.50 g of PEG was placed on the other Petri dish and an empty Petri dish was prepared as a blank as Comparative Examples 2-5 and 2-6, respectively.

The three Petri dishes were covered and completely enclosed in sampling bags with a stopcock (Tedlar bag, GL Sciences Inc., volume: 3 L, shape: AAK) by heat-sealing. The sampling bags were evacuated, and 0.5 L of nitrogen gas was introduced into each bag. Thereafter, 20 μL of a 10% ethanol solution of nonenal was introduced into each bag using a microsyringe. The Petri dishes with a lid removed were allowed to stand for two hours in the respective bags. Then, a 100-mL portion of the gas was drawn once from each bag with a gas sampler (Model: GV-100S, Gastec Corporation), and the concentrations of nonenal were measured using a gas detector tube (No. 91L for formaldehyde, Gastec Corporation). The reduction rates were calculated based on the actual value measured with the detector tube.

The reduction rates of nonenal were calculated using the following equation.

Reduction rate (%)=(gas concentration of blank−gas concentration of sample) (gas concentration of blank)×100

The results are shown in Table 2-8.

TABLE 2-8

| | Sample | Measured value (ppm) | Reduction rate (%) |
|---|---|---|---|
| Example 2-7 | VP crosslinked polymer (2-4) | 19.2 | 20 |
| Comparative Example 2-5 | PEG | 22.4 | 7 |
| Comparative Example 2-6 | Blank | 24.0 | 0 |

<Example 2-8 and Comparative Examples 2-7 and 2-8> Testing for Deodorizing Properties for Acetic Acid Two glass lidded Petri dishes (inner diameter: 27 mm) were prepared. Then, 0.50 g of the VP crosslinked polymer (2-4) obtained in Example 2-4 was weighed into one Petri dish. In addition, 0.50 g of PEG was placed on the other Petri dish and an empty Petri dish was prepared as a blank as Comparative Examples 2-8 and 2-9, respectively.

The three Petri dishes were covered and completely enclosed in sampling bags with a stopcock (Tedlar bag, GL Sciences Inc., volume: 3 L, shape: AAK) by heat-sealing. The sampling bags were evacuated, and 2 L of nitrogen gas was introduced into each bag. Thereafter, 5 mL of acetic acid-containing air was introduced into each bag using a gas-tight syringe. The Petri dishes with a lid removed were allowed to stand for two hours in the respective bags. Then, a 100-mL portion of the gas was drawn once from each bag with a gas sampler (Model: GV-100S, Gastec Corporation), and the concentrations of acetic acid were measured using a gas detector tube (No. 81 for acetic acid, Gastec Corporation). The reduction rates were calculated based on the actual value measured with the detector tube.

The reduction rates of acetic acid were calculated using the following equation.

Reduction rate (%)=(gas concentration of blank−gas concentration of sample)−(gas concentration of blank)×100

The results are shown in Table 2-9.

TABLE 2-9

| | Sample | Measured value (ppm) | Reduction rate (%) |
|---|---|---|---|
| Example 2-8 | VP crosslinked polymer (2-4) | 8 | 74 |
| Comparative Example 2-7 | PEG | 21 | 32 |
| Comparative Example 2-8 | Blank | 31 | 0 |

<Example 2-9 and Comparative Examples 2-9 and 2-10> Testing for Deodorizing Properties for Ammonia Two glass lidded Petri dishes (inner diameter: 27 mm) were prepared. Then, 1.0 g of the VP crosslinked polymer (2-4) obtained in Example 2-4 was weighed into one Petri dish. In addition, 1.0 g of PEG was placed on the other Petri dish and an empty Petri dish was prepared as a blank as Comparative Examples 2-10 and 2-11, respectively.

The three Petri dishes were covered and completely enclosed in sampling bags with a stopcock (Tedlar bag, GL Sciences Inc., volume: 3 L, shape: AAK) by heat-sealing. The sampling bags were evacuated, and 1 L of nitrogen gas was introduced into each bag. Thereafter, 0.37 g of an about 0.1% ammonia water was introduced into each bag using a disposable syringe. The Petri dishes with a lid removed were allowed to stand for two hours in the respective bags. Then, about 30-mL portion of the gas was drawn from each bag with a gas sampler (Model: GV-100S, Gastec Corporation), and the concentrations of ammonia were measured using a gas detector tube (No. 3 La for ammonia, Gastec Corporation). The measured values were corrected based on the scale length of the drawn gas in the gas sampler, and the reduction rates were determined.

The reduction rates of ammonia were calculated using the following equation.

Reduction rate (%)=(gas concentration of blank−gas concentration of sample)−(gas concentration of blank)×100

The results are shown in Table 2-10.

TABLE 2-10

| | Sample | Measured value (ppm) | Reduction rate (%) |
|---|---|---|---|
| Example 2-9 | VP crosslinked polymer (2-4) | 122 | 35 |

TABLE 2-10-continued

| Sample | | Measured value (ppm) | Reduction rate (%) |
|---|---|---|---|
| Comparative Example 2-9 | PEG | 188 | 0 |
| Comparative Example 2-10 | Blank | 188 | 0 |

<Example 2-10 and Comparative Examples 2-11 and 2-12> Testing for Deodorizing Properties for Methyl Mercaptan Two glass lidded Petri dishes (inner diameter: 27 mm) were prepared. Then, 5.0 g of the VP crosslinked polymer (2-4) obtained in Example 2-4 was weighed into one Petri dish. In addition, 5.0 g of PEG was placed on the other Petri dish and an empty Petri dish was prepared as a blank as Comparative Examples 2-11 and 2-12, respectively.

The three Petri dishes were covered and completely enclosed in sampling bags with a stopcock (Tedlar bag, GL Sciences Inc., volume: 3 L, shape: AAK) by heat-sealing. The sampling bags were evacuated, and 1 L of nitrogen gas was introduced into each bag. Thereafter, 0.40 g of about 0.06% methyl mercaptan sodium water was introduced into each bag using a disposable syringe. The Petri dishes with a lid removed were allowed to stand for two hours in the respective bags. Then, a 100-mL portion of the gas was drawn once from each bag with a gas sampler (Model: GV-100S, Gastec Corporation), and the concentrations of methyl mercaptan were measured using a gas detector tube (No. 71 for methyl mercaptan, Gastec Corporation). The reduction rates were calculated based on the actual value measured with the detector tube.

The reduction rates of methyl mercaptan were calculated using the following equation.

Reduction rate (%)=(gas concentration of blank−gas concentration of sample)÷(gas concentration of blank)×100

The results are shown in Table 2-11.

TABLE 2-11

| Sample | | Measured value (ppm) | Reduction rate (%) |
|---|---|---|---|
| Example 2-10 | VP crosslinked polymer (2-4) | 50 | 21 |
| Comparative Example 2-11 | PEG | 63 | 0 |
| Comparative Example 2-12 | Blank | 63 | 0 |

Table 2-12 shows the evaluation results of the testings for deodorizing properties in Examples 2-6 to 2-10 and Comparative Examples 2-3 to 2-12.

TABLE 2-12

| Sample | | Reduction rate (%) | | | | |
|---|---|---|---|---|---|---|
| | | Diacetyl | Nonenal | Acetate | Ammonia | Methyl mercaptan |
| Example | VP crosslinked polymer (2-4) | 56 | 20 | 74 | 35 | 21 |
| Comparative Example | PEG | 39 | 7 | 32 | 0 | 0 |
| | Blank | 0 | 0 | 0 | 0 | 0 |

These results demonstrate that the VP crosslinked polymer has excellent deodorizing properties for diacetyl, nonenal, acetic acid, ammonia, and methyl mercaptan.

<Evaluation Example 2-3> Evaluation of Concentration-Viscosity

Dispersions having different concentrations of the VP crosslinked polymer (2-2) obtained in Example 2-2 were prepared, and the viscosities at the respective concentrations were measured. As comparative samples, polyvinylpyrrolidone (polyvinylpyrrolidone K-90, Nippon Shokubai Co., Ltd., K value (catalog value): 88.0 to 96.0, hereinafter, also referred to as PVP) was used. The measurements were performed in the following way. The results are shown in Tables 2-13 and 2-14.

(Evaluation Method)

Dispersions of the VP crosslinked polymer (2-2) having a concentration of 1, 2, 3, 4, or 5 mass % were prepared using deionized water (conductivity: 10 µS/cm or lower), ethanol, or ethylene glycol as a solvent (room temperature (temperature: 23±2° C.), prepared by stirring for 16 hours under atmospheric pressure).

Separately, solutions of PVP having a concentration of 5, 10, or 20 mass % were prepared using deionized water, ethanol, or ethylene glycol as a solvent (dissolution was performed using a rotary shaker at room temperature). The temperatures of the solutions were set at 25° C., and the viscosities of the solutions were measured using a B-type viscometer (Model: BM, Toki Sangyo Co., Ltd.).

The viscosities of the VP crosslinked polymer (2-2) solutions rapidly increased at the time when the solutions reached the saturation of absorption. The solution (5%) having a rapidly increased viscosity was found to have thixotropy. The use of a dispersion medium having a large molecular size and a high viscosity such as ethylene glycol increased the viscosities of the dispersions of the VP crosslinked polymer (2-2). Further, the VP crosslinked polymer (2-2) required a smaller amount thereof to increase the viscosity than PVP (uncrosslinked).

TABLE 2-13

| | | Deionized water | | | Ethanol | | | Ethylene glycol | | |
|---|---|---|---|---|---|---|---|---|---|---|
| Concentration (mass %) | | Rotor No. | Rotation speed (rpm) | Viscosity (mPa·s) | Rotor No. | Rotation speed (rpm) | Viscosity (mPa·s) | Rotor No. | Rotation speed (rpm) | Viscosity (mPa·s) |
| VP crosslinked polymer (2-2) | 1 | 2 | 60 | 9 | 2 | 60 | 7 | 2 | 60 | 57 |
| | 2 | 2 | 60 | 14 | 2 | 60 | 14 | 4 | 60 | 360 |
| | 3 | 2 | 30 | 112 | 2 | 30 | 86 | 4 | 30 | 3500 |

TABLE 2-13-continued

|  | | Deionized water | | | Ethanol | | | Ethylene glycol | |
|---|---|---|---|---|---|---|---|---|---|
| Concentration (mass %) | | Rotor No. | Rotation speed (rpm) | Viscosity (mPa·s) | Rotor No. | Rotation speed (rpm) | Viscosity (mPa·s) | Rotor No. | Rotation speed (rpm) | Viscosity (mPa·s) |
| PVP | 4 | 4 | 60 | 600 | 4 | 30 | 680 | 4 | 6 | 79900 |
|  | 5 | 4 | 30 | 7480 | 4 | 12 | 13000 |  |  |  |
|  | 5 | 2 | 60 | 66 | 2 | 60 | 68 | 4 | 60 | 1280 |
|  | 10 | 4 | 60 | 570 | 4 | 60 | 500 | 4 | 60 | 3690 |
|  | 20 | 4 | 30 | 13540 | 4 | 12 | 9500 |  |  |  |

TABLE 2-14

|  | | Deionized water | |
|---|---|---|---|
| Concentration (mass %) | Rotor No. | Rotation speed (rpm) | Viscosity (mPa·s) |
| VP crosslinked polymer (2-2) | 5 | 4 | 30 | 7480 |
|  |  | 4 | 60 | 3920 |

<Measurement of Average Particle Sizes of Crosslinked Polymers (3-1) and (3-2)>

Sieves were combined from the top in descending order of mesh size. The crosslinked polymer was placed on the top sieve, and the sieves were shaken using an electromagnetic vibration small sieving machine (Model: M-2, Tsutsui Scientific Instruments Co., Ltd.) at 60 Hz for 10 minutes. At this time, the temperature was 23° C., and the humidity was 50%. The mass of the mixture left on each sieve was measured. The mesh size of each sieve and the mass ratio (percentage of remaining particles) R of particles that did not pass through the each sieve (the sum of the particles left on the certain sieve and the particles left on the sieves having a larger mesh size than the certain sieve) to all particles were plotted on a single logarithmic graph (horizontal axis: particle size (logarithmic scale), vertical axis: percentage of remaining particles). The particle size corresponding to R=50% was determined as the average particle size.

Production Example 3-1

A desktop kneader (Model: PNV-1H, Chuorika Co., Ltd.) was charged with 130.0 parts of N-vinylpyrrolidone (hereinafter, also referred to as VP, Nippon Shokubai Co., Ltd.), 0.52 parts (0.18 mol % relative to VP) of triallyl cyanurate (hereinafter, also referred to as CTA) as a crosslinking agent, and 304.6 parts of deionized water. Subsequently, the kneader was purged with nitrogen at 100 mL/min for 30 minutes. Then, nitrogen was introduced at 30 mL/min, and the temperature was increased to 56° C. After the temperature of the liquid was stabilized at 56° C., 1.96 parts (0.25 g per 1 mol of the sum of VP and CTA used) of a 15 mass % aqueous solution of 2,2'-azobis[2-(2-imidazolin-2-yl)propane] dihydrochloride (hereinafter, also referred to as "VA-044") as an initiator was added to start polymerization. A gel formed by the polymerization reaction was aged at 90° C. for 60 minutes while it was pulverized with the rotating blade of the kneader to complete the polymerization. Subsequently, 65.0 parts of a 1 mass % aqueous solution of malonic acid was added over three minutes, followed by stirring at 90° C. for 60 minutes. In addition, 32.5 parts of a 2 mass % aqueous solution of diethanolamine was added over three minutes, followed by stirring for 30 minutes. The resulting gel was dried at 120° C. for two hours (precision constant temperature oven, Model: DF42, Yamato Scientific Co., Ltd., maximum opening degree, two stainless steel vats each having external dimensions of 232×297×50 H (mm) were used) to obtain a dried VP crosslinked polymer. Then, the crosslinked polymer was ground using a grinder and classified using JIS standard 250 μm-mesh and 500 μm-mesh sieves. The powder that passed through the 500 μm-mesh sieve and left on the 250 μm-mesh sieve was obtained as a particulate VP crosslinked polymer (VP crosslinked polymer (3-1) of the invention). The average particle size of the VP crosslinked polymer (3-1) was 340 μm determined by the above-described method. The 50% cumulative value was 347 μm measured using a dry particle size distribution analyzer (Model: MT3100II, dry type, MicrotracBEL Corp.). The following describes the measurement conditions.

<Measurement Conditions>
Dry laser diffraction scattering method
Measurement time: 10 seconds
Dispersion pressure: None
Particle transmission: Transmit
Particle refractive index: 1.60
Particle shape: Non-spherical
Medium name: Air
Medium refractive index: 1.00
Measurement range: 0.7 to 1000 μm Production Example 3-2

A desktop kneader (Model: PNV-5H, Chuorika Co., Ltd.) was charged with 1000.0 parts of VP, 15.0 parts (0.65 mol % relative to VP) of pentaerythritol triallyl ether (trade name: neoallyl P-30M, Daiso Co., Ltd., the pH was adjusted to 6 or higher using diethanolamine) as a crosslinkable monomer, and 2368.33 parts of deionized water. Subsequently, the kneader was purged with nitrogen at 400 mL/min for 40 minutes. Then, nitrogen was introduced at 30 mL/min, and the temperature was increased to 56° C. After the temperature of the liquid was stabilized at 56° C., 47.37 parts (0.78 g per 1 mol of the sum of VP and pentaerythritol triallyl ether used) of a 15 mass % aqueous solution of 2,2'-azobis(2-methylpropionamidine) dihydrochloride (hereinafter, also referred to as "V-50") as an initiator was added to start polymerization. A gel formed by the polymerization reaction was aged at 90° C. for 60 minutes while it was pulverized with the rotating blade of the kneader to complete the polymerization. Subsequently, 500.0 parts of a 1.4 mass % aqueous solution of malonic acid was added over three minutes, followed by stirring at 90° C. for 60 minutes. In addition, 250.0 parts of a 2.8 mass % aqueous solution of diethanolamine was added over three minutes, followed by stirring for 30 minutes. The resulting gel was dried at 120° C. for three hours (precision constant temperature oven, Model: DF42, Yamato Scientific Co., Ltd., maximum opening degree, two stainless steel vats each having external dimensions of 232×297×50 H (mm) were used, eight stainless steel vats each having external dimensions of 206×267×40 H (mm) were used) to obtain a dried VP crosslinked polymer. Then, the crosslinked polymer was ground using a grinder and classified using JIS standard 250 μm-mesh and 500 μm-mesh sieves. The powder that passed through the 500 μm-mesh sieve and left on the 250 μm-mesh sieve was obtained as a particulate VP crosslinked polymer (VP crosslinked polymer (3-2) of the invention).

The average particle size of the VP crosslinked polymer (3-2) was 324 μm determined by the above-described method.

Comparative Production Example 3-1

First, 50 parts of polyethylene glycol 20000 was placed in a 50-ml glass separable flask and liquefied by stirring at 128° C. The stirring was performed at 50 rpm from the beginning to the end. After confirming the liquefaction, 2.5 parts of CTA was added to the flask as a crosslinking agent, and the contents were stirred for five minutes. Then, 0.12 parts of perbutyl 1-75 (NOF Corp.) was added thereto as an initiator, and the contents were continuously stirred at 128° C. for three hours. The resulting gel was cooled to 80° C., followed by pulverization using a desktop kneader (Model: PNV-1H, Chuorika Co., Ltd.) to obtain a polyethylene oxide crosslinked polymer. Then, the crosslinked polymer was ground using a grinder and classified using JIS standard 250 μm-mesh and 500 μm-mesh sieves. The powder that passed through the 500 μm-mesh sieve and left on the 250 μm-mesh sieve was obtained as a particulate polyethylene oxide crosslinked polymer (comparative crosslinked polymer (3-1) of the invention).

Examples 3-1 and 3-2 and Comparative Example 3-1

The VP crosslinked polymers (3-1) and (3-2) obtained in Production Examples 3-1 and 3-2 and the comparative crosslinked polymer (2-2) obtained in Comparative Production Example 2-2 were evaluated as Examples 3-1 and 3-2 and Comparative Example 3-1, respectively.

(Evaluation Method)

First, 0.1 g of a crosslinked polymer was put into a 4 cm×5 cm nonwoven fabric tea bag, and the tea bag was heat-sealed. The tea bag was placed in a 50 mL (specified volume) glass screw tube. These operations were performed in a room at a temperature of 23±2° C., a relative humidity of 50±5%, and atmospheric pressure. To the screw tube containing the tea bag was added 2 g of ink (BCI-351 (dye BK, C, M, or Y) or BCI-350 (PGBK (pigment BK)), Canon Inc.) at room temperature (temperature: 23±2° C.). The screw tube was allowed to stand for eight hours at room temperature (temperature: 23±2° C.) and atmospheric pressure. Thereafter, the inside of the screw tube was observed to evaluate the presence or absence of residual liquid (fluid liquid). The results are shown in Table 3-1. The components of the inks are shown in Table 3-2. In Table 3-1, good means the absence of residual liquid, and bad means the presence of residual liquid. The results demonstrate that the VP crosslinked polymers (3-1) and (3-2) according to the invention are superior to the comparative crosslinked polymer (2-2) in that the VP crosslinked polymers (3-1) and (3-2) are capable of absorbing many types of inks without leaving the ink.

TABLE 3-1

Evaluation of presence or absence of residual liquid

| Solution | Example 3-1 VP crosslinked polymer (3-1) | Example 3-2 VP crosslinked polymer (3-2) | Comparative Example 3-1 Comparative crosslinked polymer (2-2) |
|---|---|---|---|
| Pigment ink BK | Good | Good | Good |
| Dye ink BK | Good | Good | Bad |
| Dye ink C | Good | Good | Good |
| Dye ink M | Good | Good | Good |
| Dye ink Y | Good | Good | Bad |

TABLE 3-2

| Ink | Component | Amount (mass %) |
|---|---|---|
| Pigment BK | Glycerol | 10 to 15 |
|  | Glycol | 5 to 10 |
|  | Lactam | 5 to 10 |
|  | Water | 60 to 80 |
| Dye BK | Glycerol | 5 to 10 |
|  | Glycol | 15 to 20 |
|  | Lactam | 5 to 10 |
|  | Water | 60 to 80 |
| Dye C | Glycerol | 5 to 10 |
|  | Urea compound | 5 to 10 |
|  | Copper phthalocyanine compound | 1 to 5 |
|  | Copper phthalocyanine compound | 1 to 5 |
|  | Glycol | 10 to 15 |
|  | Water | 60 to 80 |
| Dye M | Urea compound | 5 to 10 |
|  | Glycerol | 1 to 5 |
|  | Pyridine azo compound | 1 to 5 |
|  | Water | 60 to 80 |
| Dye Y | Glycerol | 5 to 10 |
|  | Urea compound | 5 to 10 |
|  | Thiadiazole azo compound | 1 to 5 |
|  | Glycol | 10 to 15 |
|  | Water | 60 to 80 |

The invention claimed is:

1. A N-vinyl lactam-based crosslinked polymer-containing composition, the composition comprising a N-vinyl lactam-based crosslinked polymer that comprises:
a structural unit derived from a N-vinyl lactam; and
a structural unit derived from at least one selected from the group consisting of a crosslinkable monomer and a crosslinking agent, wherein
the N-vinyl lactam-based crosslinked polymer has an ethanol absorption capacity of 3 to 40 g per 1 g of the N-vinyl lactam-based crosslinked polymer,
the N-vinyl lactam-based crosslinked polymer contains a particle having an aspect ratio determined by the following method of 1.15 to 10 in a proportion of 10% to 100% (by number) of a total number of the N-vinyl lactam-based crosslinked polymer and having a proportion of an extractable of 35 mass % or less in 100 mass % of the entire polymer,
"Method of measuring aspect ratio"
the aspect ratio is determined as a value obtained by measuring the major and minor axes of a primary particle of the N-vinyl lactam-based cross-linked polymer with an optical or electron microscope and dividing the major axis by the minor axis,
a proportion of a residual monomer in the N-vinyl lactam-based crosslinked polymer is 200 ppm or less in 100 mass % of the N-vinyl lactam-based crosslinked polymer, and the composition has a proportion of a residual monomer of 200 ppm or less in 100 mass % of the N-vinyl lactam-based crosslinked polymer.

2. The N-vinyl lactam-based crosslinked polymer-containing composition according to claim 1,
wherein the N-vinyl lactam-based crosslinked polymer has a viscosity measured under the following conditions of 100 mPa·s or higher and lower than 10000 mPa·s,
"Viscosity measurement conditions"
sample: a 5 mass % aqueous dispersion of the N-vinyl lactam-based crosslinked polymer after 16-hour stirring;
measuring equipment: the sample is measured using a B-type viscometer at 25° C.; and
measurement conditions: Rotor No. 4, rotation speed: 30 rpm.

3. The N-vinyl lactam-based crosslinked polymer-containing composition according to claim 1,
wherein the N-vinyl lactam-based crosslinked polymer includes the structural unit derived from a N-vinyl lactam in a proportion of 30 to 100 mol % in 100 mol % of all structural units.

4. The N-vinyl lactam-based crosslinked polymer-containing composition according to claim 1,
wherein the N-vinyl lactam-based crosslinked polymer includes a structural unit derived from a N-vinyl lactam and at least one selected from the group consisting of a structural unit derived from a crosslinkable monomer and a structural unit derived from a crosslinking agent, and
the N-vinyl lactam-based crosslinked polymer contains the structural unit derived from at least one selected from the group consisting of a crosslinkable monomer and a crosslinking agent in a ratio of 0.01 to 2 mol % to 100 mol % of all structural units.

5. The N-vinyl lactam-based crosslinked polymer-containing composition according to claim 1,
wherein the crosslinkable monomer includes at least one selected from the group consisting of triallyl cyanurate, pentaerythritol (di, tri, or tetra)(meth)allyl ethers, triallyl isocyanurate, triallyl phosphate, triallylamine, diallyl carbonate, 1,3-bis(allyloxy)-2-propanol, divinylethylene urea, 1,4-butylene bis(N-vinylamide), and (di, tri, tetra, penta, hexa, hepta, or octa)allyl sucrose.

6. The N-vinyl lactam-based crosslinked polymer-containing composition according to claim 1,
wherein the crosslinkable monomer includes at least one selected from the group consisting of pentaerythritol (di, tri, or tetra)(meth)allyl ethers, diallyl carbonate, 1,3-bis(allyloxy)-2-propanol, divinylethylene urea, 1,4-butylene bis(N-vinylamide), and (di, tri, tetra, penta, hexa, hepta, or octa)allyl sucrose.

7. The N-vinyl lactam-based crosslinked polymer-containing composition according to claim 1,
wherein the N-vinyl lactam-based crosslinked polymer contains a structural unit derived from least one compound selected from the group consisting of triallyl cyanurate, pentaerythritol (di, tri, or tetra)(meth)allyl ethers, and (di, tri, tetra, penta, hexa, hepta, or octa)allyl sucrose.

8. The N-vinyl lactam-based crosslinked polymer-containing composition according to claim 1,
wherein the N-vinyl lactam-based crosslinked polymer has an average particle size of 0.1 to 100μm.

9. A deodorant comprising the N-vinyl lactam-based crosslinked polymer-containing composition according to claim 1.

10. A deodorizer comprising the deodorant according to claim 9.

11. A method of providing a deodorizing effect, comprising exposing an environment to the deodorant according to claim 9.

12. A cosmetic comprising the N-vinyl lactam-based crosslinked polymer-containing composition according to claim 1.

13. A method of providing a cosmetic effect, comprising externally applying the cosmetic of claim 12.

14. An ink absorbing agent comprising the N-vinyl lactam-based crosslinked polymer-containing composition according to claim 1.

15. An absorbent material comprising the ink absorbing agent according to claim 14.

16. An ink-containing composition comprising the ink absorbing agent according to claim 14 and ink absorbed by the ink absorbing agent.

17. A printer comprising the ink absorbing agent according to claim 14.

18. A printing method, comprising ink printing with the printer of claim 17.

19. A method of producing the N-vinyl lactam-based crosslinked polymer-containing composition according to claim 1,
the method comprising polymerizing a monomer component containing a N-vinyl lactam-based monomer and forming a crosslinked structure.

20. The method of producing the N-vinyl lactam-based crosslinked polymer-containing composition according to claim 19,
wherein the method uses a polymerization initiator in the polymerizing in an amount of 0.1 to 10 g relative to 1 mol of the monomer component.

21. A N-vinyl lactam-based crosslinked polymer-containing composition, the composition comprising a N-vinyl lactam-based crosslinked polymer that comprises:
a structural unit derived from a N-vinyl lactam; and
a structural unit derived from at least one selected from the group consisting of a crosslinkable monomer and a crosslinking agent, wherein
the N-vinyl lactam-based crosslinked polymer has an ethanol absorption capacity of 3 to 40 g per 1 g of the N-vinyl lactam-based crosslinked polymer,
the N-vinyl lactam-based crosslinked polymer contains a particle having an aspect ratio determined by the following method of 1.15 to 10 in a proportion of 10% to 100% (by number) of a total number of the N-vinyl lactam-based crosslinked polymer and having a proportion of an extractable of 35 mass % or less in 100 mass % of the entire polymer,
"Method of measuring aspect ratio"
the aspect ratio is determined as a value obtained by measuring the major and minor axes of a primary particle of the N-vinyl lactam-based cross-linked polymer with an optical or electron microscope and dividing the major axis by the minor axis,
a proportion of a residual monomer in the N-vinyl lactam-based crosslinked polymer is 200 ppm or less in 100 mass% of the N-vinyl lactam-based crosslinked polymer, and the composition has a proportion of a compound represented by the following formula (3) of 2 mass % or less in 100 mass % of the N-vinyl lactam-based crosslinked polymer:

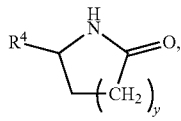

(3)

wherein $R^4$ represents a hydrogen atom or an optionally substituted C1-C10 alkyl group;

and y represents an integer of 1 to 3.

22. A N-vinyl lactam-based crosslinked polymer-containing composition, the composition comprising a N-vinyl lactam-based crosslinked polymer that comprises:
 a structural unit derived from a N-vinyl lactam; and
 a structural unit derived from at least one selected from the group consisting of a crosslinkable monomer and a crosslinking agent, wherein the N-vinyl lactam-based crosslinked polymer has an ethanol absorption capacity of 3 to 40 g per 1 g of the N-vinyl lactam-based crosslinked polymer, the N-vinyl lactam-based crosslinked polymer contains a particle having an aspect ratio determined by the following method of 1.15 to 10 in a proportion of 10% to 100% (by number) of a total number of the N-vinyl lactam-based crosslinked polymer and having a proportion of an extractable of 35 mass % or less in 100 mass % of the entire polymer, "Method of measuring aspect ratio"

the aspect ratio is determined as a value obtained by measuring the major and minor axes of a primary particle of the N-vinyl lactam-based cross-linked polymer with an optical or electron microscope and dividing the major axis by the minor axis, a proportion of a residual monomer in the N-vinyl lactam-based crosslinked polymer is 200 ppm or less in 100 mass % of the N-vinyl lactam-based crosslinked polymer, and the composition has a proportion of an extractable of 35 mass % or less in 100 mass % of the N-vinyl lactam-based crosslinked polymer.

* * * * *